United States Patent
Kubiak et al.

(10) Patent No.: US 10,835,241 B2
(45) Date of Patent: Nov. 17, 2020

(54) DEVICES, SYSTEMS, AND METHODS FOR REPAIRING SOFT TISSUE AND ATTACHING SOFT TISSUE TO BONE

(71) Applicant: CONEXTIONS, INC., Salt Lake City, UT (US)

(72) Inventors: Erik N. Kubiak, Las Vegas, NV (US); Roy M. Taylor, Salt Lake City, UT (US); Zackery K. Evans, Woods Cross, UT (US); Richard J. Linder, Sandy, UT (US); Scott D. Miles, Sandy, UT (US); Tyler J. Cole, Sandy, UT (US); Kent F. Beck, Layton, UT (US)

(73) Assignee: CONEXTIONS, INC., Salt Lake City, UT (US)

( * ) Notice: Subject to any disclaimer, the term of this patent is extended or adjusted under 35 U.S.C. 154(b) by 0 days.

(21) Appl. No.: 15/719,346

(22) Filed: Sep. 28, 2017

(65) Prior Publication Data

US 2018/0078253 A1 Mar. 22, 2018

Related U.S. Application Data

(63) Continuation-in-part of application No. 14/885,959, filed on Oct. 16, 2015, now Pat. No. 10,219,804, (Continued)

(51) Int. Cl.
*A61B 17/28* (2006.01)
*A61B 17/29* (2006.01)
(Continued)

(52) U.S. Cl.
CPC ........ *A61B 17/0642* (2013.01); *A61B 17/064* (2013.01); *A61B 17/0643* (2013.01);
(Continued)

(58) Field of Classification Search
CPC .... A61F 2002/0864; A61F 2002/30522; A61F 2002/30525; A61F 2002/30538;
(Continued)

(56) References Cited

U.S. PATENT DOCUMENTS 3,166,072 A 1/1965 Sullivan et al.
4,388,926 A 6/1983 Shalaby et al.
(Continued)

OTHER PUBLICATIONS

Mckenzie, "An Experimental Multiple Barbed Suture for the Long Flexor Tendons of the Palm and Fingers," Journal of Bone and Joint Surgery, Aug. 1967, pp. 440-447, vol. 49 B, No. 3.
(Continued)

*Primary Examiner* — Ann Schillinger
(74) *Attorney, Agent, or Firm* — David L. Stott

(57) ABSTRACT

Devices, systems and/or methods for repairing soft tissue adjacent a repair site. In one embodiment, a repair device is delivered with a delivery device system configured to move a cartridge with the repair device disposed therein toward an anvil with soft tissue positioned thereon. The delivery device linearly moves the cartridge toward the anvil with a worm drive positioned within a housing by rotating a thumb wheel disposed around the worm drive. Such linear movement is provided with a finger element extending from the worm drive that is configured to cooperate with an internal surface of the thumb wheel. With this arrangement, upon rotating the thumb wheel, the worm drive rotates with the finger element engaged with the internal surface of the thumb wheel to linearly move the cartridge toward the anvil.

10 Claims, 32 Drawing Sheets

Related U.S. Application Data which is a continuation-in-part of application No. 14/645,924, filed on Mar. 12, 2015, now Pat. No. 9,629,632, which is a continuation-in-part of application No. 13/953,709, filed on Jul. 29, 2013, now Pat. No. 9,427,309.

(60) Provisional application No. 62/401,042, filed on Sep. 28, 2016, provisional application No. 62/215,739, filed on Sep. 9, 2015, provisional application No. 62/129,742, filed on Mar. 6, 2015, provisional application No. 62/094,032, filed on Dec. 18, 2014, provisional application No. 62/064,533, filed on Oct. 16, 2014, provisional application No. 62/053,056, filed on Sep. 19, 2014, provisional application No. 62/040,451, filed on Aug. 22, 2014, provisional application No. 62/007,783, filed on Jun. 4, 2014, provisional application No. 61/952,114, filed on Mar. 12, 2014, provisional application No. 61/804,570, filed on Mar. 22, 2013, provisional application No. 61/677,239, filed on Jul. 30, 2012.

(51) Int. Cl.
| | | |
|---|---|---|
| *A61B 17/04* | (2006.01) | |
| *A61B 17/064* | (2006.01) | |
| *A61B 17/10* | (2006.01) | |
| *A61B 17/08* | (2006.01) | |
| *A61F 2/08* | (2006.01) | |
| *A61B 17/072* | (2006.01) | |
| *A61B 17/11* | (2006.01) | |
| *A61B 17/00* | (2006.01) | |

(52) U.S. Cl.
CPC ........ *A61B 17/0644* (2013.01); *A61B 17/072* (2013.01); *A61B 17/07292* (2013.01); *A61B 17/08* (2013.01); *A61B 17/105* (2013.01); *A61B 17/1146* (2013.01); *A61F 2/0811* (2013.01); *A61B 17/0487* (2013.01); *A61B 2017/00367* (2013.01); *A61B 2017/00438* (2013.01); *A61B 2017/00862* (2013.01); *A61B 2017/00867* (2013.01); *A61B 2017/0496* (2013.01); *A61B 2017/0641* (2013.01); *A61B 2017/07257* (2013.01); *A61B 2017/081* (2013.01); *A61B 2017/1103* (2013.01); *A61B 2017/1132* (2013.01); *A61F 2002/0829* (2013.01); *A61F 2002/0864* (2013.01); *A61F 2002/0888* (2013.01)

(58) Field of Classification Search
CPC .. A61F 2002/30556; A61F 2002/30579; A61F 2002/30616; A61F 2002/4627; A61F 2/0811; A61B 17/07207; A61B 34/20; A61B 90/37; A61B 2090/0811; A61B 2017/0046; A61B 17/068; A61B 17/072; A61B 2090/034; A61B 17/7082; A61B 90/14; A61B 34/70; A61B 17/105; A61B 2017/00473; A61B 2017/00477; A61B 2017/0496; A61B 17/0487; A61B 17/1626; A61B 5/4533; A61B 2017/0464; A61B 2017/07214

See application file for complete search history.

(56) References Cited

U.S. PATENT DOCUMENTS

| | | |
|---|---|---|
| 4,414,967 A | 11/1983 | Shapiro |
| 4,461,298 A | 7/1984 | Shalaby et al. |
| 4,469,101 A | 9/1984 | Coleman et al. |
| 4,489,875 A | 12/1984 | Crawford et al. |
| 4,532,926 A | 8/1985 | O'Holla |
| 4,534,350 A | 8/1985 | Golden et al. |
| 4,548,202 A | 10/1985 | Duncan |
| 4,610,250 A | 9/1986 | Green |
| 4,655,980 A | 4/1987 | Chu |
| 4,741,330 A | 5/1988 | Hayhurst |
| 4,776,890 A | 10/1988 | Chu |
| 4,796,612 A | 1/1989 | Reese |
| 4,810,549 A | 3/1989 | Abrams et al. |
| 4,873,976 A | 10/1989 | Schreiber |
| 4,942,875 A | 7/1990 | Hlavacek et al. |
| 4,946,467 A | 8/1990 | Ohi et al. |
| 4,960,420 A | 10/1990 | Goble et al. |
| 4,983,184 A | 1/1991 | Steinemann |
| 5,047,103 A | 9/1991 | Abrams et al. |
| 5,061,283 A | 10/1991 | Silvestrini |
| 5,163,956 A | 11/1992 | Liu et al. |
| 5,207,841 A | 5/1993 | Abrams |
| 5,250,049 A | 10/1993 | Michael |
| 5,290,552 A | 3/1994 | Sierra et al. |
| 5,292,334 A | 3/1994 | Howansky |
| 5,306,290 A | 4/1994 | Martins et al. |
| 5,306,500 A | 4/1994 | Rhee et al. |
| 5,312,023 A | 5/1994 | Green et al. |
| 5,326,013 A | 7/1994 | Green et al. |
| 5,329,943 A | 7/1994 | Johnson |
| 5,342,376 A | 8/1994 | Ruff |
| 5,346,746 A | 9/1994 | Abrams |
| 5,370,662 A | 12/1994 | Stone et al. |
| 5,389,098 A * | 2/1995 | Tsuruta ............ A61B 17/00234 606/41 |
| 5,413,791 A | 5/1995 | Rhee et al. |
| 5,446,091 A | 8/1995 | Rhee et al. |
| 5,447,265 A | 9/1995 | Vidal et al. |
| 5,458,636 A | 10/1995 | Brancato |
| 5,465,894 A | 11/1995 | Clark et al. |
| 5,480,644 A | 1/1996 | Freed |
| 5,510,418 A | 4/1996 | Rhee et al. |
| 5,523,348 A | 6/1996 | Rhee et al. |
| 5,527,341 A | 6/1996 | Gogolewski et al. |
| 5,542,594 A | 8/1996 | McKean et al. |
| 5,556,428 A | 9/1996 | Shah |
| 5,575,803 A | 11/1996 | Cooper et al. |
| 5,580,923 A | 12/1996 | Yeung et al. |
| 5,597,637 A | 1/1997 | Abrams et al. |
| 5,603,443 A | 2/1997 | Clark et al. |
| 5,607,094 A | 3/1997 | Clark et al. |
| 5,630,824 A | 5/1997 | Hart |
| 5,630,842 A | 5/1997 | Brodniewicz |
| 5,649,937 A | 7/1997 | Bito et al. |
| 5,665,112 A | 9/1997 | Thal |
| 5,667,839 A | 9/1997 | Berg |
| 5,711,472 A | 1/1998 | Bryan |
| 5,713,903 A | 2/1998 | Sander et al. |
| 5,716,981 A | 2/1998 | Hunter et al. |
| 5,723,008 A | 3/1998 | Gordon |
| 5,728,110 A | 3/1998 | Vidal et al. |
| 5,732,871 A | 3/1998 | Clark et al. |
| 5,756,678 A | 5/1998 | Shenoy et al. |
| 5,766,250 A | 6/1998 | Chervitz et al. |
| 5,800,544 A | 9/1998 | Demopulos et al. |
| 5,807,581 A | 9/1998 | Rosenblatt et al. |
| 5,858,156 A | 1/1999 | Abrams et al. |
| 5,860,229 A | 1/1999 | Morgenstern |
| 5,865,361 A | 2/1999 | Milliman et al. |
| 5,908,427 A | 6/1999 | McKean et al. |
| 5,916,224 A | 6/1999 | Esplin |
| 5,961,520 A | 10/1999 | Beck, Jr. et al. |
| 5,964,774 A | 10/1999 | McKean et al. |
| 5,980,524 A | 11/1999 | Justin et al. |
| 5,997,811 A | 12/1999 | Esposito |
| 6,010,764 A | 1/2000 | Abrams |
| 6,013,083 A | 1/2000 | Bennett |
| 6,027,523 A | 2/2000 | Schmieding |
| 6,030,410 A | 2/2000 | Zurbrugg |
| 6,045,560 A | 4/2000 | McKean et al. |
| 6,079,606 A | 6/2000 | Milliman et al. |

(56) References Cited

U.S. PATENT DOCUMENTS

| | | |
|---|---|---|
| 6,080,192 A | 6/2000 | Demopulos et al. |
| 6,083,242 A | 7/2000 | Cook |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,206,886 B1 | 3/2001 | Bennett |
| 6,241,139 B1 | 6/2001 | Milliman et al. |
| 6,241,747 B1 | 6/2001 | Ruff |
| 6,250,532 B1 | 6/2001 | Green et al. |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,464,706 B1 | 10/2002 | Winters |
| 6,472,171 B1 | 10/2002 | Toman et al. |
| 6,485,503 B2 | 11/2002 | Jacobs et al. |
| 6,491,714 B1 | 12/2002 | Bennett |
| 6,495,127 B1 | 12/2002 | Wallace et al. |
| 6,515,016 B2 | 2/2003 | Hunter |
| 6,517,579 B1 | 2/2003 | Paulos et al. |
| 6,533,802 B2 | 3/2003 | Bojarski et al. |
| 6,544,273 B1 | 4/2003 | Harari et al. |
| 6,551,315 B2 | 4/2003 | Kortenbach et al. |
| 6,569,186 B1 | 5/2003 | Winters et al. |
| 6,575,976 B2 | 6/2003 | Grafton |
| 6,644,532 B2 | 11/2003 | Green et al. |
| 6,645,226 B1 | 11/2003 | Jacobs et al. |
| 6,648,893 B2 | 11/2003 | Dudasik |
| 6,652,563 B2 | 11/2003 | Dreyfuss |
| 6,656,183 B2 | 12/2003 | Colleran et al. |
| 6,666,873 B1 | 12/2003 | Cassell |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,233 B1 | 6/2004 | Baldwin et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,905,513 B1 | 6/2005 | Metzger |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,074,203 B1 | 7/2006 | Johanson et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,189,238 B2 | 3/2007 | Lombardo et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,275,674 B2 | 10/2007 | Racenet et al. |
| 7,296,724 B2 | 11/2007 | Green et al. |
| 7,303,107 B2 | 12/2007 | Milliman et al. |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,442,202 B2 | 10/2008 | Dreyfuss |
| 7,464,848 B2 | 12/2008 | Green et al. |
| 7,510,566 B2 | 3/2009 | Jacobs et al. |
| 7,530,484 B1 | 5/2009 | Durrani |
| 7,530,990 B2 | 5/2009 | Perriello et al. |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,640,617 B2 | 1/2010 | Kennedy et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,731,718 B2 | 6/2010 | Schwammberger et al. |
| 7,771,468 B2 | 8/2010 | Whitbourne et al. |
| 7,794,484 B2 | 9/2010 | Stone et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,887,551 B2 | 2/2011 | Bojarski et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racenet |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |

(56) References Cited

U.S. PATENT DOCUMENTS

| | | |
|---|---|---|
| 8,328,061 B2 | 12/2012 | Kasvikis |
| 8,342,377 B2 | 1/2013 | Milliman et al. |
| 8,343,186 B2 | 1/2013 | Dreyfuss et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,491,600 B2 | 7/2013 | McDevitt et al. |
| 8,500,776 B2 | 8/2013 | Ebner |
| 8,518,091 B2 | 8/2013 | McDevitt et al. |
| 8,540,131 B2 | 9/2013 | Swayze |
| 8,550,325 B2 | 10/2013 | Cohen et al. |
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |
| 8,840,003 B2 | 9/2014 | Morgan et al. |
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0192280 A1 | 12/2002 | Hunter et al. |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0224023 A1 | 11/2004 | Hunter et al. |
| 2004/0254609 A1 | 12/2004 | Esplin |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Dean et al. |
| 2009/0280153 A1 | 11/2009 | Hunter et al. |
| 2009/0324720 A1 | 12/2009 | He et al. |
| 2010/0016872 A1 | 1/2010 | Bayton et al. |
| 2010/0160718 A1 | 6/2010 | Villafana et al. |
| 2010/0193568 A1* | 8/2010 | Scheib ............ A61B 17/07207 227/176.1 |
| 2010/0217314 A1 | 8/2010 | Holsten et al. |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1 | 4/2012 | Shelton, IV et al. |
| 2012/0130374 A1 | 5/2012 | Bouduban et al. |
| 2012/0203253 A1 | 8/2012 | Kubiak |
| 2012/0245629 A1 | 9/2012 | Gross et al. |
| 2013/0131781 A1 | 5/2013 | Greenhalgh et al. |
| 2013/0144310 A1 | 6/2013 | Gordon et al. |
| 2013/0197580 A1 | 8/2013 | Perriello et al. |
| 2014/0039551 A1 | 2/2014 | Donahue |
| 2014/0214037 A1 | 7/2014 | Mayer et al. |

(56) References Cited

U.S. PATENT DOCUMENTS

| | | |
|---|---|---|
| 2015/0245841 A1 | 9/2015 | Linder et al. |
| 2015/0272567 A1 | 10/2015 | Feezor et al. |
| 2015/0289866 A1 | 10/2015 | Bowen et al. |
| 2016/0066900 A1 | 3/2016 | Brunsvold et al. |
| 2016/0100835 A1 | 4/2016 | Linder et al. |
| 2016/0100933 A1 | 4/2016 | Linder et al. |
| 2016/0174965 A1 | 6/2016 | Brunsvold |
| 2017/0027578 A1 | 2/2017 | Friedman et al. |
| 2017/0056158 A1 | 3/2017 | Saing |
| 2017/0156847 A1 | 6/2017 | Ricci et al. |
| 2017/0333026 A1 | 11/2017 | Dreyfuss et al. |
| 2018/0078253 A1 | 3/2018 | Kubiak et al. |
| 2018/0200042 A1 | 7/2018 | Kubiak et al. |

OTHER PUBLICATIONS

Momose et al., "Suture Techniques With High Breaking Strength and Low Gliding Resistance: Experiments in the Dog Flexor Digitorum Pofundus Tendon," Acta Orthop Scand, 2001, 72(6):635-641.

Leung et al., "Barbed, Bi-Directional Medical Sutures: Biomechanical Properties and Wound Closure Efficacy Study," Society for Biomaterials 28ths Annual Meeting Transactions, 2002, p. 724.

Chunfeng et al., "Enhancing the Strength of the Tendon-Suture Interface Using 1-Ethyl-3-(3-dimethylaminoproply) Carbodimide Hydrochloride and Cyanoacrylate," Journal of Hand Surger, 2007, 32(5): 606-11.

Burkhead et al., "Use of Graft Jacket as an Augmentation for Massive Rotator Cuff Tears," Semin Arthro, 2007, 18(1): 11-18.

Hirpara et al., "A Barbed Device for Digital Flexor Tendon Repair," http://proceedings.jbjs.org.uk/cgi/content/abstract/92-B/SUPP_II/291-d, Mar. 2010.

International Search Report dated Feb. 26, 2016 for International Application No. PCT/US2015/56059 (14 pages).

International Search Report dated Jul. 20, 2015 for International Application No. PCT/US2015/020231 (10 pages).

International Search Report dated Oct. 10, 2013 for International Application No. PCT/US2013/052735 (7 pages).

Office Action with English Translation issued in CN 201580066314.4 dated Jun. 22, 2018.

Supplementary European Search Report issued in EP 15850646.9 dated Jun. 25, 2018.

International Search Report dated May 8, 2019 for International Application No. PCT/US2019/018628 (14 pages).

Office Action issued in EP 15850646.9 dated Sep. 19, 2019.

\* cited by examiner

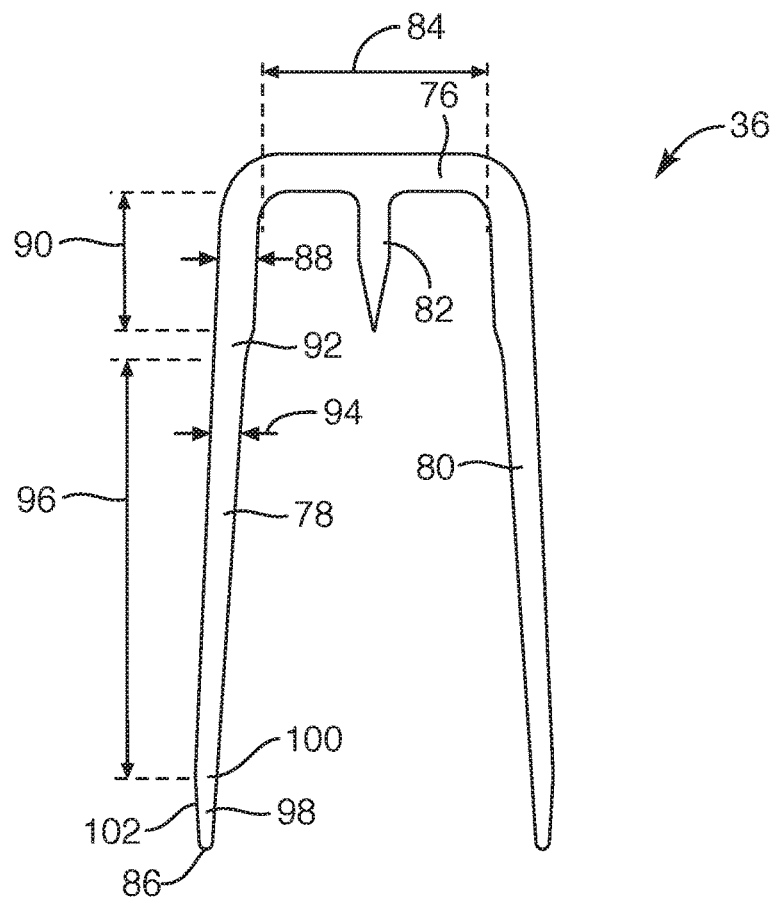
FIG. 4
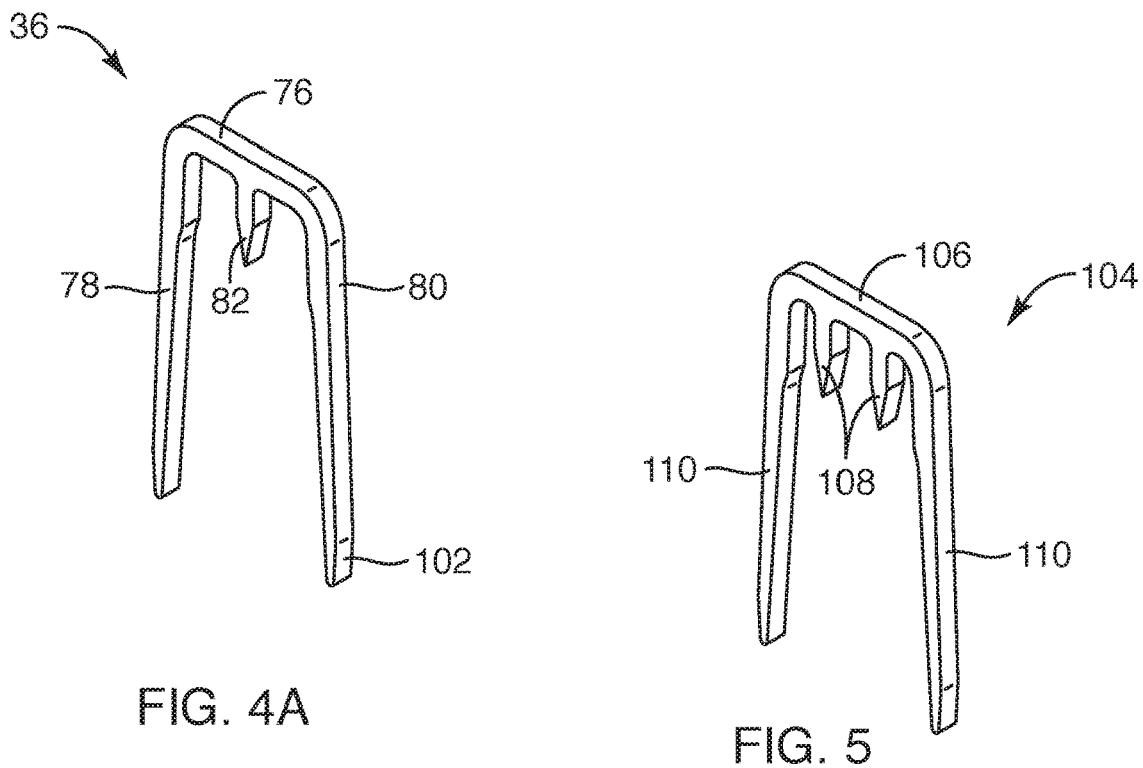
FIG. 4A
FIG. 5

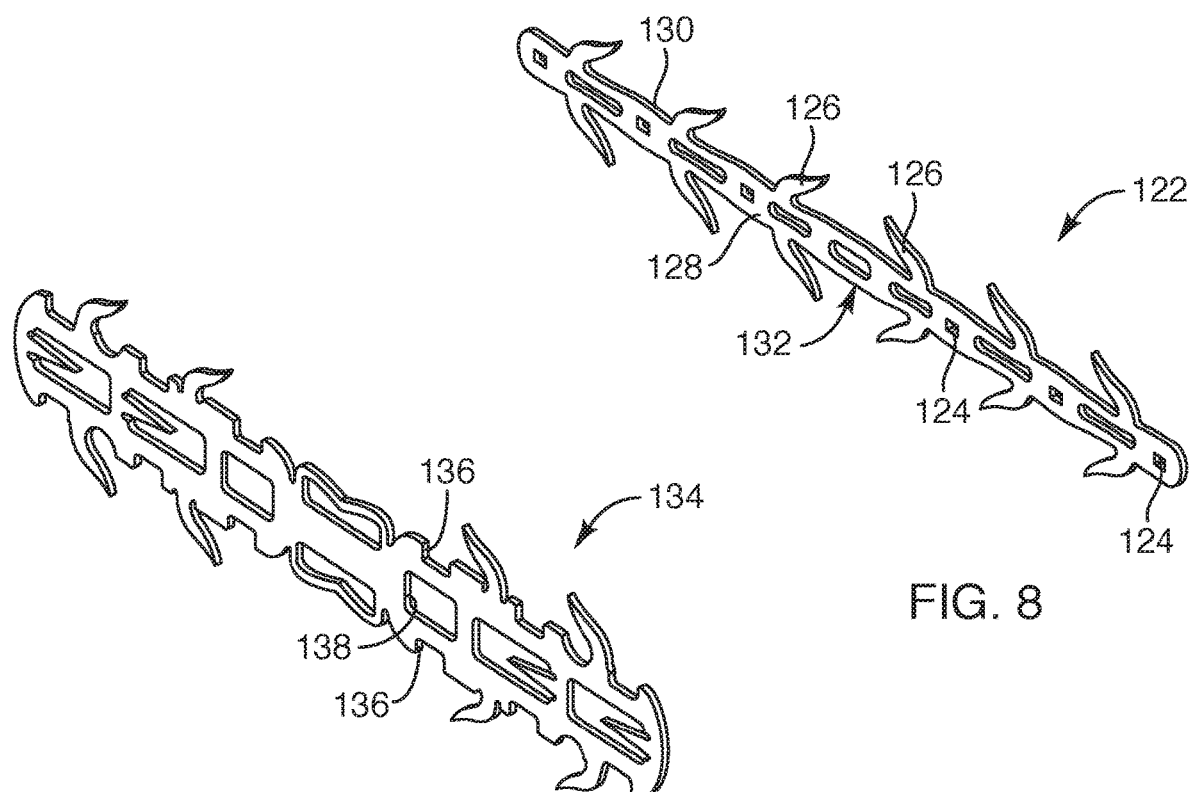
FIG. 8
FIG. 9
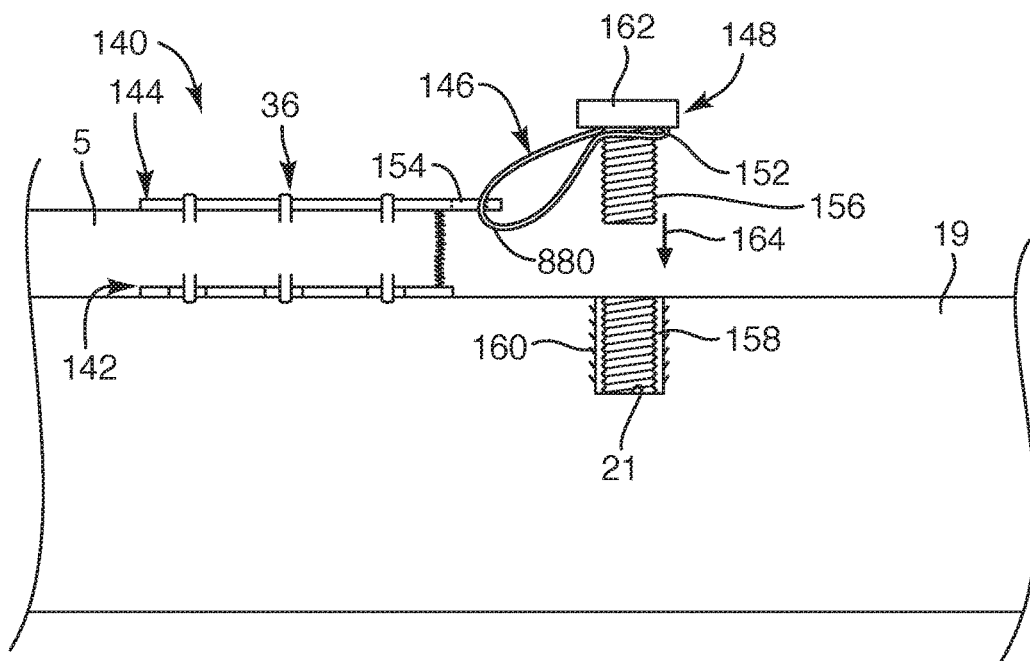
FIG. 10

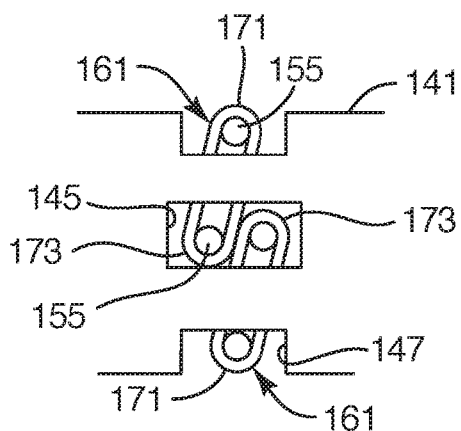
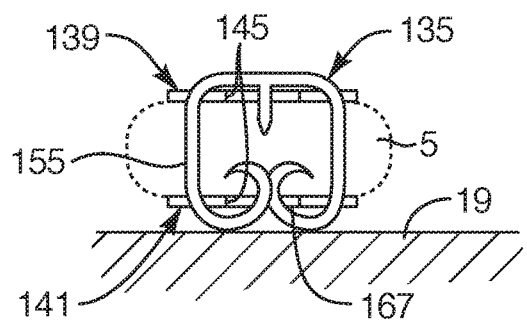
FIG. 11A  FIG. 11B
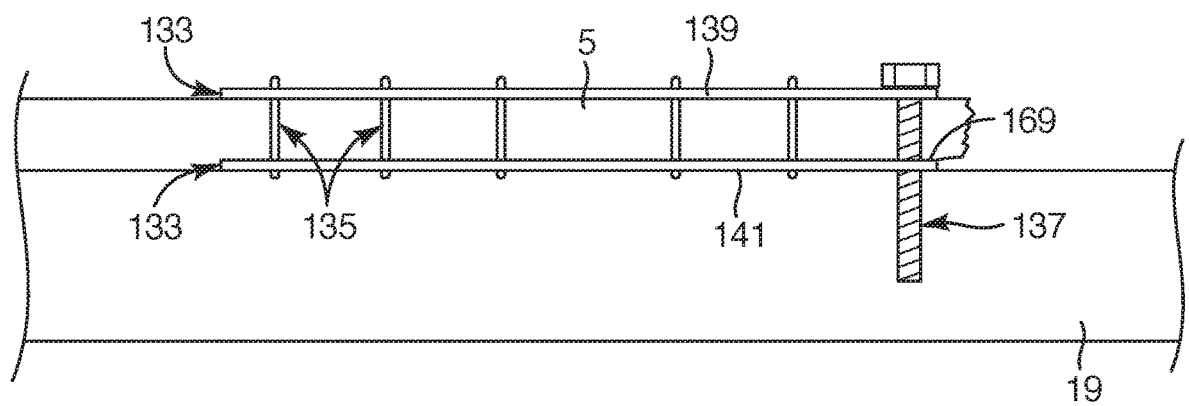
FIG. 12

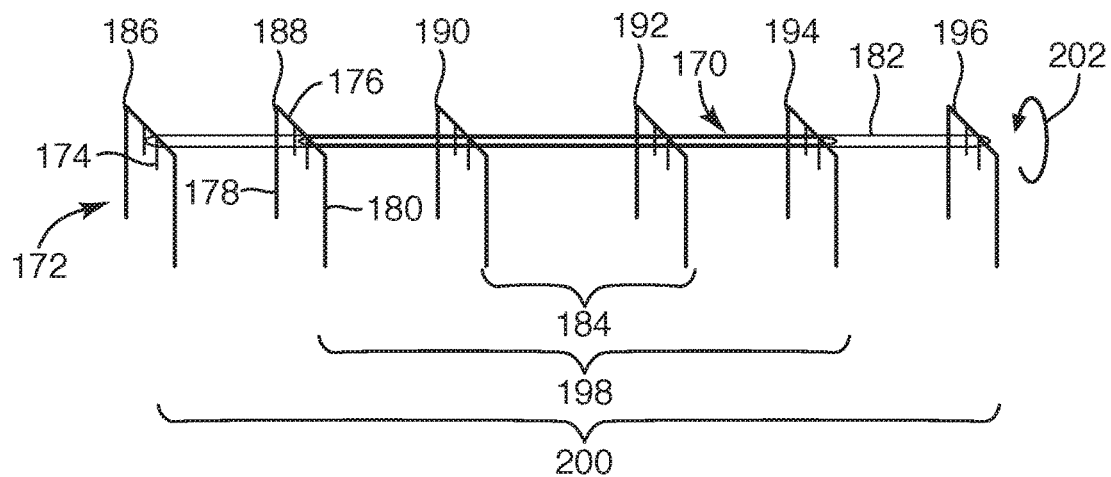
FIG. 13
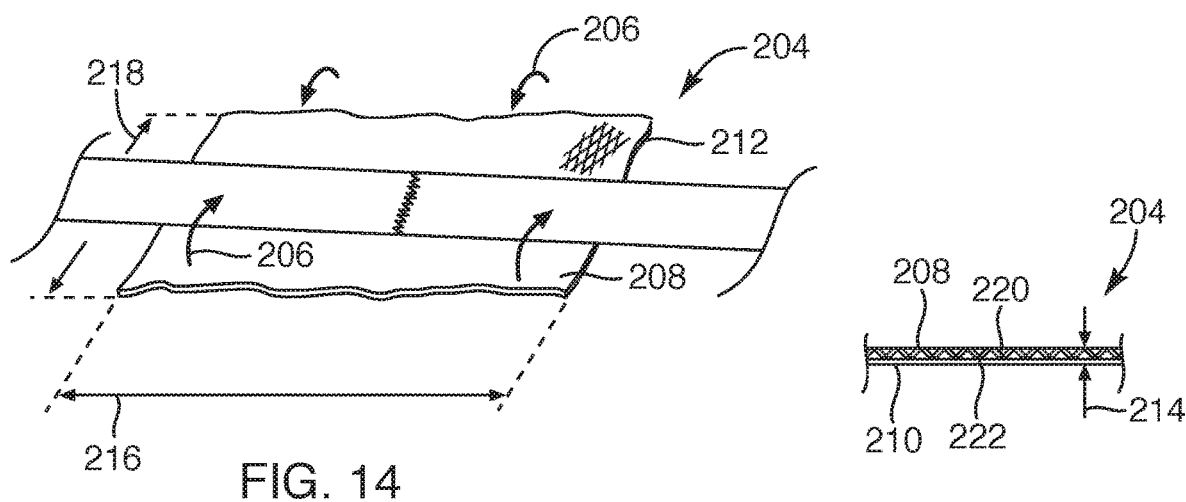
FIG. 14
FIG. 14A
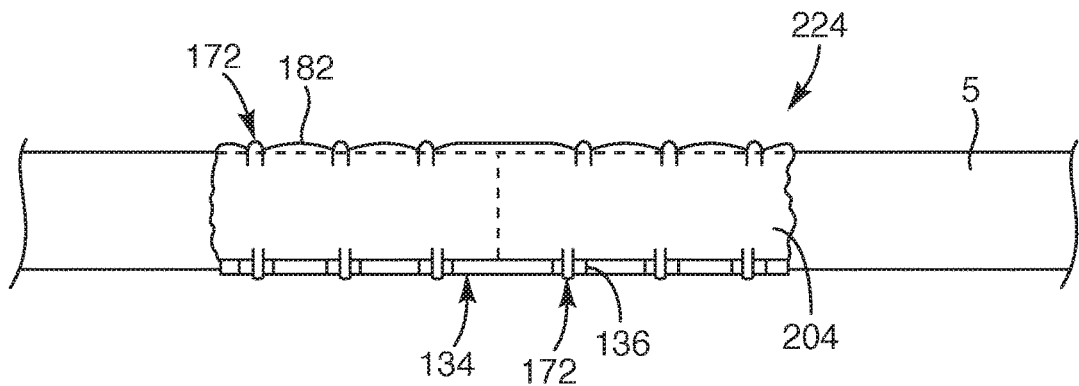
FIG. 15

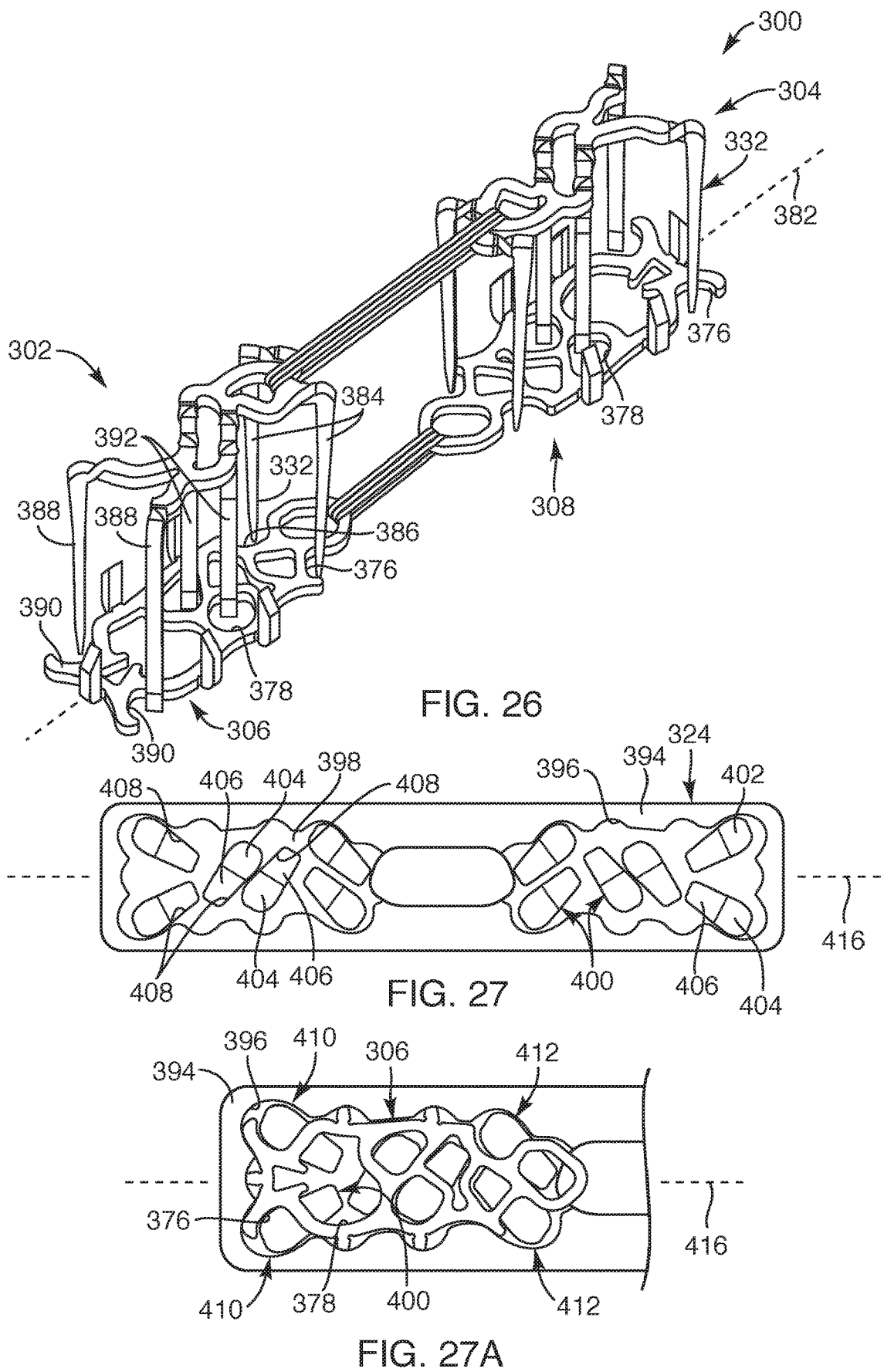

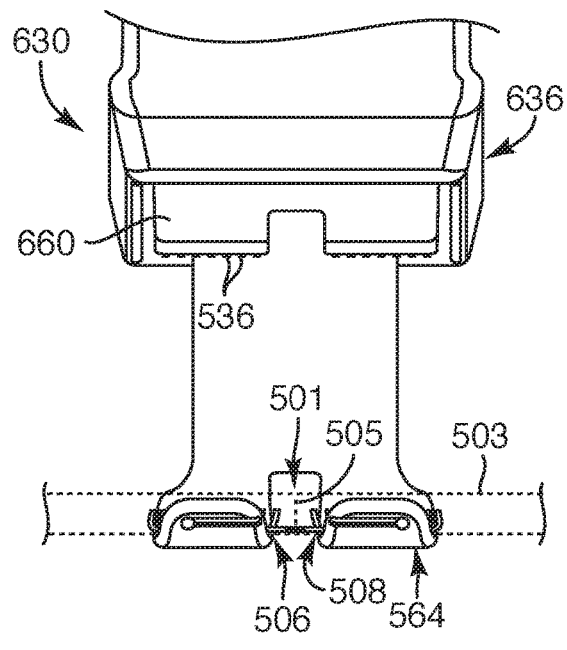
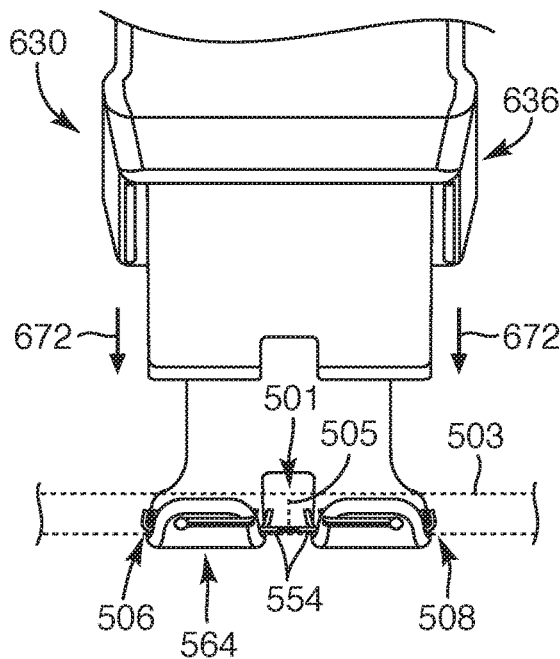
FIG. 53A    FIG. 53B
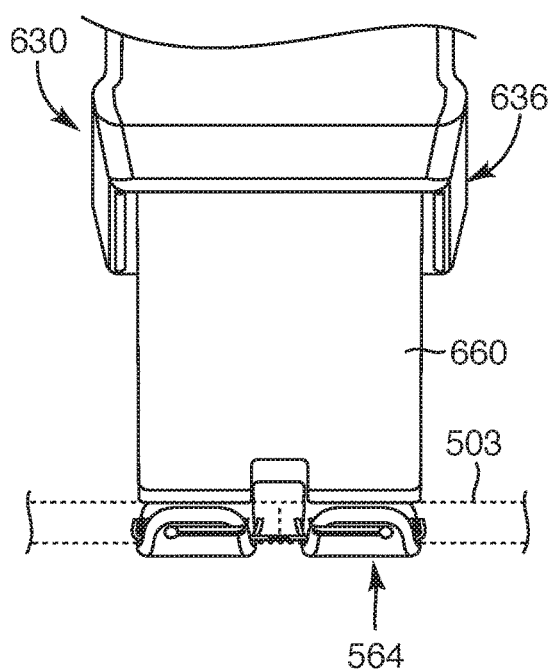
FIG. 53C

DEVICES, SYSTEMS, AND METHODS FOR REPAIRING SOFT TISSUE AND ATTACHING SOFT TISSUE TO BONE

CROSS-REFERENCE TO RELATED APPLICATIONS

The present application claims the benefit of U.S. Provisional Application No. 62/401,042, filed Sep. 28, 2016, the disclosure of which is hereby incorporated by reference herein in its entirety. The present application also claims the benefit, and is a continuation-in-part of U.S. patent application Ser. No. 14/885,959, filed Oct. 16, 2015, which claims the benefit of U.S. Provisional Application No. 62/215,739, filed Sep. 9, 2015, U.S. Provisional Application No. 62/129,742, filed Mar. 6, 2015, U.S. Provisional Application No. 62/094,032, filed Dec. 18, 2014, and U.S. Provisional Application No. 62/064,533, filed Oct. 16, 2014, the disclosures of each are hereby incorporated by reference herein in their entirety. Further, U.S. patent application Ser. No. 14/885,959 also claims the benefit, and is a continuation-in-part of, U.S. patent application Ser. No. 14/645,924, filed Mar. 12, 2015, now U.S. Pat. No. 9,629,632, which claims the benefit of U.S. Provisional Patent Application No. 62/053,056, filed Sep. 19, 2014, U.S. Provisional Patent Application No. 62/040,451, filed Aug. 22, 2014, U.S. Provisional Patent Application No. 62/007,783, filed Jun. 4, 2014, and U.S. Provisional Patent Application No. 61/952,114, filed Mar. 12, 2014, the disclosures of each are hereby incorporated by reference herein in their entirety. Further, the above-listed U.S. patent application Ser. No. 14/645,924 claims the benefit, and is a continuation-in-part of, U.S. patent application Ser. No. 13/953,709, filed Jul. 29, 2013, now U.S. Pat. No. 9,427,309, which claims the benefit of U.S. Provisional Patent Application No. 61/804,570, filed Mar. 22, 2013, and U.S. Provisional Patent Application No. 61/677,239, filed Jul. 30, 2012, the disclosures of each are hereby incorporated by reference herein in their entirety.

TECHNICAL FIELD

The present invention relates generally to soft tissue repair sites. More particularly, the present invention relates to devices, systems, and methods for repairing soft tissue and attaching soft tissue to bone.

BACKGROUND

Lacerated flexor tendon repair, as an example, is a procedure performed tens-of-thousands of times a year in the United States alone. For all types of tendons in the human anatomy, early post-operative mobilization is beneficial to restoring maximal tendon function following injury and repair. Adhesion formation is a common complication following tendon repair, but can be reduced through motion rehabilitation programs as soon as possible following a surgery. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

Typical procedures for lacerated tendon repair use one or more sutures to mend the two ends of a tendon together using complex suture patterns. While this can provide a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion. Further, complex suture patterns are also used for fixating soft tissue, such as tendon and ligaments, to bone, resulting in similar negative effects to the patient and often result in subsequent procedures depending on the activity level of the patient. Furthermore, such complex suturing procedures are time consuming and typically require specialized surgeons to perform such procedures.

BRIEF SUMMARY OF THE INVENTION

Embodiments of the present invention are directed to various devices, systems and methods for repairing soft tissue at a soft tissue repair site. For example, in one embodiment, a delivery device system for fixating a repair device to soft tissue at a soft tissue repair site is provided. The delivery device system includes an applicator assembly that includes a housing, a worm drive, a thumb wheel, a cartridge, and a finger element. The housing and the cradle may be fixed to each other. The worm drive is positioned within the housing. The thumb wheel is disposed around the worm drive such that the thumb wheel is configured to be rotated to linearly move the worm drive with threads defined in at least one of the worm drive and the thumb wheel. The cartridge is coupled to a distal end of the worm drive, the cartridge being configured to hold anchors of the repair device such that the cartridge is configured to be linearly moved relative to a bed surface of the cradle. The finger element extends from the worm drive and is configured to cooperate with an internal surface of the thumb wheel. With this arrangement, upon rotating the thumb wheel, the worm drive rotates with the finger element engaged with the internal surface of the thumb wheel.

In one embodiment, the internal surface of the thumb wheel defines multiple slots therein, the finger element sized to linearly translate along one slot of the slots as the worm drive rotates. In a further embodiment, upon the cartridge being linearly moved against the soft tissue positioned in the cradle, the finger element is configured to slip-out of the one slot to prevent further linear movement of the cartridge toward the bed surface of the cradle. In another embodiment, the finger element includes a circular member. In another embodiment, the finger element includes a ring structure. In a further embodiment, the finger element is fixed to the worm drive. In still a further embodiment, the finger element is positioned off-center relative to an axis of the worm drive.

In another embodiment, the finger element cooperates with the internal surface of the thumb wheel to limit a force applied to the soft tissue upon the cartridge being linearly moved against the soft tissue. In a further embodiment, the force applied to the soft tissue by a distal end of the cartridge is a function of a bendability of the finger element. In another embodiment, the finger element cooperates with the internal surface of the thumb wheel by linearly translating along a length of the internal surface of the thumb wheel and by slipping over a ratchet-like surface of the internal surface of the thumb wheel.

In another embodiment, the delivery device system further includes a firing mechanism operatively coupled to a proximal end of the worm drive. In a further embodiment, the firing mechanism includes a handle associated with a trigger, the handle and trigger sized and configured to manually deploy the repair device into the soft tissue. In another embodiment, the delivery devices system further includes a stroke regulator positioned between the firing mechanism and the worm drive. In an further embodiment, the stroke regulator includes an elastomer material.

In accordance with another embodiment of the present invention, a delivery device system for fixating a repair device to soft tissue at a soft tissue repair site is provided. The delivery device system includes a deployment mechanism, a housing, an anvil, a worm drive, a thumb wheel and a finger element. The deployment mechanism includes a handle associated with a trigger, the handle and trigger sized and configured to manually deploy the repair device into soft tissue with a push rod moveable along an axis. The push rod is linearly moveable by the deployment mechanism and extends distally from the deployment mechanism. The housing extends longitudinally along the push rod. The anvil and cartridge are configured to be coupled to the housing, the cartridge being at least partially holding the repair device. The worm drive is positioned within the housing. The thumb wheel is disposed around the worm drive, the thumb wheel being configured to be rotated to linearly move the worm drive with threads defined in at least one of the worm drive and the thumb wheel such that the worm drive is configured to linearly move the cartridge relative to a bed surface of the anvil. The finger element extends from the worm drive and is configured to cooperate with an internal surface of the thumb wheel. With this arrangement, upon rotating the thumb wheel, the worm drive rotates with the finger element engaged with the internal surface of the thumb wheel.

In one embodiment, the internal surface of the thumb wheel defines multiple slots therein, the finger element sized to linearly translate along one slot of the slots as the worm drive rotates. In a further embodiment, upon the cartridge being linearly moved against the soft tissue positioned in the anvil, the finger element is configured to slip-out of the one slot to prevent further linear movement of the cartridge toward the bed surface of the anvil. In another embodiment, the finger element includes a circular member. In still another embodiment, the finger element includes a ring structure.

In another embodiment, the delivery device system further includes a stroke regulator positioned between the deployment mechanism and the worm drive. In a further embodiment, the stroke regulator includes an elastomer material.

In accordance with another embodiment of the present invention, a delivery device system configured to move a cartridge with a repair device disposed therein toward an anvil with soft tissue positioned thereon for fixating the repair device to the soft tissue at a soft tissue repair site is provided. The delivery device system includes a housing, a worm drive, a thumb wheel and a finger element. The worm drive is at least partially positioned within the housing. The thumb wheel is disposed around the worm drive, the thumb wheel configured to be rotated to linearly move the worm drive with threads defined in at least one of the worm drive and the thumb wheel such that the worm drive is configured to linearly move the cartridge relative to a bed surface of the anvil. The finger element extends from the worm drive and is configured to cooperate with an internal surface of the thumb wheel. With this arrangement, upon rotating the thumb wheel, the worm drive rotates with the finger element engaged with the internal surface of the thumb wheel.

In one embodiment, the finger element includes or exhibits a circular member. In another embodiment, the finger element cooperates with the internal surface of the thumb wheel by linearly translating along a length of the internal surface of the thumb wheel such that the finger element limits a force of the cartridge being pushed against the soft tissue by the finger element slipping out of a slot defined in the internal surface of the thumb wheel.

In accordance with another embodiment of the present invention, a delivery system for fixating a repair device to soft tissue at a soft tissue repair site is provided. The delivery system includes a firing mechanism, an actuator member, and a device delivery portion. The actuator member is operatively coupled to the firing mechanism. The actuator member includes an actuation portion positioned within a tube structure, the tube structure having a finger holder positioned at a proximal portion of the tube structure and the actuation portion having a thumb holder positioned at a proximal portion of the actuation portion. The device delivery portion including a cartridge and a cradle, the cartridge slidable relative to the cradle. The cradle is configured to be fixed relative to the tube structure and the cartridge is configured to be coupled to the actuation portion of the actuation member. The device delivery portion is configured to hold the repair device. With this arrangement, linear movement of the actuation portion translates linear movement of the cartridge relative to the cradle.

In one embodiment, the tube structure includes indicia to determine a thickness of the soft tissue to be fixated. In another embodiment, the finger holder and the thumb holder facilitate manual actuation of the actuation portion. In another embodiment, the firing mechanism includes a handle associated with a lever for manually activating the firing mechanism. In another embodiment, the firing mechanism is activated with at least one of a manual lever, a hydraulic mechanism, and a pneumatic mechanism.

In accordance with another embodiment of the present invention, a repair device system for fixating soft tissue at a soft tissue repair site is provided. The repair device system includes a bed surface, a plate member, and an anchor. The bed surface of a delivery device defines anvil buckets therein. The plate member is positioned over the bed surface and configured to be positioned along an outer surface of the soft tissue. The anchor includes a base with at least four legs extending from the base, the base defining a longitudinal base axis with at least two legs extending from opposing sides of the base. The at least four legs configured to be forced against the anvil buckets to move the at least four legs to a curled configuration such that the at least four legs wrap around separate portions of the periphery of the plate member.

In one embodiment, adjacent legs of the at least two legs on a single side of the base of the anchor extend from the base at different distances relative to the longitudinal base axis. In another embodiment, adjacent legs extending from the base on a single side of the anchor extend from the base at different distances relative to the longitudinal base axis.

In another embodiment, a leg of the at least four legs includes one or more tapers along the length thereof sized and configured to facilitate the legs to move to the curled configuration. In another embodiment, a leg of the at least four legs includes a taper extending with an angle between about 1 degree and 10 degrees. In another embodiment, the anchor includes six legs each configured to be forced against the anvil buckets to move the six legs to a curled configuration such that the six legs wrap around separate portions of the plate member.

In accordance with another embodiment of the present invention, a method for repairing soft tissue is provided. The method includes providing a delivery device with a cartridge and an anvil, the cartridge holding one or more anchors, each anchor having a base portion and at least four legs extending from the base portion, the anvil defining a bed surface sized to receive one or more plate members; positioning soft tissue over the one or more plate members positioned on the bed surface such that the soft tissue is positioned between the one or more plate members and the one or more anchors; and forcing the one or more anchors from the cartridge with the delivery device so that the at least four legs extend through the soft tissue and are compressed against anvil buckets defined in the bed surface to force the at least four legs of each anchor to curl around separate portions of one of the one or more plate members so that the base portion of the one or more anchors is positioned over an opposite side of the soft tissue relative to the one or plate members.

In one embodiment, the step of forcing includes forcing the anchors toward the anvil in a direction parallel to a delivery device axis such that the bed surface of the anvil extends longitudinally to define an anvil axis, the anvil axis being substantially perpendicular to the delivery device axis. In another embodiment, the step of positioning includes positioning the soft tissue over a first plate member of the one or more plate members and positioning soft tissue over a second plate member of the one or more plate members such that the first and second plate members are longitudinally aligned within the bed surface of the anvil. In still another embodiment, the step of forcing includes forcing a first anchor and a second anchor of the one or more anchors so that the at least four legs of each of the first and second anchors extend through the soft tissue and curl around separate portions of the respective first and second plate members.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 4 is a front view of one of the anchors for the soft tissue repair device of FIG. 1, according to another embodiment of the present invention;

FIG. 4A is a perspective view of the anchor of FIG. 4, according to the present invention;

FIG. 5 is a perspective view of another embodiment of one of the anchors for the soft tissue repair device of FIG. 1, according to the present invention;

FIG. 8 is a perspective view of an upper rigid substrate, the upper rigid substrate being a component of a soft tissue repair device, according to another embodiment of the present invention;

FIG. 9 is a perspective view of a rigid member, the rigid member being a component of a soft tissue repair device, according to another embodiment of the present invention;

FIG. 10 is a side view of a repair device, depicting the repair device fixating soft tissue to bone, according to another embodiment of the present invention;

FIG. 11A is a top cross-sectional view taken above the lower substrate, depicting an anchor relative to anvil beds, according to another embodiment of the present invention;

FIG. 11B is a side view of the repair device system, depicting the anchor fixating tissue with the upper and lower substrates, according to another embodiment of the present invention;

FIG. 12 is a side view of the repair device system, depicting the repair device system fixating soft tissue to bone, according to another embodiment of the present invention;

FIG. 13 is a simplified perspective view of another embodiment of a flexible member integrated with multiple anchors, the flexible member being a component of a repair device, according to the present invention;

FIG. 14 is a simplified perspective view of a flexible wrap member, the flexible wrap member being a component of a repair device and sized to surround soft tissue and a soft tissue repair site, according to another embodiment of the present invention;

FIG. 14A is a cross-sectional view of the flexible wrap member, according to another embodiment of the present invention;

FIG. 15 is a side view of a repair device, depicting the repair device with the flexible wrap surrounding soft tissue and positioned between anchors and the rigid member, according to another embodiment of the present invention;

FIG. 26 is a perspective view of the repair device, depicting the alignment of legs of the first and second anchors corresponding with notches and openings of the first and second plate members;

FIG. 27 is a top view of a bed surface of a cradle portion, according to another embodiment of the present invention;

FIG. 27A is a partial top view of the bed surface of the cradle portion with the first plate member positioned over the bed surface of the cradle portion, according to another embodiment of the present invention;

FIG. 53A is a partial top view of the delivery device, depicting severed soft tissue positioned over the cradle portion of the delivery device, according to another embodiment of the present invention;

FIG. 53B is a partial top view of the delivery device, depicting a cartridge being moved toward the cradle portion of the delivery device, according to another embodiment of the present invention;

FIG. 53C is a partial top view of the delivery device, depicting the cartridge moved adjacent the cradle portion to a position prior to fixating the severed soft tissue, according to another embodiment of the present invention;

DETAILED DESCRIPTION OF THE INVENTION

Various embodiments are disclosed herein of a soft tissue repair device. Such repair device may be sized and configured to approximate and fuse, for example, a lacerated tendon. The various embodiments may provide structure that maintains two ends of a lacerated tendon in an abutting relationship, without gapping, while allowing the tendon adjacent the tendon ends and along the length of the repair device to provide controlled elongation of the tendon. In this manner, the repair device of the present invention may provide the proper healing required for fusing the tendon ends while still providing movement of the tendon to minimize atrophy and potential adhesions.

Figure 1:
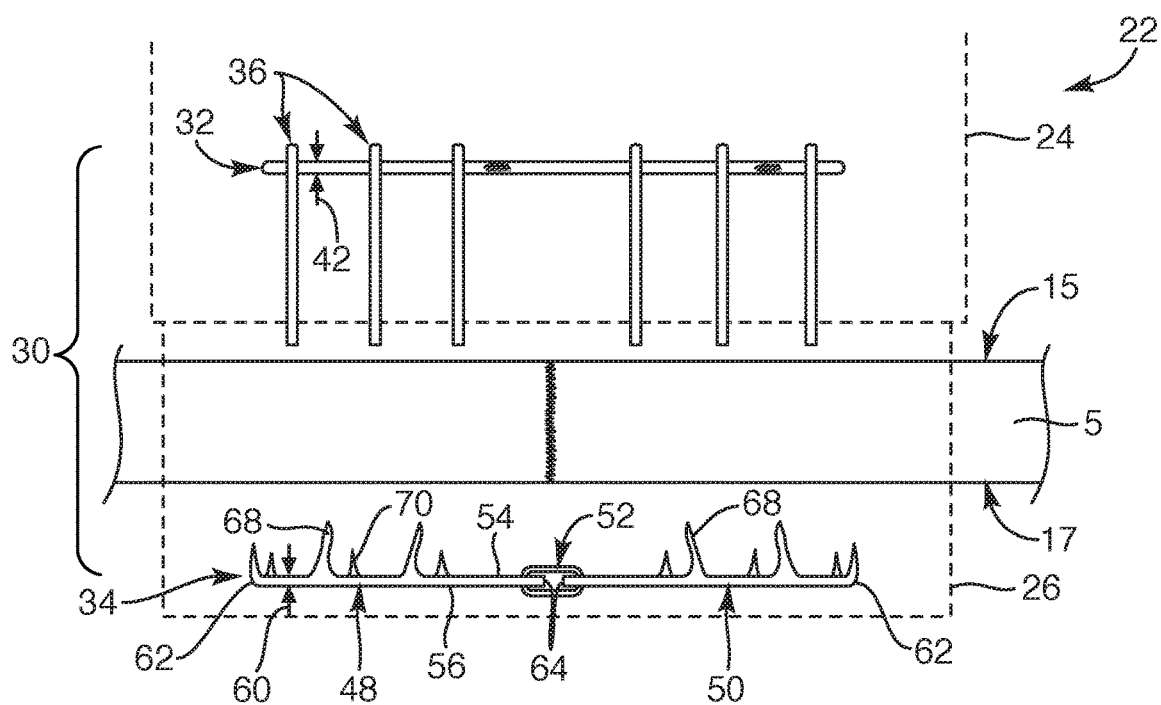
FIG. 1 is a side view of one embodiment of a soft tissue repair device with a portion of the delivery device in outline form, depicting the soft tissue repair device with one or more rigid members positioned opposite a flexible member and anchors in a pre-deployed state, according to the present invention.

With reference to FIG. 1, one embodiment of a repair device 30, shown in a pre-deployed state, is provided. The repair device 30 may include a flexible member 32 and one or more rigid members 24 that may be coupled together with anchors 36. The flexible member 32 may be positioned relative to separate and discrete anchors 36 in a pre-deployed state within a cartridge 24 (generally shown in outline form) integrated with a delivery device 22. The delivery device and cartridge arrangement (and other delivery device and system components) may be similar to that described in commonly owned U.S. Non-Provisional patent application Ser. No. 14/645,924, the disclosure of which is incorporated by reference herein in its entirety, the disclosure describing in detail a delivery device that may be employed with the repair device of this embodiment. As set forth, in this embodiment, the repair device 30 may include one or more rigid members 34 positioned oppositely from the flexible member 32 and positioned within a cradle portion 26 (shown in outline) of the delivery device 22. For example, for tendons in the hand, such as in zone two of the hand anatomy, the flexible member 32 may be positioned over a palmar side 15 of the tendon 5 and the one or more rigid members 34 may be positioned over (or under) a dorsal side 17 of the tendon 5. In this manner, while the repair device 30 is in a pre-deployed state, the flexible member 32 and the one or more rigid members 34 may be positioned in a generally parallel arrangement with the anchors 36 suspended within the cartridge 24 positioned perpendicular relative to the flexible member 32.

Figure 2:
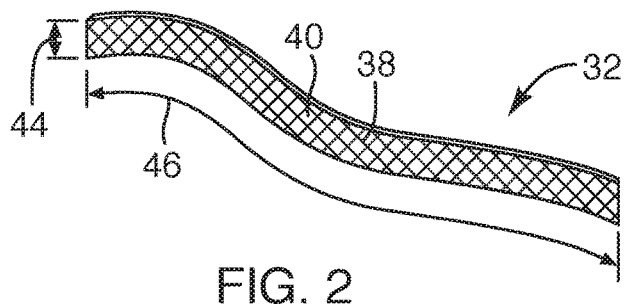
FIG. 2 is a perspective view of the flexible member of the soft tissue repair device of FIG. 1, according to another embodiment of the present invention.

With reference to FIG. 2, further to the various embodiments described in the above-noted U.S. Provisional Patent Applications for the flexible member 32 or ribbon, the flexible member 32 may be a filamentary member. Further, in one embodiment, the flexible member 32 may be sized and configured with one or more filaments 38 so as to include multiple pores 40. Although simplistically depicted, the filaments 38 may extend in a manner so as to be inter-woven, braided, and/or knitted, or the like to define the pores 40 between adjacently extending filaments 38. The pores 40 may include a pore size in the range of about 50-250 microns. In another embodiment, the flexible member 32 may be a monolithic structure defining a multi-cellular structure. In one embodiment, the monolithic structure may define pores 40 with the pore size in the range of about 50-250 microns. In another embodiment, the flexible member 32 may be a healing ingrowth substrate. For example, the pores 40 of the flexible member 32 may be sized and configured to induce tissue ingrowth therethrough such that, upon the occurrence of a gap or gap widening between the severed tendon 5 (FIG. 1), the flexible member 32 and its pores 40 facilitate tissue ingrowth across the gap and through the flexible member 32 so as to bridge the gap and assist in filling a potential gap.

With respect to FIGS. 1 and 2, the flexible member 32 may be an elongate member that may include a depth 42, a width 44, and a length 46. The length 46 of the flexible member 32 corresponds with the longitudinal dimension of the elongate member. The width 44 is smaller than the length 46 and extends perpendicular to the length dimension and in a common plane as the length dimension. The depth 42 is a thickness of the flexible member 32 and extends perpendicular to the dimensions of the length 46 and width 44.

Figure 3:
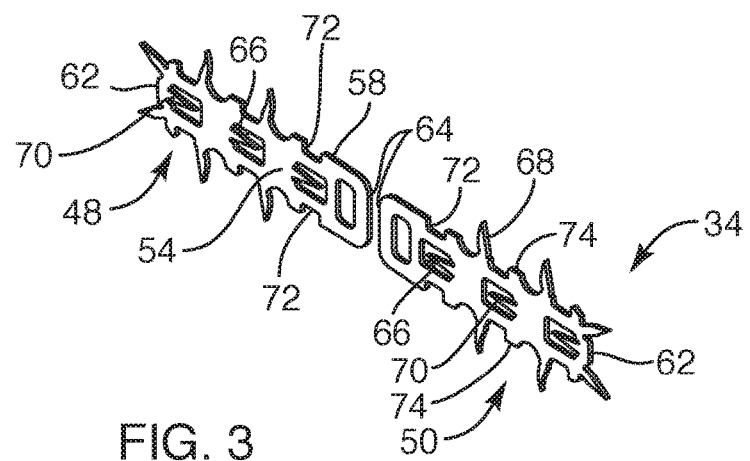
FIG. 3 is a perspective view of the one or more rigid members of FIG. 1, depicting the one or more rigid members in a pre-formed flat state, according to another embodiment of the present invention.

With respect to FIGS. 1 and 3, the one or more rigid members 34 will now be described. As set forth, the one or more rigid members 34 may be positioned within a bed surface 28 of the cradle portion 26 (see FIG. 7) and be positioned parallel to the flexible member 32. The one or more rigid members 34 may be a single rigid member or multiple rigid members, such as two, three, or four rigid members or more. As depicted in this example, the one or more rigid members 34 may include two rigid members, such as a first rigid member 48 and a second rigid member 50. The first and second rigid members 48, 50 may be coupled with a coupling structure 52. The coupling structure 52 may be in the form of one or more filament structures or the like that are flexible so as to facilitate the first and second rigid members 48, 50 to be moveable to different orientations relative to each other, upon the repair device 30 being secured to a severed tendon 5 or the like, but also substantially resist separation of the rigid members such that the coupling structure 52 resists elongation. In the event three rigid members 34 or more are employed, such rigid members may be shortened (or maintain a similar length) and interconnected with multiple flexible coupling structures.

The first and second rigid members 48, 50 each may be generally flat structures and elongated. For example, the first and second rigid members 48, 50 may be formed from a flat sheet of material via laser cutting or the like, as depicted in FIG. 3. As such, each of the first and second rigid members 48, 50 may include and define an inner surface 54 and outer surface 56, the inner and outer surfaces 54, 56 defined with a periphery 58 having a depth 60 or thickness. Further, the first and second rigid members 48, 50 may be positioned and oriented to include an outer end 62 and an inner end 64, the inner ends 64 positioned adjacent each other and coupled with the coupling structure 52. Furthermore, each of the first and second rigid members 48, 50 may define multiple openings 66 defined therein such that the first and second rigid members 48, 50 may be a multi-cellular structure.

In one embodiment, the first and second rigid members 48, 50 may include multiple tines. Such multiple tines may be initially cut in a common plane, as depicted in FIG. 3, and bent and formed to an upright position, as depicted in FIG. 1. The multiple tines may include peripheral tines 68 and central tines 70 such that each of the multiple tines may be formed to extend from the inner surface 54. The peripheral tines 68 may extend from opposing sides 74 and outer ends 62 of the first and second rigid members 48, 50. Further, the peripheral tines 68 may extend substantially perpendicular relative to the inner surface 54 and/or the peripheral tines 68 may extend in a canted manner toward the respective inner ends 64 of the first and second rigid members 48, 50. The central tines 70 may extend from at least some of the openings 66 defined in each of the first and second rigid members 48, 50 and, further, the central tines 70 may extend perpendicularly and/or canted relative to the inner surface 54 of the first and second rigid members 48, 50. Such peripheral and central tines 68, 70 may be sized and configured to engage and extend into soft tissue.

In another embodiment, each of the first and second rigid members 48, 50 may include opposing notches 72 defined in the periphery 58 and along the opposing sides 74 of the first and second rigid members 48, 50. Each of the opposing notches 72 may be defined adjacent to and on the opposite sides 74 of one of the openings 66 defined in the first and second rigid members 48, 50. In other words, each of the opposing notches 72 includes one of the openings 66 therebetween. With this arrangement, each of the opposing notches 72 and its corresponding opening 66 may be sized and configured to receive first and second legs 78, 80 (see FIG. 6B) of the anchors 36 for securing the flexible member 32 and rigid members 34 to the severed tendon 5, discussed in further detail herein. Further, the first and second rigid members 48, 50 may be formed from a metallic material, such as stainless steel, titanium, or Nitinol, or any other suitable material or combinations of materials.

Now with reference to FIGS. 1 and 4, a detailed view of one of the anchors 36 of the repair device 30 is provided. The anchors 36 may include a generally u-shaped configuration with an upper portion 76 having a first leg 78 and a second leg 80 extending from opposite ends of the upper portion 76. The upper portion 76 may also include a tine 82 or center tine extending from the upper portion 76 such that the tine 82 extends parallel with and between the first and second legs 78, 80 in a common direction of the legs. Further, the upper portion 76 may define a spacing 84 between the first and second legs 78, 80. Such spacing 84 between the first and second legs 78, 80 may be sized and configured to position the flexible member 32 within the spacing 84 with the tine 82 configured to extend through the flexible member 32 (shown in outline), such that the width 44 (FIG. 52) of the flexible member 32 may be sized smaller or about the same as the spacing 84.

With respect to FIGS. 4 and 4A, in one embodiment, each of the first and second legs 78, 80 may include portions that taper along their length toward free ends 86 of the first and second legs 78, 80. In other words, the first and second legs 78, 80 may include varying widths along their lengths. In another embodiment, the first leg 78 and the second leg 80 may each include a first width 88 that extends from the upper portion 76 along a first length 90, then tapers with a first taper 92 to extend to a second width 94 that extends along a second length 96, then again tapers with a second taper 98 to the free ends 86 of the first and second legs 78, 80. The second width 94 may be smaller than the first width 88. Further, the second length 96 of each of the first and second legs 78, 80 may be greater than the first length 90. In another embodiment, the second length 96 of each of the first and second legs 78, 80 may slightly taper toward distal ends 100 of the second length 96. In another embodiment, the first and second legs 78, 80 extend from the upper portion 76 such that the spacing 84 of the first and second legs 78, 80 increases from the upper portion 76 to the distal end 100 of the second length 96 of the first and second legs 78, 80 and, along the second taper 98, the spacing 84 may be substantially constant such that an outer surface 102 of the first and second legs 78, 80 along the second taper 98 extends inward to form the second taper 98. Such tapers along the length of the first and second legs 78, 80 may be sized and configured to facilitate the legs to wrap and curl in a controlled manner, upon being deployed and secured to the above-described one or more rigid members 34, as depicted in FIG. 6B.

With reference to FIG. 5, another embodiment of an anchor 104 that may be employed with the repair device 30 of FIG. 1 is provided. In this embodiment, the anchor 104 is substantially the same as the anchor in FIG. 4, except in this embodiment, the anchor 104 may include two tines 108 or two center tines, each of the two tines extending from an upper portion 106 of the anchor 104. The two tines 108 may extend substantially along with and parallel with legs 110 of the anchor 104 and may be sized and configured to extend through the flexible member 34 and into the soft tissue to which the anchor 104 is secured, similar to that depicted in FIG. 6B.

Figure 6:
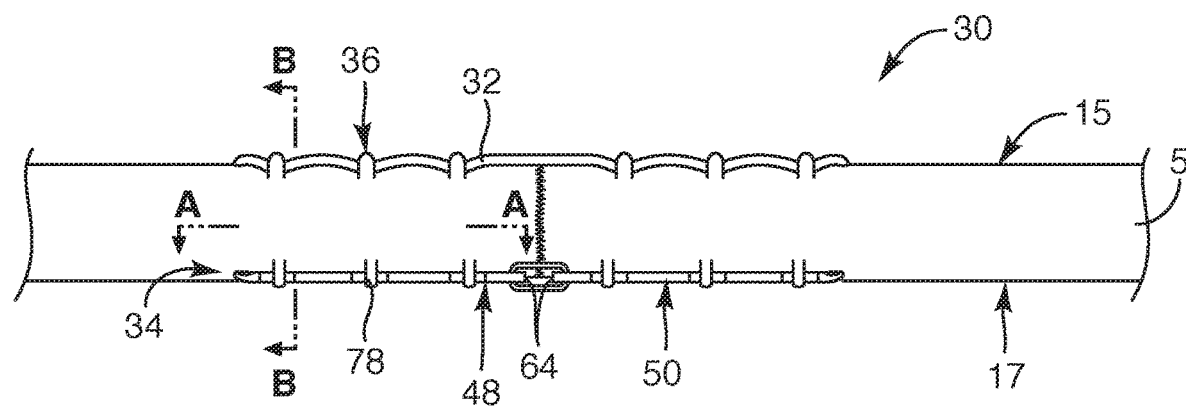
FIG. 6 is a side view of the soft tissue repair device in a deployed state, according to another embodiment of the present invention.
Figure 6A:
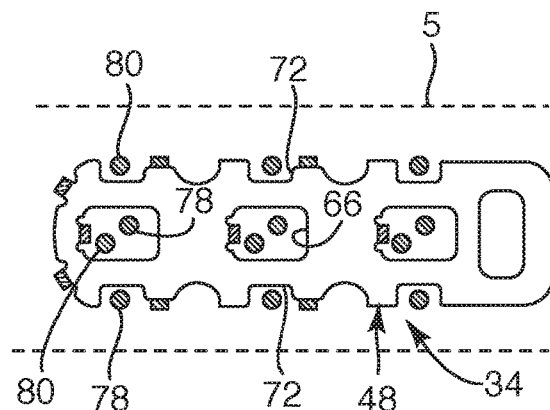
FIG. 6A is a cross-sectional view of the soft tissue repair device taken along section line A-A in FIG. 6, according to another embodiment of the present invention.

Now with reference to FIGS. 1 and 6, as depicted, the repair device 30 may be deployed for fixating and fusing together, for example, a severed tendon 5. As in previous embodiments, the severed tendon 5 may be placed over the cradle portion 26 of the delivery device 22. Further, as set forth, this embodiment includes the first and second rigid members 48, 50, which are each positioned over the cradle portion 26 with the peripheral and central tines 68, 70 extending upward such that the severed tendon 5 may be placed over the rigid members 34 with the severed portion positioned over and between the inner ends 64 of the first and second rigid members 48, 50. The peripheral tines 68 and the central tines 70 may each be sized and configured to pierce the underside surface or dorsal side 17 of the severed tendon 5.

Figure 6B:
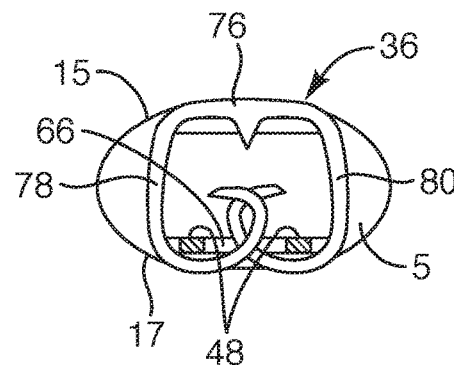
FIG. 6B is a cross-sectional view of the soft tissue repair device taken along section line B-B in FIG. 6, according to another embodiment of the present invention.

With respect to FIGS. 1, 6 and 6B, the physician may trigger or actuate the delivery device 22, which forces the first and second legs 78, 80 of the anchors 36 to extend through the flexible member 32 and anchor to the severed tendon 5 with the upper portion 76 of the anchors 36 sandwiching the flexible member 32 against the upper side or palmar side 15 of the severed tendon 5. Further, the first and second legs 78, 80 of each of the anchors 36 are sized and configured to wrap around the first and second rigid members 48, 50 so that the tendon 5 is positioned between the rigid members 34 and the flexible member 32.

Figure 7:
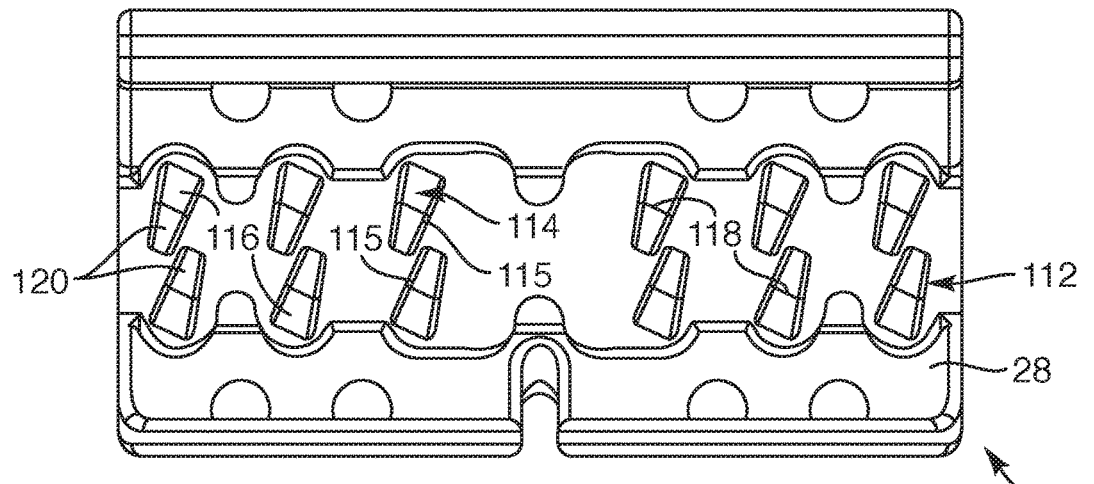
FIG. 7 is a top view of a cradle portion of the delivery device, depicting canted anvil buckets in a bed surface of the cradle portion, according to another embodiment of the present invention.

With respect to FIGS. 6, 6A, 6B and 7, additional description of the anchors 36 coupling to both the flexible member 32 and the first and second rigid members 48, 50 are provided. Initially, upon triggering the delivery device 22 (FIG. 1), the first and second legs 78, 80 of each of the anchors 36 may be forced to extend through the tendon 5 and then continue to extend through the opposing notches 72 of the first and second rigid members 48, 50. Once through the opposing notches 72, the first and second legs 78, 80 may then be forced against canted anvil buckets 112 defined in a bed surface 28 of the cradle portion 26 (as shown in FIG. 7). The canted anvil buckets 112 may include a bucket surface 114 with and defining a downward slope 116 extending to a bottom 118 and then extending along an upward slope 120. The orientation of the canted anvil buckets 112, an upstanding wall 115 (or functional wall), as well as the above-indicated slopes of the bucket surface 114, force the first and second legs 78, 80 of the anchors 36 to bend toward each other and follow the canted anvil bucket 112 orientation so that the legs curl past each other and loop through the opening 66 between the corresponding opposing notches 72 in an over lapping manner, as depicted in FIG. 6B. The upstanding wall 115 of the anvil buckets 112 provides a functional wall to guide and direct the respective legs to precise over lapping orientations. In this manner, the first and second legs 78, 80 of each of the anchors 36 wrap around one of the first and second rigid members 48, 50 to secure the rigid members 34 and the flexible member 32 to the severed tendon 5. Further, the first and second rigid members 48, 50 stabilize the anchors 36 so that the upper portion 76 of the anchors 36 synchs against the flexible member 32 so as to provide a quilting effect relative to the flexible member 32.

With respect to FIG. 8, another embodiment of a component of a repair device is provided. In this embodiment, rather than employing the above-described flexible member, as set forth in previous embodiments herein, the repair device may include an upper plate member 122. As such, the repair device of this embodiment may include similar components set forth in the previous embodiment described relative to FIG. 1, but includes the upper plate member 122, rather than the flexible member. The upper plate member 122 may be a single elongated member that may be generally flat, as depicted in its cut form from sheet material. The upper plate member 122 may be a rigid structure and may include multiple openings 124 defined therein. The openings 124 may be sized and configured to receive, for example, the tine 82 (FIG. 4) of the anchors 36. Further, the upper plate member 122 may include upper peripheral tines 126 that may be formed to a bent position (not shown) to extend generally perpendicular and/or canted relative to an inner surface 858 of the upper plate member 122. Such upper peripheral tines 126 may be sized and configured to be forced into the soft tissue upon anchors 36 (upper portion 76 in FIG. 4) being forced against an outer surface 130 of the upper plate member 122. Further, the canted orientation of the upper peripheral tines 126 may be canted toward a center portion 132 of the upper plate member 122 so as to assist in maintaining the severed tendon together.

With respect to FIG. 9, another embodiment of a component of a repair device is provided. In this embodiment, rather than first and second rigid members, as described in previous embodiments, the repair device includes an elongated single rigid member 134. This embodiment may include similar features and structural characteristics as the before-described first and second rigid members 48, 50 (FIG. 3) to facilitate the anchors 36 (FIG. 4) to wrap around opposing notches 136 and curl through openings 138 defined between the opposing notches 136. In one embodiment, the single rigid member 134 may be more suitably employed for soft tissue in other anatomical areas than zone two in the hand anatomy. For example, the upper plate member 122 and single rigid member 134, depicted in FIGS. 8 and 9, may be better suited for tendons at the ankle, the knee, and shoulder, or any other tendons or soft tissue in the body where the location of the severed tendon does not require the tendon to move over a radius.

In another embodiment, with respect to FIG. 10, a repair device 140 similar to the repair device described in previous embodiments may be utilized to fixate a tendon 5 (or any soft tissue) to bone 19. For example, the repair device 140 may include a lower rigid member 142, such as the first rigid member 48 of FIG. 3, and an upper substrate 144 with anchors 36 sized and configured to sandwich a tendon 5 between the upper substrate 144 and the lower rigid member 142. In one embodiment, the upper substrate 144 may be similar to the upper plate member 122 of FIG. 8, but sized to correspond with the lower rigid member 142. In another embodiment, the upper substrate 144 may be the flexible member 132, similar to previous embodiments described herein, sized and configured to correspond with the lower rigid member 142. The anchors 36 may be positioned and attached to the tendon 5 so as to wrap and curl through openings defined in the lower rigid member 142, similar to that depicted in FIG. 6B.

The repair device 140 may also include a filament 146 sized and configured to couple to a bone anchor 148. The filament 146 may include a coupling portion 150 and an attachment portion 152. Further, the filament 146 may be flexible and sized and configured to adapt for attachment to most any suitable bone anchor 148. The coupling portion 150 of the filament 146 may couple to an opening 154 defined in the upper substrate 144 and the attachment portion 152 may include a loop that may be synched or attached to the bone anchor 148. The filament 146 may be in the form of a wire or suture and may be a metallic material or a polymeric material or any other suitable material known in the art. Further, as depicted, the bone anchor 148 may include a bone screw shaft 156 or the like and may include a bone screw insert 158. The bone screw insert 158 may be inserted and positioned within a pre-formed hole 21 in the bone 19 and may include tines 160 to assist in preventing migration from the bone 19. In another embodiment, the bone screw insert 158 may be inserted within the hole 21 with adhesive to secure the bone screw insert 888 within the bone 19. The bone screw insert 158 may also include threads on an inner surface thereof that correspond with threads of the bone screw shaft 156. The bone screw shaft 156 may also include a screw head 162 that may act to maintain the attachment portion 152 of the filament 146 as well as facilitate the physician to insert and remove the bone screw shaft 156, as indicated by arrow 164. In this manner, a repair device 140, having similar structural features of the repair devices described in the various embodiments herein, may be employed for fixating tendon 5 (or any soft tissue) to bone 19.

Figure 11:
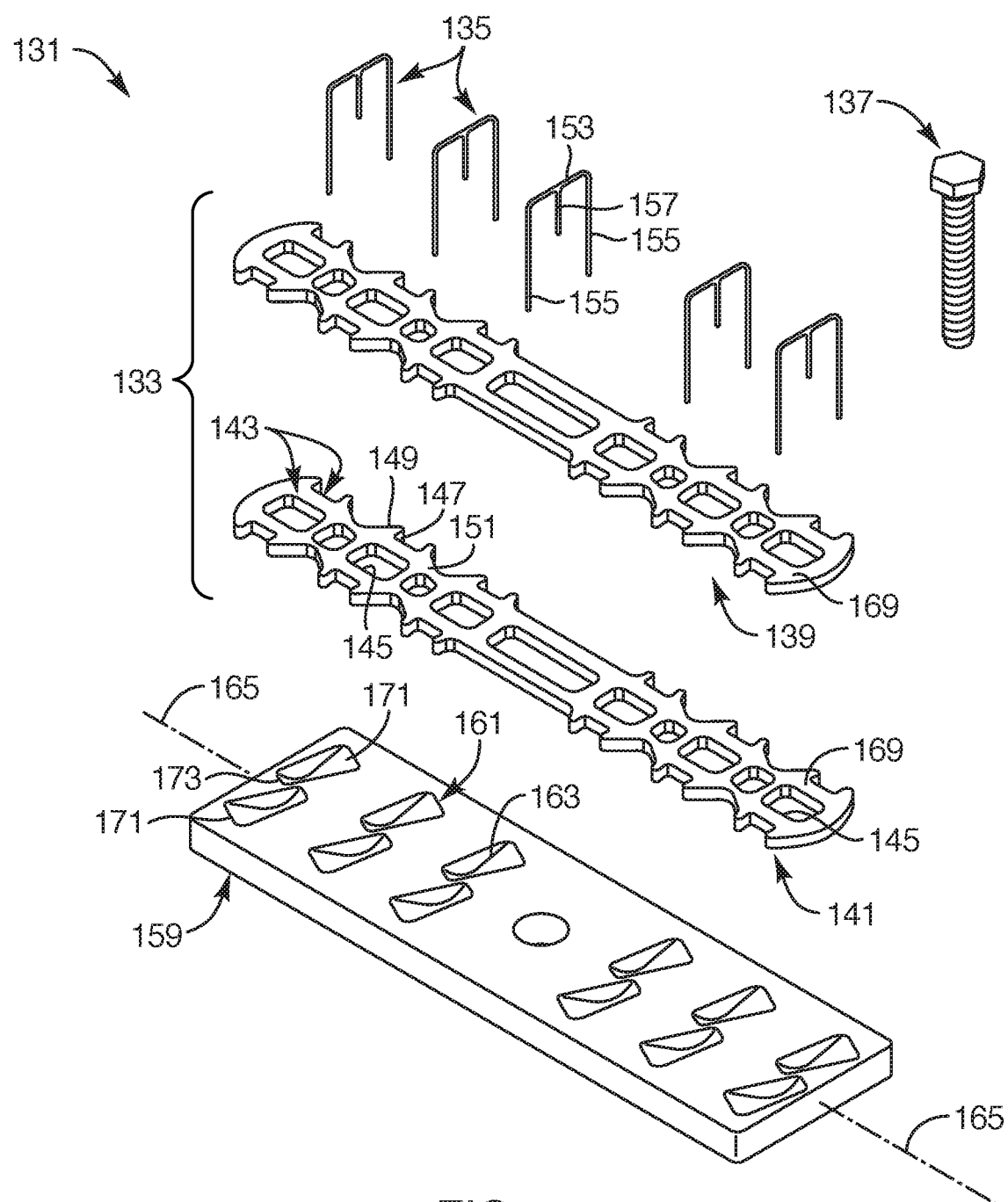
FIG. 11 is an exploded view of another embodiment of a repair device system, depicting upper and lower substrates, anchors, a bone anchor, and an anvil, according to the present invention.

With respect to FIG. 11, another embodiment of a repair device system 131 for fixating soft tissue 5 to bone 19 is provided. Similar to the previous embodiments for fixating soft tissue to bone, the repair device system 131 may include a carrier member 133, multiple anchors 135, and one or more bone anchors 137. In this embodiment, the carrier member 133 may include upper pad portions 139 and lower pad portions 141 (or upper and lower substrates/carrier members), the upper pad portions 139 being separate and discrete from the lower pad portions 141. Each of the upper and lower pad portions 139, 141 may be a substantially flat structure. Further, each of the upper and lower pad portions 139, 141 may be a multi-cellular structure that may be seamless and monolithic (single piece).

As in the previous embodiments, each pad portion of the upper and lower pad portions 139, 141 may include one or more slots 143, the slots 143 being defined as apertures, holes, and/or notches. For example, the slots 143 defined in a given pad portion may include a central slot 145 and opposing side slots 147, the opposing side slots 147 being similar to a notch formed in opposing peripheral sides 149 of the pad portion. Each pad portion of the respective upper and lower pad portions 139, 141 may be interconnected to an adjacent pad portion with struts 151. Further, the central slot 145 and side slots 147 are sized and configured to receive portions of the anchors 135. The anchors 135 may be u-shaped with a mid-upper portion 153 and legs 155 extending from the mid-upper portion 153. Further, the anchors 135 may each include a tine 157 extending downward between the legs 155 and within a common plane of the legs 155.

The anchors 135 may be manipulated to engage the upper and lower pad portions 139, 142 with the soft tissue 5 therebetween, as depicted in FIGS. 11A and 11B, with an anvil 159 depicted in FIG. 11. The anvil 159 may include multiple anvil beds 161 defined therein. Each anvil bed 161 may extend from an outer end 171 to and inner end 173 with a downward slope from the outer end 171 to a ramp toward the inner end 173 of the anvil bed 161. Further, each anvil bed 161 may define a groove 163 (FIG. 11) therein to capture ends of the legs 155 and manipulate them through a precise orientation. In this manner, each anvil bed 161 extends with a radial component sized and configured to curl the legs 155 of the anchors 135. Further, in another embodiment, each anvil bed 161 may be canted relative to a longitudinal axis 165 of the anvil 159. As such, the legs 155 of the anchor 135 may be manipulated to curl and pass by each other in an over-lapping manner or side-by-side, as depicted in FIGS. 11A and 11B. With this arrangement, legs 155 of the anchor 135 may extend alongside opposing side slots 147 of the upper and lower pad portions 139, 141 and curl around a bottom surface 167 of the lower pad portions 141 and through the central slot 145 of the lower pad portions 141. Further, as depicted, each pair of the canted anvil beds 161 manipulate the legs 155 of each anchor 135 to pass through the central slot 145 so that the legs 155 grab and bundle a portion of the soft tissue 5 in a side-by-side manner. Further, the groove 163 (FIG. 11) in each anvil bed 161 facilitates a pre-determined curl in the legs 155 of the anchors 135. Such anchors 135 and carrier member 133 may be secured to the soft tissue 5 with, for example, a delivery tool having an anchor cartridge (not shown) coupled to the anvil 159.

With reference to FIGS. 11 and 12, upon the anchors 135 securing the carrier member 133 to the soft tissue 5, the bone anchor 137, such as a bone screw or the like, may be inserted through, for example, the central slot 145 adjacent one end of each of the upper and lower pad portions 139, 141 and then into a pre-drilled hole in the bone 19. In one embodiment, the carrier member 133 may include a bone engaging portion 169 such that the pad portion at one common end of each of the upper and lower pad portions 139, 141 acts as the bone engaging portion 169. As such, in this embodiment, the central slot 145 at the one end of the upper and lower pad portions 139, 141 may act as the hole defined in the bone engaging portion 169 of the carrier member 133. In another embodiment, the bone engaging portion 169 may be an extension from the upper and lower pad portions 139, 141, similar to the extended bone engaging portion of FIG. 10

With respect to FIG. 13, another embodiment of a flexible member 170 coupled to multiple anchors 172 is provided. Such flexible member 170 and anchor 172 arrangement of this embodiment may be employed as a component or portion to be added or replace the flexible member/anchor arrangement of the various repair devices set forth herein. The flexible member in this embodiment may be one or more filaments configured to be integrated with the anchors 172, the anchors shown simplistically with two tines 174 extending from the intermediate portion 176 and between the first and second legs 178, 180. For example, in one embodiment, the anchors 172 may be the same or similar to the anchor depicted in FIG. 5.

In this embodiment, the flexible member 170 having the one or more filaments may be a single filament 182. The single filament 182 may be systematically wrapped around the anchors 172 in a manner that couples each of the anchors 172 together. Further, for simplistic purposes, the filament 182 is depicted as wrapping around the anchors 172 with fewer rotations than that which the single filament is preferably wrapped around the anchors. For example, the filament 182 may be wrapped around pairs or sets of the anchors 172 with two, three or more rotations and, preferably, the anchors 172 may be wrapped with at least five rotations or wraps around the pairs or sets of anchors.

In one embodiment, the filament 182 may be wrapped around the intermediate portion 176 of the anchors 172 and between the two tines 174 of each of the anchors 172. One method for wrapping the filament 182 around the anchors 172 may include systematically wrapping the pairs or sets of anchors 172 beginning at inner adjacent anchors 184 and then wrapping around other anchors 172 adjacent and outward the inner adjacent anchors 184. As depicted, the anchors 172, in one example, may include a first anchor 186, a second anchor 188, a third anchor 190, a fourth anchor 192, a fifth anchor 194, and a sixth anchor 196. The filament 182 may first be wrapped around the intermediate portion 176 and between the two tines 174 of the inner adjacent anchors 184 or third and fourth anchors 190, 192. The filament 182 may then further be wrapped around a first anchor set 198 or the second and fifth anchors 188, 194 while also wrapping over the third and fourth anchors 190, 192. The filament 182 may then continue and be further wrapped around the intermediate portion 176 between the two tines 174 of a second anchor set 200 or the first and sixth anchor 186, 196, while also wrapping around the other anchors 172.

In one embodiment, the wraps around the third and fourth anchors 190, 192, the second and fifth anchors 188, 194, and the first and sixth anchors 186, 196 may include five rotations or wraps of the filament 182. In another embodiment, in the wrapping process and upon first arriving to a given anchor, the wrapping of the anchors 172 may include wrapping the filament 182 completely around each intermediate portion 176 of a given anchor before continuing the wrapping of a given pair or set of anchors 172. In still another embodiment, upon completing the wraps of the anchors 172, the fourth, fifth, and sixth anchors 192, 194, 196 may be simultaneously rotated, as indicated by arrow 202, with one or more rotations so as to result in a twist in the filament between the third and fourth anchors 190, 192. In this manner, the flexible member 170 may be employed with the single filament 182 integrated with the anchors 172, the flexible member 170 and anchor 172 arrangement to be employed as a component of a repair device of any one of the various embodiments set forth herein.

In one embodiment, the filament 182 may be a polymeric filament or a polymeric fiber. The polymeric filament or fiber may be a polyethylene material, such as ultra-high-molecular-weight polyethylene ("UHMWPE"), a polyester material, a polypropylene material, or the like. In another embodiment, the polymeric filament or fiber may be a bioresorbable material, such as polylactide ("PLA"), polycaprolactone ("PCL"), polydioxanone ("PDX"), or the like, or any other suitable bioresorbable material as known to one of ordinary skill in the art. Such a single filament or fiber may include a woven, braided, or a single strand configuration.

With respect to FIGS. 14 and 14A, a flexible wrap member 204 as a component or portion of a repair device, according to another embodiment of the present invention, is provided. The flexible wrap member 204 may be sized and configured to be wrapped around the soft tissue 5 prior to receiving the remaining portions of a repair device, described in further detail hereafter. The flexible wrap member 204 may also be positioned to surround and wrap over the soft tissue repair site. The flexible wrap member 204 is flexible and may be readily manipulated to wrap around the soft tissue, as indicated by arrows 206.

The flexible wrap member 204 may include an inner surface 208 and an outer surface 210 defined by a periphery 212 having a depth 214. Further, the flexible wrap member 204 may include a length 216 and a width 218, the length 216 being elongated. The width 218 may be sized with about a dimension of at least a circumference of the soft tissue 5 to which the flexible wrap member 204 is to surround so that the flexible wrap member 204 may completely surround the soft tissue 5. In one embodiment, the width 218 of the flexible wrap member 204 may be larger than the circumference of the soft tissue 5 so that the flexible wrap member 204 overlaps itself upon being wrapped around the soft tissue 5.

In one embodiment, the flexible wrap member 204 may be porous with similar structural characteristics of the flexible member described in FIG. 2. In another embodiment, the flexible wrap member 204 may include pores 220 sized and configured to induce tissue growth, the pores 220 being in the range of about 50 to 250 microns. The pores 220 may extend through the depth 214 of the flexible wrap member 204 or may be openings or recesses within the surface. In either case, the pores 220 may be sized to encourage cell attachment and tissue ingrowth into the flexible wrap member 204. In another embodiment, the outer surface 210 of the flexible wrap member 204 may include a non-porous surface. In another embodiment, the flexible wrap member 204 may include an additional layer 222 of material to form the outer surface 210 of the flexible wrap member 204 that is non-porous. In another embodiment, the outer surface 210 of the flexible wrap member 204 may include pores, but the pores defined in the outer surface 210 are less than 50 microns or the pores defined in the outer surface 210 may be sized to inhibit or limit tissue ingrowth.

With respect to FIGS. 14 and 15, the flexible wrap member 204 may be employed with the before-discussed components of a repair device 224. For example, in one embodiment, the repair device 224 may include the flexible wrap member 204, multiple anchors 172, and one or more rigid members, such as a single rigid member 134 (see also FIG. 9). The flexible wrap member 204 may be positioned within the cradle portion 26 (FIG. 7) of the delivery device, the cradle portion 26 also holding the rigid member 134 such that the rigid member 134 is disposed between the bed surface 28 (FIG. 7) of the cradle portion 26 and the flexible wrap member 204. The soft tissue 5, such as a severed tendon, may then be positioned within the cradle portion 26 and over the flexible wrap member 204. The flexible wrap member 204 may then be wrapped around the severed tendon, as indicated by arrow 206. The multiple anchors 172, held within the cartridge 24 (FIG. 1) of the delivery device 22, may then be actuated to be forced from the cartridge 24 and into the flexible wrap member 204, through the soft tissue 5 and through opposing notches 136 defined in the rigid member 134. The multiple anchors 172 then engage the canted anvil buckets 112 (FIG. 7) defined in the bed surface 28 of the cradle portion 26 to be forced to curl through openings 138 (FIG. 9) defined in the rigid member 134 such that the curled legs of the anchors 172 extend back through the flexible wrap member 204 and into the soft tissue 5 (similar to that depicted in FIG. 6B). In one embodiment, the multiple anchors 172 may be coupled by the flexible member defining the filament 182 (see also FIG. 13). In another embodiment, the flexible wrap member 204 may act as the various embodiments described herein for a flexible member such that the cartridge 24 (FIG. 1) may not hold a pre-positioned flexible member or filament 182 therewith.

As set forth, the flexible wrap member 204 may be positioned around the soft tissue 5 prior to coupling anchors 172 to the rigid member 134 and the flexible wrap member 204. As such, the flexible wrap member 204 may act as a strength member to the severed soft tissue or tendon 5. Further, the flexible wrap member 204 may act as an ingrowth substrate for inducing tissue growth through and along the flexible wrap member 204 so as to bridge any gap that may occur between the severed tendon ends. In another embodiment, the flexible wrap member 204 may be positioned around the severed tendon subsequent to fixating a given repair device to the severed tendon so as to act as an ingrowth substrate along the tendon.

Figure 16:
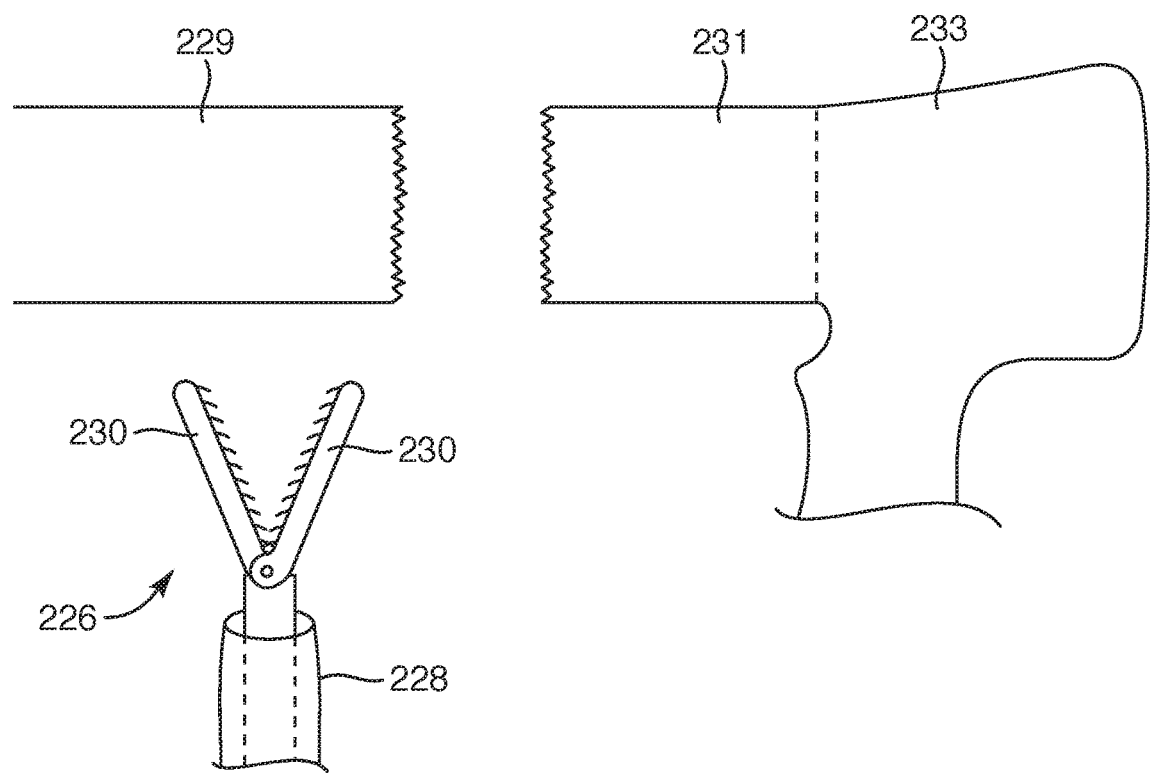
FIG. 16 is a simplified view of a capture device adjacent a soft tissue repair site of an achilles tendon, according to another embodiment of the present invention.

With respect to FIG. 16, a retrieving device 226 for retrieving a tendon that has migrated or withdrawn from the ruptured or severed site may be provided. The retrieving device 226 may be deployable from a sheath 228 and configured to retrieve a tendon percutaneously from the anatomy with minimal cuts to the anatomy. For example, a severed Achilles tendon portion may withdraw itself further into its tendon sheath from the point of the sever at a tendon stump. The physician may advance the retrieving device 226 percutaneously toward the severed tendon portion 229 and, once the end of the sheath 228 is adjacent the tendon portion 229, the physician may deploy the retrieving device 226, grab the tendon portion 229 with clamps 230 of the retrieving device 226 and pull the tendon portion 229 adjacent the tendon stump 231.

Figure 17:
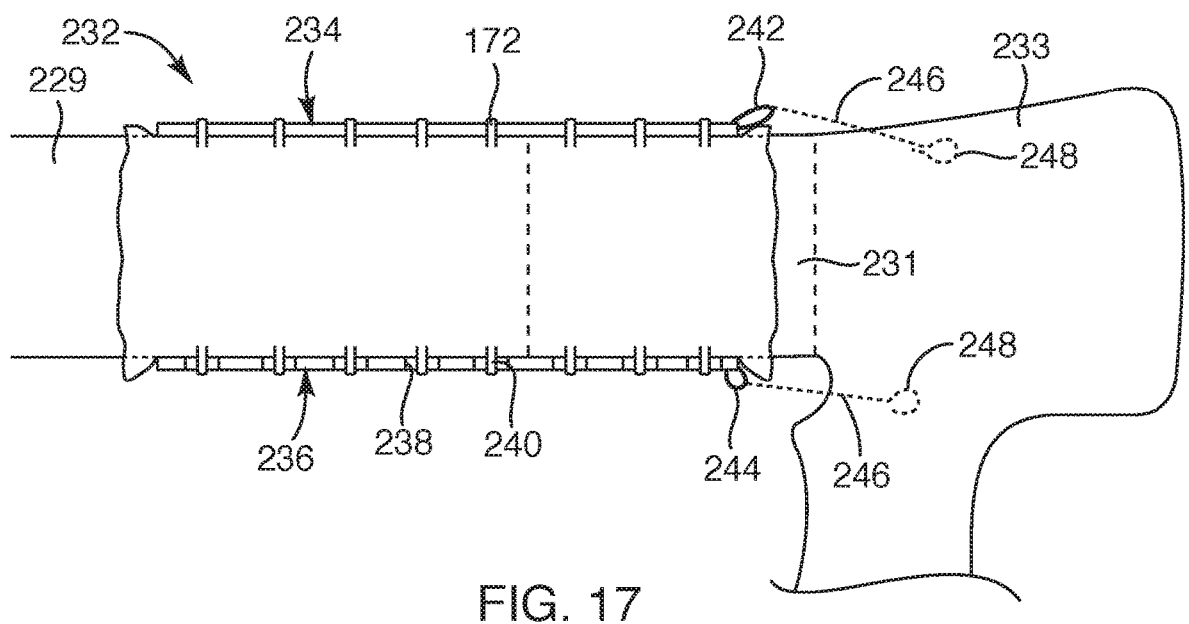
FIG. 17 is a side view of a repair device, depicting the repair device for repairing the Achilles tendon, according to another embodiment of the present invention.

Now with reference to FIGS. 16 and 17, a repair device 232 for attaching to soft tissue at a repair site of the soft tissue is provided. The repair device 232 of this embodiment may be employed with any suitable severed or ruptured tendon. For example, as depicted, a severed tendon may be a severed Achilles tendon including a tendon portion 229, such as the Achilles tendon portion, and a tendon stump 231, such as the Achilles tendon stump, the tendon stump 231 extending from a bone portion 233, such as the calcaneus bone portion.

The repair device 232 employed with the severed Achilles tendon may be similar to the previous repair devices and the variations of components described herein. For example, the repair device 232 may include the flexible wrap member 204 configured to wrap around the severed tendon with an upper rigid substrate 234 and a lower rigid member 236 coupled together with anchors 172 and to sandwich the flexible wrap member 204 and severed tendon therebetween. The flexible wrap member 204 may be similar to that described and depicted relative to FIGS. 14 and 14A. The upper rigid substrate 234 may be similar to the upper plate member described in FIG. 8. The lower rigid member 236 may be similar to the single rigid member described in FIG. 9. Further, as described in previous embodiments, the legs 240 of the anchors 172 may extend through notches 238 defined in the lower rigid member 236 to engage canted anvil buckets 112 defined in the cradle portion 26 to urge the legs 240 to curl in a controlled manner and to extend and wrap around the lower rigid member 236 and through openings defined in the lower rigid member 236.

Further, in one embodiment, the repair device 232 may include a first bone coupling portion 242 and a second bone coupling portion 244. For example, the upper rigid substrate 234 may include the first bone coupling portion 242 and the lower rigid member 236 may include the second bone coupling portion 244. Each of the first and second bone coupling portions 242, 244 may include a flexible filament 246 or suture like member (shown in outline form) with a bone anchor attachment portion 248. Such bone anchor attachment portion 248 may be sized and configured to attach any suitable bone anchor. In this manner, the repair device 232 may be configured to be further secured to the bone portion 233 adjacent the tendon stump portion.

Figure 18:
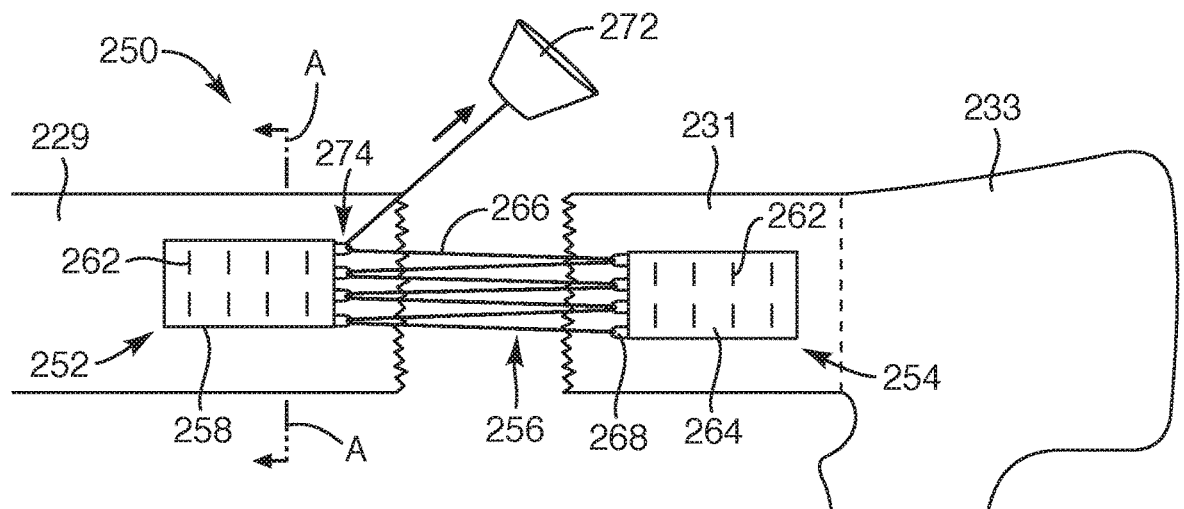
FIG. 18 is a side view of another embodiment of a repair device, depicting the repair device having a first part and a second part coupled together with a filament synch, according to the present invention.
Figure 18A:
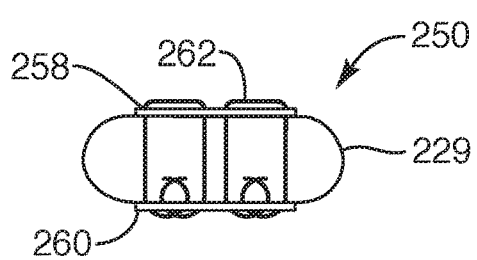
FIG. 18A is a cross-sectional view of the repair device taken along section line A-A of FIG. 18, according to another embodiment of the present invention.
Figure 19:
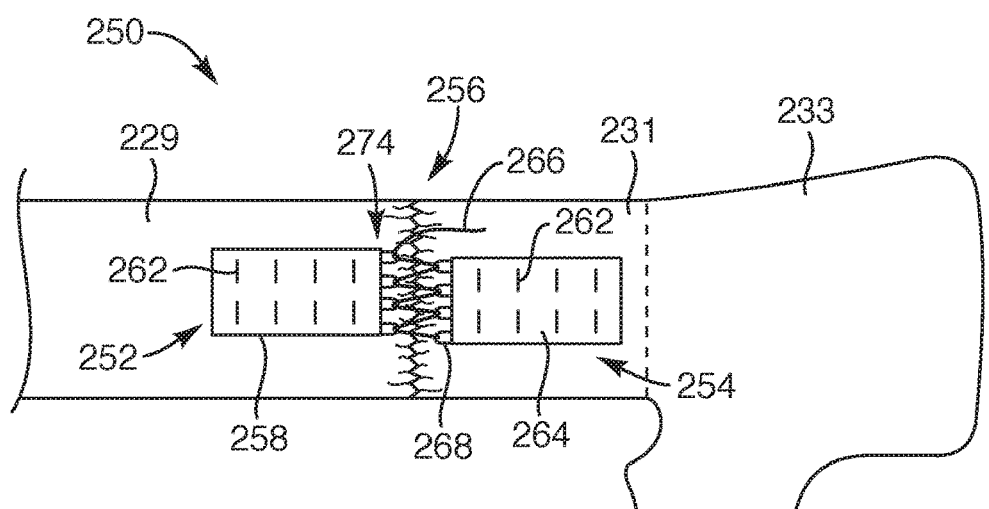
FIG. 19 is a side view of the repair device similar to FIG. 18, depicting the first and second parts moved adjacent each other with the filament synch, according to another embodiment of the present invention.

Now with reference to FIGS. 18, 18A and 19, another embodiment of a repair device 250 for attaching to a severed tendon, such as the Achilles tendon, is provided. In this embodiment, the repair device 250 may include a first part 252 and a second part 254 that may be synched together with a synch portion 256. The first part 252 may include a first side plate 258 and a second side plate 260, the first and second side plates 258, 260 defining openings/notches sized and configured to receive anchors 262 for coupling the first and second side plates 258, 260 together and sandwiching the tendon portion 229 therebetween. Similarly, the second part 254 may include a third side plate 264 and a fourth side plate (not shown), the third and fourth side plates defining openings sized and configured to receive anchors 262 for coupling the third and fourth side plates together with the tendon stump 231 sandwiched therebetween. The anchors 262 may be similar to previously described anchors with a u-shaped configuration and legs that curl and wrap around the opposing second side plate 260 and fourth side plate (not shown) of the respective first and second parts 252, 254 of the repair device 250. In this manner, each of the first and second parts 252, 254 may be coupled to each other similar to the opposing members and anchor arrangements of previous embodiments (see FIG. 6B).

In addition, as depicted, the first and second parts 252, 254 may each define openings to receive the anchors 262 aligned in multiple rows for coupling the respective opposing plates. In another embodiment, the anchors 262 may be aligned in a single row in the first and second parts 252, 254 to couple the respective opposing plates, similar to the previous embodiments. In still another embodiment, the first and second parts 252, 254 may each define openings for receiving the anchors 262 in a staggered arrangement to couple the respective opposing plates.

As set forth, the repair device 250 may include a synch portion 256. The synch portion 256 may include a draw string 266 wound or extending through eyelets 268 positioned on the first and second parts 252, 254 of the repair device 250. In one embodiment, the eyelets 268 may be positioned on one side of each of the first side plate 258 and the second side plate 260 as well as on one side of each of the third side plate 264 and the fourth plate (not shown) such that the one side of the first part 252 is positioned adjacent to the one side of the second part 254. The draw string 266 may extend through each of the eyelets 268 to a pull portion 272. Upon the first and second parts 252, 254 being secured to the severed tendon, the draw string 266 may draw the respective first and second parts 252, 254 toward each other by pulling the pull portion 272. In other words, the draw string 266 may be drawn to pull the first part 252 toward the bone portion 233 and the second part 254.

Figure 19A:
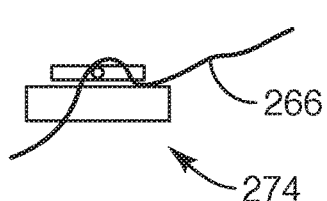
FIG. 19A is a simplified side view of a locking mechanism of the repair device of FIG. 18, according to another embodiment of the present invention.

A method of repairing a severed tendon with the repair device 250 will now be described. Similar to that described in the previous embodiment, the tendon portion may be retrieved and positioned by a physician with a retrieving device 226 (FIG. 16) so as to position the tendon portion 229 adjacent to the tendon stump 231. Further, similar to previous embodiments described herein, the physician may then secure the first part 252 to the tendon portion 229 with a delivery device having a cradle portion and a cartridge. For example, the physician may lay the tendon portion 229 within the cradle portion of the delivery device and over the second side plate 260 positioned over the bed surface of the cradle portion. Also, the cartridge of the delivery device may hold the first side plate 258 and the anchors 262. Upon the physician being satisfied with the position of the tendon portion 229 in the cradle portion, the delivery device may then be actuated to force the anchors 262 from the cartridge to continue through the first side plate 258 and tendon portion 229 and be forced against anvil buckets in the bed surface of the cradle portion. The anchors 262 may then be wrapped around the second side plate 260 and through openings defined in the second side plate 260 in a curled manner to secure the first part 252 of the repair device 250 to the tendon portion 229. In a similar manner, the physician may then secure the second part 254 of the repair device 250 to the tendon stump 231. Once each of the first part 252 and second part 254 is attached to the severed tendon, the physician may synch or draw the draw string 266 by pulling on the pull portion 272 to pull the first part 252 toward the second part 254 or the bone portion 233 so that the severed end of the tendon portion 229 abuts the severed end of the tendon stump 231 or the bone portion 233. The physician may then secure the draw string 266 in the pulled position to maintain the tendon ends in an abutting relationship. Such securing of the draw string 266 may be employed with a locking mechanism 274 positioned with or adjacent to the last eyelet that the draw string 266 passes through. The locking mechanism 274 may be any suitable locking mechanism, such as a buckle type arrangement as depicted in FIG. 19A, so that the pulled draw string 266 is maintained to the pulled position. The physician may then further secure the draw string 266 with a knot or the like.

Figure 20:
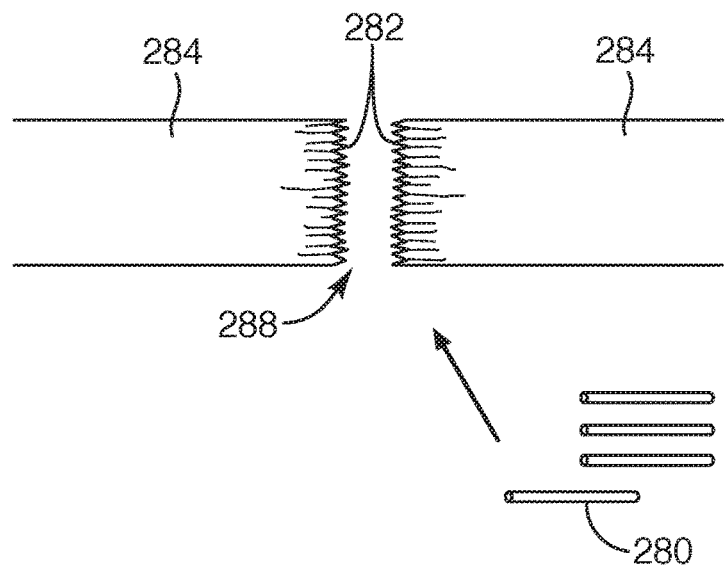
FIG. 20 is a side view of a tissue growth member positioned adjacent a soft tissue repair site of soft tissue, the tissue growth member being a component employed with a repair device, according to another embodiment of the present invention.
Figure 21:
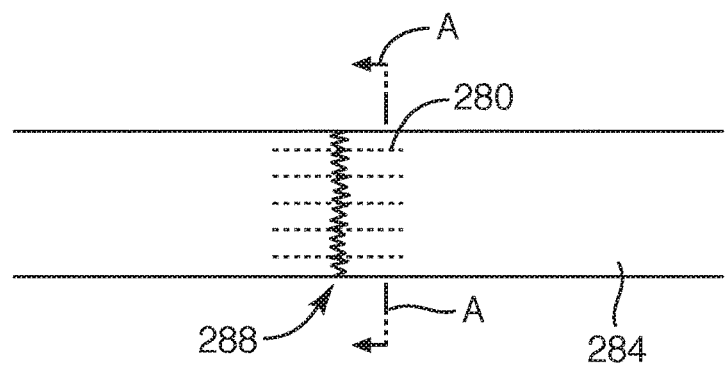
FIG. 21 is a side view of the tissue growth member positioned within the soft tissue along and adjacent the soft tissue repair site, according to another embodiment of the present invention.
Figure 21A:
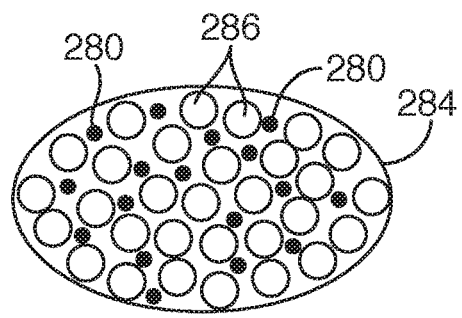
FIG. 21A is a cross-sectional view taken along section A-A of FIG. 21, depicting the tissue growth member positioned adjacent and along fibers of the soft tissue, according to another embodiment of the present invention.

Now with respect to FIGS. 20, 21, and 21A, a tissue growth member 280 or tissue strengthening member configured to be positioned within the severed tendon ends 282 of a tendon 284 at a repair site 288 is provided. Such tissue growth member 280 may be provided to the severed tendon ends 282 prior to securing the ends together with any one of the repair devices described herein. The tissue growth member 280 may be in the form of multiple rods, strips, or fibers, and/or gel, or combinations thereof. Such rods, strips, fibers and/or gel may be manually positioned by the physician with tweezers or the like so as to position the tissue growth member 280 alongside and within the tendon fibers 286. In one embodiment, the tissue growth member 280 may be a polymeric material. In another embodiment, the tissue growth member 280 may include a chemical inducing substance to enhance and induce tissue growth between the ruptured or severed tendon fibers 286 at and adjacent the repair site 288. In another embodiment, the rods, strips, fibers and/or gel may include collagen. In another embodiment, the rods, strips, fibers and/or gel may include a chemical for drug delivery. In another embodiment, the rods, strips, fibers and/or gel may be porous. Upon the tissue growth member 280 being added to the repair site 288, the physician may then fixate the tendon ends 282 with a repair device.

Figure 22:
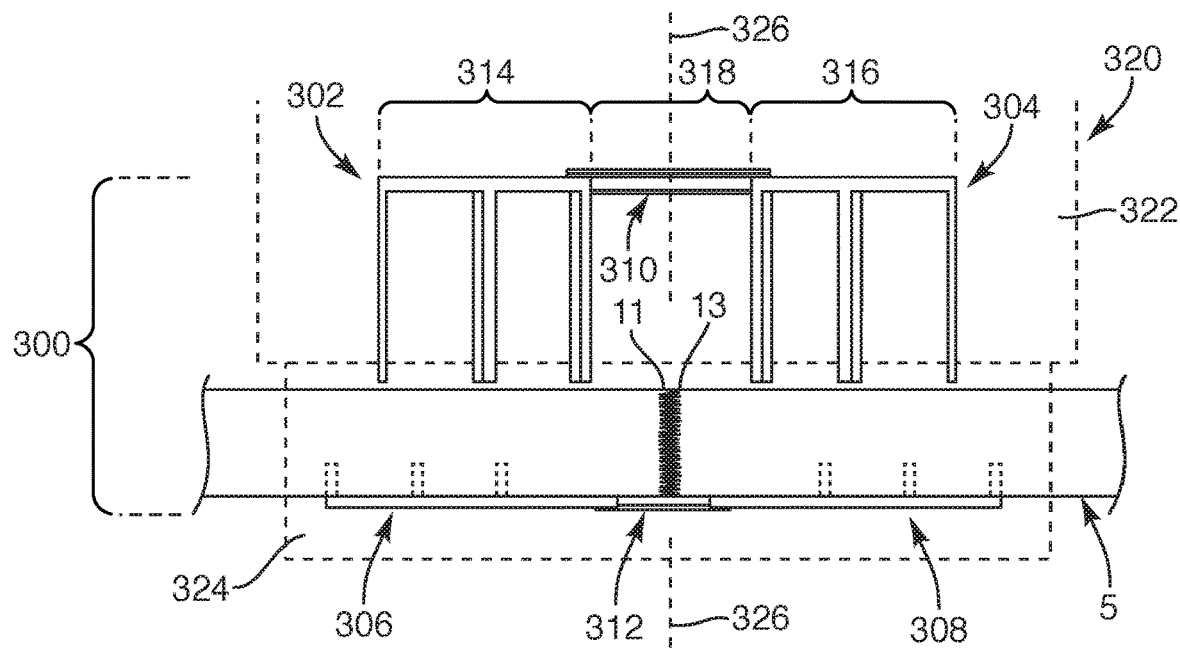
FIG. 22 is a side view of another embodiment of a repair device, depicting a portion of a delivery system in outline form, according to the present invention.

With reference to FIG. 22, another embodiment of a repair device 300, depicted in a pre-deployed state, including first and second anchors 302, 304 positioned opposite first and second plate members 306, 308, is provided. The first and second anchors 302, 304 may include an anchor coupling portion 310 and the first and second plate members 306, 308 may include a plate coupling portion 312. In the pre-deployed state, the first and second anchors 302, 304 may be positioned within a cartridge 322 and the first and second plate members 306, 308 may be positioned within a cradle portion 324, the cartridge 322 and cradle portion 324 being portions of a delivery device 320. The cartridge 322 and cradle portion 324 linearly moveable relative to each other, but maintaining a position along a delivery device axis 326. With the first and second plate members 306, 308 positioned in the cradle portion 324, soft tissue 5, such as tendon and/or ligament, may be positioned over the first and second plate members 306, 308 with severed first and second ends 11, 13 of the soft tissue 5 positioned over the plate coupling portion 312. The cartridge 322 with the first and second anchors 302, 304 disposed therein may then be positioned adjacent the soft tissue 5. The delivery device 320 may then be actuated so that the first and second anchors 302, 304 move from a pre-deployed state to a deployed state (not shown).

In this embodiment, the first and second plate members 306, 308 may be similar to, and perform similar functions as, the before-described rigid members. Further, in one embodiment, the first and second plate members 306, 308 may elongate (so as to be moveable to a longitudinally longer state) with a force applied thereto. Similarly, the first and second anchors 302, 304 define structural characteristics that may be configured to elongate. The anchor coupling portion 310 and the plate coupling portion 312 may be a flexible element and may substantially resist longitudinal elongation. In this manner, upon the repair device 300 being deployed and anchored to soft tissue 5, the first and second plate members 306, 308 and anchors 302, 304 may elongate while the anchor coupling portion 310 and the plate coupling portion 312 may substantially resist elongation as the soft tissue 5 is exercised and/or a force is applied to the soft tissue 5 so as to elongate the soft tissue 5. As such, the first anchor 302 and first plate member 306 define a first portion 314 or first zone of the repair device 300 that may elongate and the second anchor 304 and the second plate member 308 define a second portion 316 or a second zone of the repair device 300 that may elongate while the anchor coupling portion 310 and the plate coupling portion 312 define an intermediate portion 318 or middle portion or mid zone of the repair device 300 that substantially resists elongation.

Figure 23:
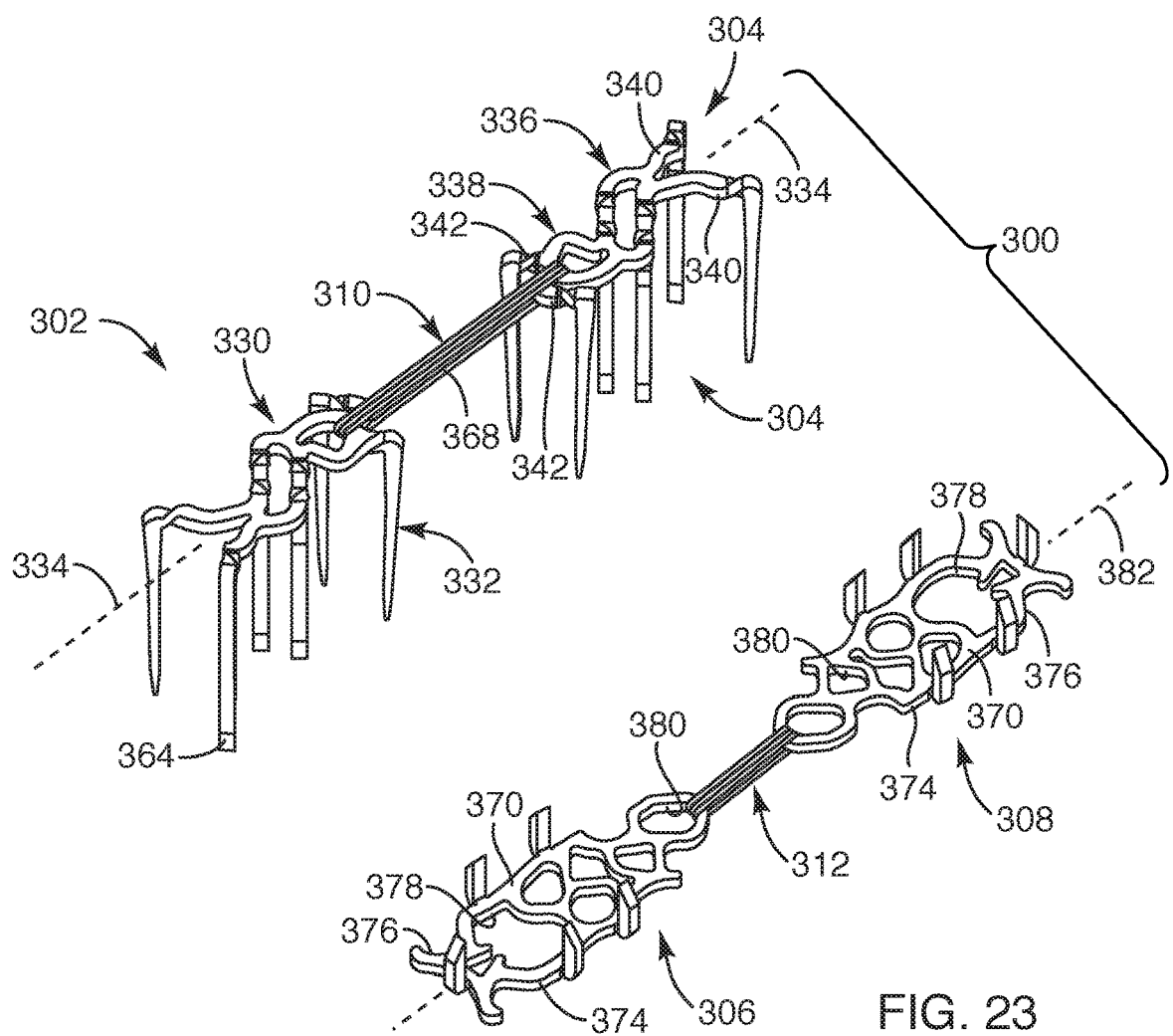
FIG. 23 is a perspective view of the repair device of FIG. 22, depicting the repair device having first and second anchors with opposing first and second plate members, according to another embodiment of the present invention.
Figure 24:
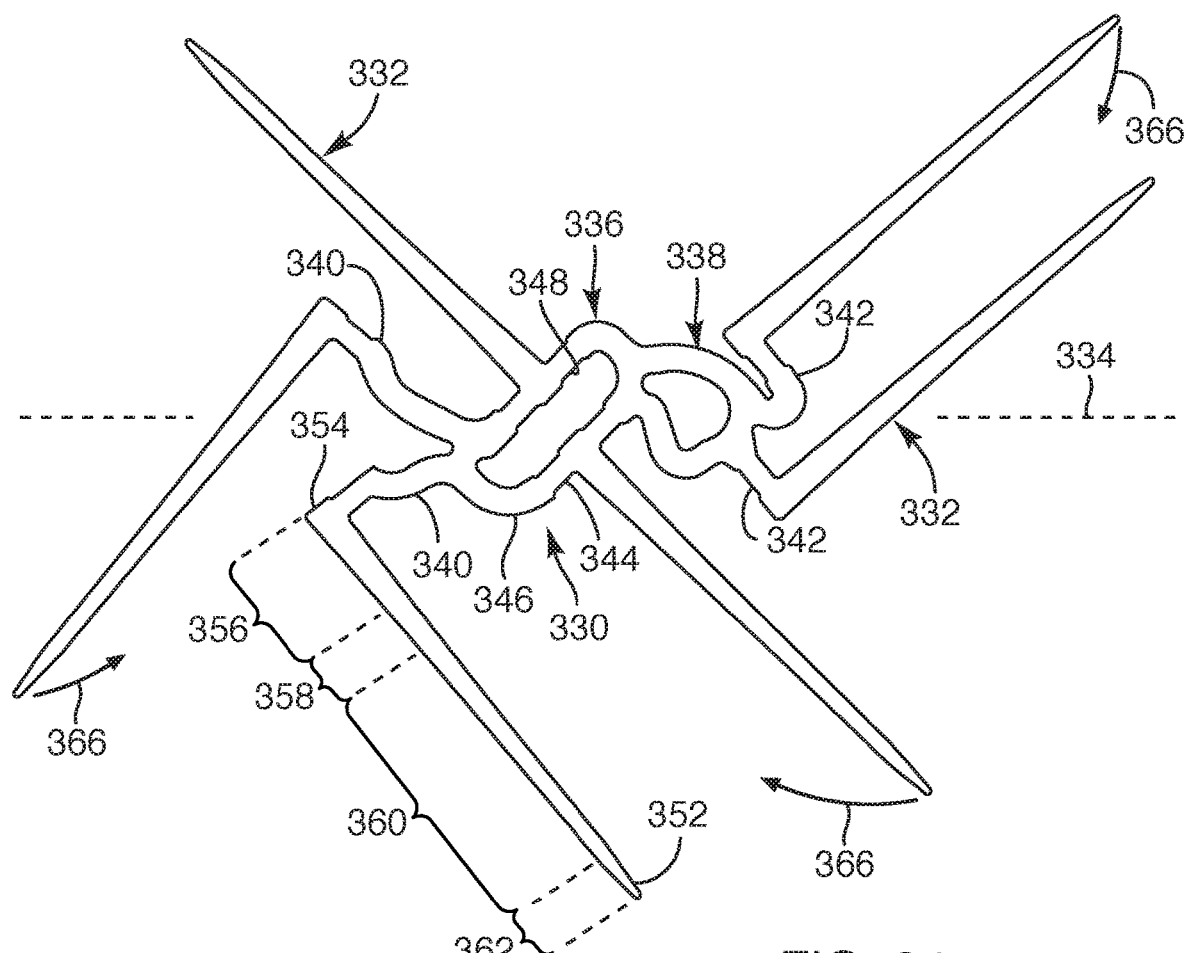
FIG. 24 is a top view of one of the anchors, depicting the anchor in a pre-formed state, according to another embodiment of the present invention.

Now with reference to FIGS. 23 and 24, details of the repair device 300 will now be described, FIG. 23 depicting the repair device 300 in a pre-deployed state and FIG. 24 depicting, for example, the first anchor 302 in a pre-formed state. The first and second anchors 302, 304 of the repair device 300 may each include a monolithic and seamless multi-cellular structure, the structure of each anchor including a body 330 and multiple legs 332, having a bug-like or arachnid appearance. Further, as positioned in a pre-deployed state, the first and second anchors 302, 304 may be oriented and aligned relative to each other to define an anchor longitudinal axis 334 extending along the anchor coupling portion 310 and through the first and second anchors 302, 304. The structure of the body 330 of each anchor may include a continuous interconnected structure (arcuate and linear) extending in a non-symmetrical manner with major portions of the body 330 extending transversely relative to the anchor longitudinal axis 334.

For example, the first anchor 302 may include the body 330 having an elongated central portion 336 and a head portion 338 with multiple outer extensions 340 extending outward from the central portion 336 and multiple inner extensions 342 extending from the head portion 338. Each of the elongated central portion 336, head portion 338, and outer and inner extensions 340, 342 may be substantially planar relative to each other. The legs 332 may extend generally perpendicular relative to the planar body 330, as depicted in FIG. 23. The second anchor 304 may be substantially similar to the first anchor 302, but rotated so that the head portion 338 and inner extensions 342 of the second anchor are adjacent the head portion 338 and inner extensions 342 of the first anchor 302.

As depicted in the top view of the first anchor 302 in FIG. 24 (and oriented relative to the anchor longitudinal axis 334), the elongated central portion 336 may include elongated lengths 344 extending generally parallel to each other with arcuate portions 346 at ends of the lengths to define an elongated elliptical shape. Further, the elongated central portion 336 may define an elongated opening 348 therein. The elongated lengths 344 of the elongated central portion 336 may extend transverse relative to the anchor longitudinal axis 334, which may extend upward from left-to-right. The head portion 338 may extend from one of the arcuate portions 346 with a tear-drop shape or the like, the head portion 338 defining a head opening therein. The head portion 338 may generally extend transversely relative to the anchor longitudinal axis 334 in a downward direction from left-to-right. The inner extensions 342 may extend in a curved manner and/or a straight manner from the head portion 338 and generally transverse relative to the anchor longitudinal axis 334. At the opposite end of the body 330, the outer extensions 340 may extend from the elongated central portion 336 in an arcuate and/or straight manner and may also extend generally transverse relative to the anchor longitudinal axis 334.

With respect to FIGS. 23 and 24, as previously set forth, each of the first anchor 302 and the second anchor 304 may include multiple legs 332. Each of the legs 332 may be integral and monolithic with the body 330 of a given anchor. In one embodiment, each anchor may include six legs, of which two legs 332 may extend from ends of the outer extensions 340, two legs 332 may extend from ends of the inner extensions 342, and two legs 332 may extend from the elongated lengths 344 of the elongated central portion 336 of the body 330. Each leg 332 may extend between a free end 352 and a base 354 and may include one or more tapers along at least a portion of a length of each leg. In one embodiment, each leg 332 may include a base portion 356, an intermediate portion 358, a bending portion 360, and an end portion 362. The base portion 356 may include a substantially uniform cross-section or slightly taper, the intermediate portion 358 may taper from the base portion 356 to the bending portion 360, and the bending portion 360 may slightly taper from the intermediate portion 358 to the end portion 362. The end portion 362 may taper such that the free end 352 comes to a point and/or an edge 364 extending a distance. The distance may be a thickness or depth of the sheet material from which the anchor is cut.

As depicted in FIG. 24, the first and second anchors 302, 304 may be formed from sheet material, such as stainless steel, titanium, or Nitinol, or any other suitable material. The first and second anchors 302, 304 may be, for example, laser cut from the sheet material, or cut utilizing other suitable methods known in the art. Upon cutting the anchors from the material, the legs 332 may then be bent in predetermined directions, shown by arrows 366, such that the legs are bent (into the paper) to extend substantially orthogonal relative to the body 330 of the anchors. Such bending of the anchors may be accomplished using fixtures to precisely bend the anchors. In the case of the Nitinol material, the legs may be held in the position desired and then heat-set, as known by one of ordinary skill in the art. The anchors may also undergo a polishing process, such as electo or chemical polishing/etching, or any other process known in the art.

Referring back to FIG. 23, upon the first and second anchors 302, 304 being formed, the anchor coupling portion 310 may be applied thereto. The anchor coupling portion 310 may be configured to couple the first and second anchors 302, 304 together at a pre-determined distance from each other. The anchor coupling portion 310 may be in the form of a band or ribbon. The anchor coupling portion 310 may be flexible so as to allow the first and second anchors 302, 304 to move to different orientations relative to each other, and/or to make a tight turn around a radius or the like, and/or to allow the first and second anchors 302, 304 to move closer to each other relative to the pre-determined distance. Further, the anchor coupling portion 310 may be sized and configured to substantially resist elongation beyond the pre-determined distance. The anchor coupling portion 310 may be in the form of one or more filaments 368 that may be threaded through, for example, the head opening 350 of each head portion 338 of the first and second anchors 302, 304, or any other suitable aperture of the first and second anchors 302, 304.

In one embodiment, the anchor coupling portion 310 and the plate coupling portion 312 may be a polymeric filament or a polymeric fiber with one or more filaments/fibers. The polymeric filament or fiber may be a polyethylene material, such as ultra-high-molecular-weight polyethylene ("UHM-WPE"), a polyester material, a polypropylene material, or the like. In another embodiment, the polymeric filament or fiber may be a bioresorbable material, such as polylactide ("PLA"), polycaprolactone ("PCL"), polydioxanone ("PDX"), or the like, or any other suitable bioresorbable material as known to one of ordinary skill in the art. Such a single filament or fiber may include a woven, braided, strands wound in a side-by-side configuration, or strands wound side-by-side and twisted configuration.

Figure 25:
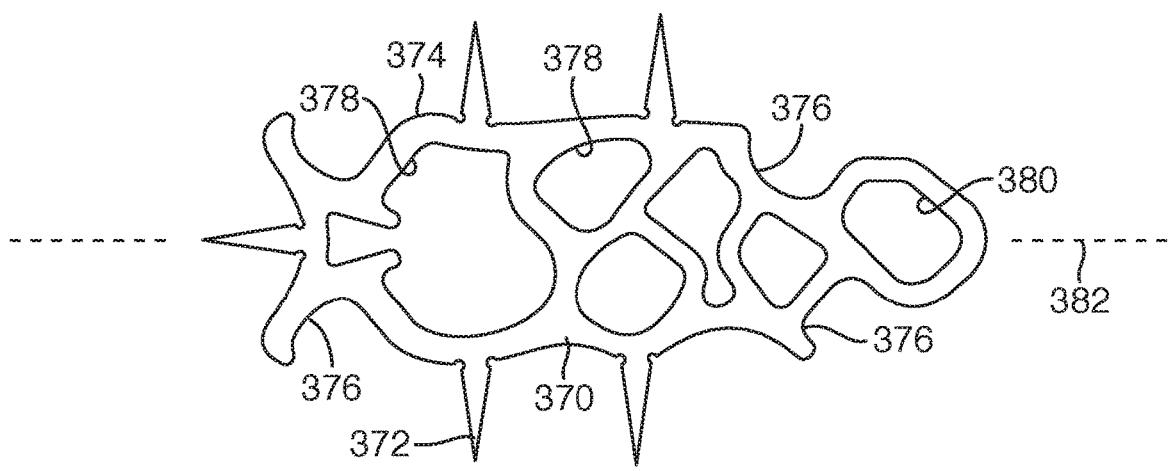
FIG. 25 is a top view of one of the plate members, depicting the plate member in a pre-formed state, according to another embodiment of the present invention.

Now with reference to FIGS. 23 and 25, the repair device 300 may also include the first and second plate members 306, 308. Each of the plate members may be a monolithic structure. The first and second plate members 306, 308 may be coupled together with the plate coupling portion 312 so that the plates are oriented relative to each other to define a plate longitudinal axis 382. Further, each of the plate members may include a plate portion 370 and multiple tines 372. The plate portion 370 may define a periphery 374 with notches 376 defined therein. Further, the plate portion 370 may include multiple openings 378 defined therein such that the plate portion 370 defines a multi-cellular structure. The openings 378 and notches 376 defined in each plate portion 370 may be sized and configured to receive the legs 332 of the first and second anchors 302, 304 so as to inter-lock the first and second anchors 302, 304 to the respective first and second plate members 306, 308, discussed in further detail herein. The multiple tines 372 may extend substantially orthogonal or canted relative to the plate portion 370, as depicted in FIG. 23. As depicted in FIG. 25, the first and second plate members 306, 308 may be formed from sheet material such that, in the pre-formed state, the tines 372 may be within the same plane as the plate portion 370. Once cut from the sheet material, the tines 372 may be bent to extend substantially orthogonal from the periphery of the plate portion 370, similar to that depicted in FIG. 23, and utilizing similar methods set forth for bending the legs 332 of the anchors.

As set forth, the first and second plate members 306, 308 may be coupled together with a plate coupling portion 312. Such plate coupling portion 312 may be sized and configured to position the first and second plate members 306, 308 a predetermined distance from each other. The plate coupling portion 312 may extend between respective inner openings 380 defined in the respective first and second plate members 306, 308. The plate coupling portion 312 may include similar structural characteristics as that described for the anchor coupling portion 310. For example, the plate coupling portion 312 may be flexible, but substantially resist elongation. In one embodiment, the plate coupling portion 312 may be one or more filaments. In another embodiment, the plate coupling portion may be in the form of a band. In another embodiment, the one or more filaments may be wrapped to exhibit a band configuration as the plate coupling portion 312.

With reference to FIGS. 26 and 27, alignment of the legs 332 of the first and second anchors 302, 304 relative to the notches 376 and openings 378 of the respective first and second plate members 306, 308 is depicted. For example, inner side legs 384 of the first anchor 302 may correspond with inner side notches 386 of the first plate member 306. Similarly, outer side legs 388 of the first anchor 302 may correspond with outer side notches 390 of the first plate member 306. Further, middle legs 392 of the first anchor 302 may correspond with two of the openings 378 defined in the first plate member 306. A similar arrangement may be utilized with the legs 332 of the second anchor 304 relative to the second plate member 308.

As previously set forth, the first and second plate members 306, 308 may be configured to be positioned within a cradle portion 324. The cradle portion 324 may include a bed surface 394 with an inset recess 396 defined therein. The inset recess 396 may define an inset surface 398 with anvil buckets 400 defined therein. The inset recess 396 may be sized to act as a guide so that the periphery 374 of the first and second plate members 306, 308 may be appropriately oriented and positioned within the cradle portion 324. Similar to previous embodiments, the anvil buckets 400 may include a bottom surface 402 having a downward slope 404 and an upward slope 406 and an upstanding wall 408 or functional wall that may be oriented, sized and configured to manipulate a direction for bending the legs 332 to be curled or bent through a pre-determined opening 378 defined in the plate members. FIG. 27A illustrates the first plate member 306 positioned within the inset recess 396 of the bed surface 394, illustrating the relationship of the notches 376 and openings 378 of the first plate member 306 relative to the anvil buckets 400.

Further, with respect to FIGS. 26, 27, and 27A, the outer side legs 388 correspond with the outer side notches 386, which in turn correspond with the outer side anvil buckets 410, the outer side buckets 410 configured to manipulate the legs 332 to wrap around a portion of the plate portion 370 and through one of the openings 378 of the plate portion 370. Similarly, the inner side legs 384 correspond with the inner side notches 386, which in turn correspond with the inner side anvil buckets 412, the inner side anvil buckets 412 configured to manipulate the legs 332 to wrap around a portion of the plate portion 370 and through one of the openings 378. The middle legs 392 wrap correspond with middle anvil buckets 414 and extend through some of the middle openings 378 defined in the plate member, as depicted. In this manner, the downward and upward slopes 404, 406 of the anvil buckets 400 with the upstanding functional wall 408 of each anvil bucket 400 may manipulate the legs 332 to wrap and secure the first and second anchors 302, 304 to the respective first and second plate members 306, 308.

In another embodiment, each leg 332 of the first anchor 302 is positioned laterally relative to a cradle longitudinal axis 416 (or plate longitudinal axis 382) at a different lateral distance than any other leg 332 of the first anchor 302. Similarly, each leg 332 of the second anchor 304 is positioned laterally relative to the cradle longitudinal axis 416 at a different lateral distance than any other leg 332 of the second anchor 304. As such, upon anchoring the repair device 300 to soft tissue (not shown), the legs 332 will wrap and bundle different longitudinally extending tendon fibers (not shown) relative to each of the first and second anchors 302, 304. In another embodiment, the orientation of each anvil bucket pair is different than the orientation of any other anvil bucket pair that corresponds with the legs 332 of either the first anchor 302 or the second anchor 304. In this manner, the holding strength to the longitudinally extending tendon fibers will be greater than if the legs were bent from the same lateral distance from the cradle longitudinal axis 416 and at the same orientation.

Figure 28:
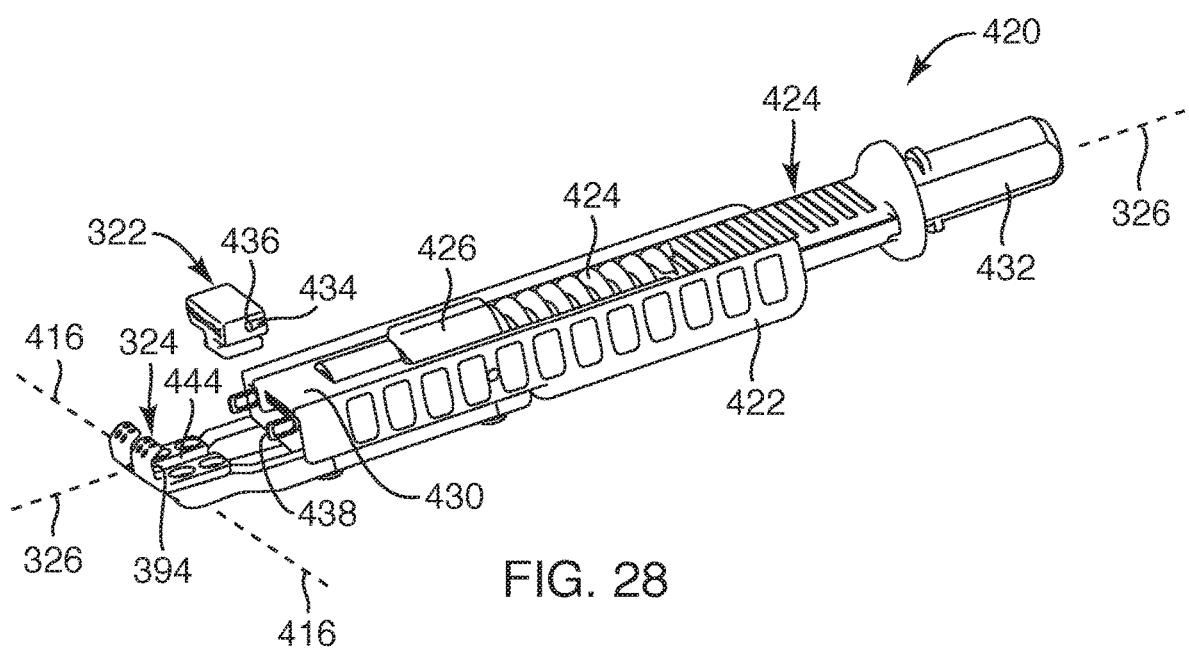
FIG. 28 is a perspective view of an elongated handle assembly, depicting a cartridge dis-engaged with the elongated handle assembly, according to another embodiment of the present invention.

With respect to FIG. 28, a perspective view of an elongated handle assembly 420 with the cartridge 322 disengaged from the elongated handle assembly 420, is provided. In one embodiment, the elongated handle assembly 420 may include the cradle portion 324, a slide guide 422, a slider 424 and a turn knob 426 for linearly moving the slider 424 relative to the slide guide 422. The slider 424 may include a worm drive 428 and a pusher block housing 430 coupled thereto. The slider 424 may also include a proximal connecting portion 432 for connecting to a trigger handle 450 (FIG. 33). The cradle portion 324 may be fixedly coupled to the slide guide 422. Further, the cradle portion 324 includes the bed surface 394 and a channel shape oriented and configured to receive severed or lacerated soft tissue portions, such as tendon and/or ligament. The cradle portion 324 may be oriented to receive the soft tissue portions oriented longitudinally and parallel with the cradle axis 416. Further, the cradle axis 416 extends orthogonal to the delivery device axis 326 of the elongated handle assembly 420. Such delivery device axis 326 of the elongated handle assembly 420 may extend along or through a pusher shaft axis 452 (FIG. 32A) co-aligned or co-axial with delivery device axis 326, discussed in further detail hereafter.

Figure 29:
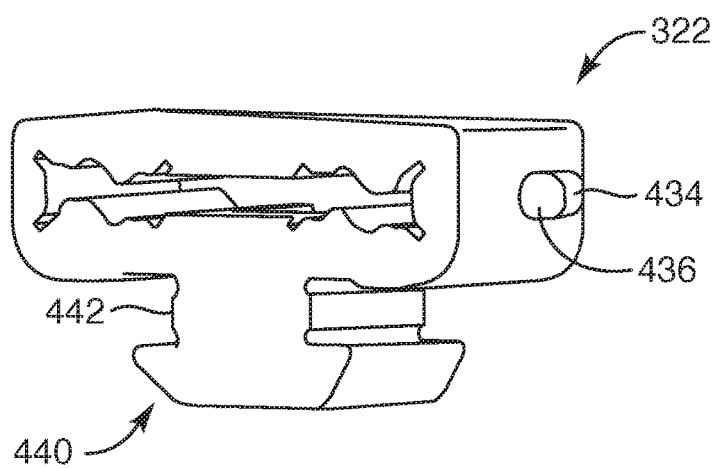
FIG. 29 is an enlarged perspective view of the cartridge, according to another embodiment of the present invention.

With respect to FIGS. 28 and 29, in one embodiment, the cartridge 322 may be removeably attachable to the pusher block housing 430. The cartridge 322 may include attachment portions in the form of protrusions with a ramp portion 434 and a holding portion 436, the protrusions extending from opposing lateral sides of the cartridge 322. The pusher block housing 430 may include clips 438 coupled to opposing lateral sides of the pusher block housing 430. The cartridge 322 may be attached by simply manually positioning the cartridge 322 such that the clips 438 move up a corresponding ramp portion 434 and hook to the holding portion 436 of each protrusion. With this arrangement, the cartridge 322 may be positioned against a distal end of the pusher block housing 430.

Figures 30, 31:
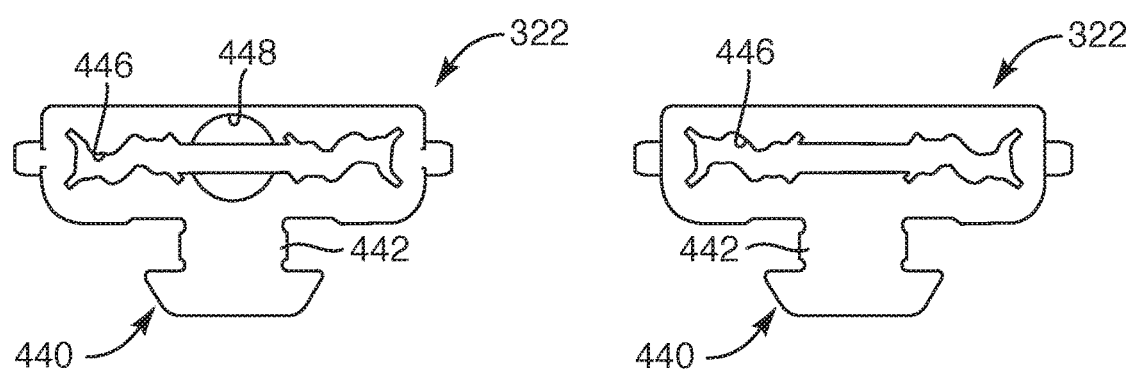
FIG. 30 is rear view of the cartridge, according to another embodiment of the present invention.
FIG. 31 is a front view of the cartridge, according to another embodiment of the present invention.

The cartridge 322 may also include a base alignment portion 440 defining opposing grooves 442, best shown in rear and front views of the cartridge in respective FIGS. 30 and 31. The opposing grooves 442 defined in the base alignment portion 440 of the cartridge 322 may be sized and configured to align and correspond with a channel 444 (FIG. 28) defined in the cradle portion 324. Such base alignment portion facilitates the cartridge 322 to be appropriately aligned with the cradle portion 324 so that the first and second anchors 302, 304 are aligned with the first and second plate members 306, 308 (see FIG. 36).

In another embodiment, the cartridge 322 includes a contoured aperture 446 defined in a central portion of the cartridge 322 and extending through the cartridge 322. The contoured aperture 446 may be shaped, sized and configured to receive the first and second anchors 302, 304 (not shown) such that the contoured aperture 446 defines a corresponding shape or profile of the periphery of the first and second anchors 302, 304. As depicted in FIG. 28, the rear side of the cartridge 322 may include an additional recess 448 extending partially into the rear side of the cartridge 322. Such additional recess 448 may be sized to receive an enlarged coupling between a push rod 454 and a pusher block 456 (see FIG. 32A), upon the pusher block 456 being moved into the cartridge to push the first and second anchors 302, 304 from the cartridge 322.

Figure 32:
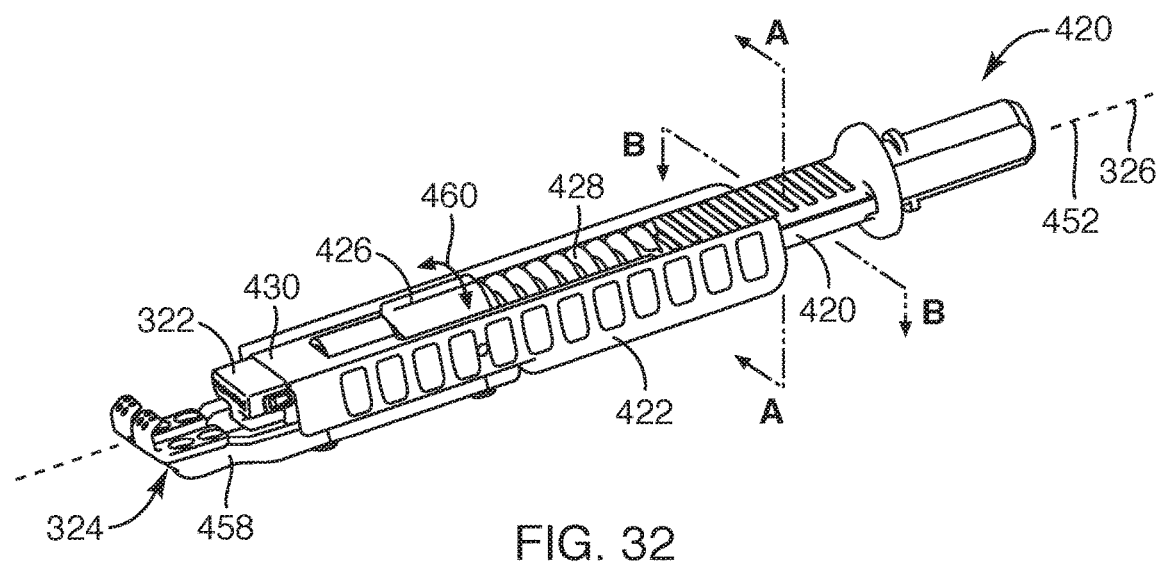
FIG. 32 is a perspective view of the elongated handle assembly with the cartridge engaged with the elongated handle assembly, according to another embodiment of the present invention.
Figure 32A:
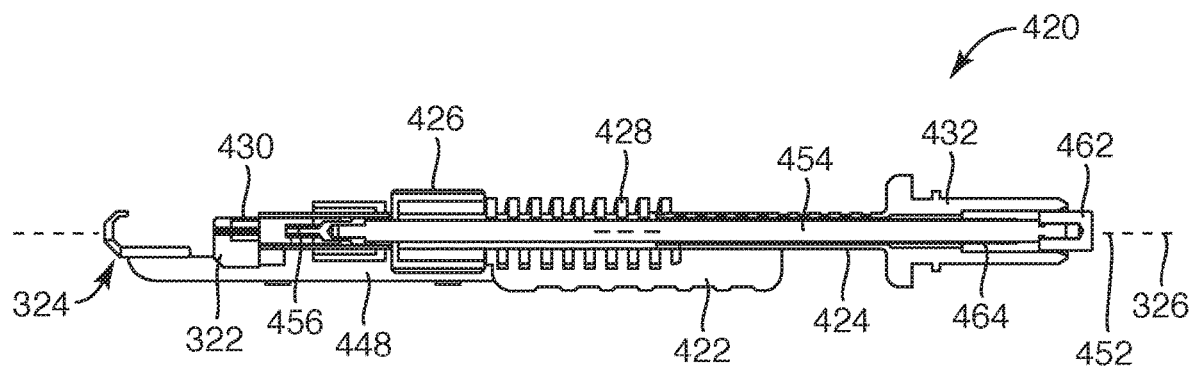
FIG. 32A is a cross-sectional side view of the elongated handle assembly taken along section line A-A of FIG. 32, according to another embodiment of the present invention.
Figure 32B:
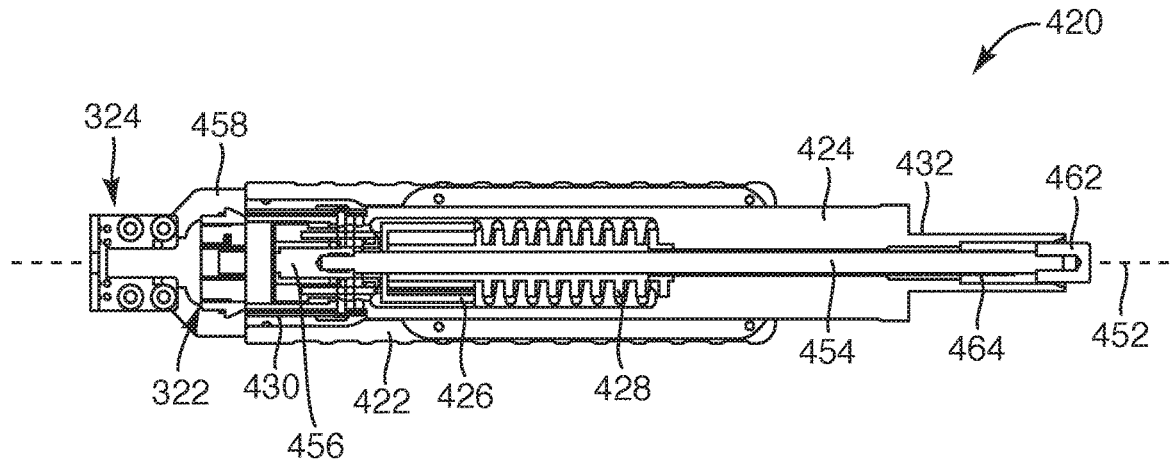
FIG. 32B is a cross-sectional side view of the elongated handle assembly taken along section line B-B of FIG. 32, according to another embodiment of the present invention.
Figure 33:
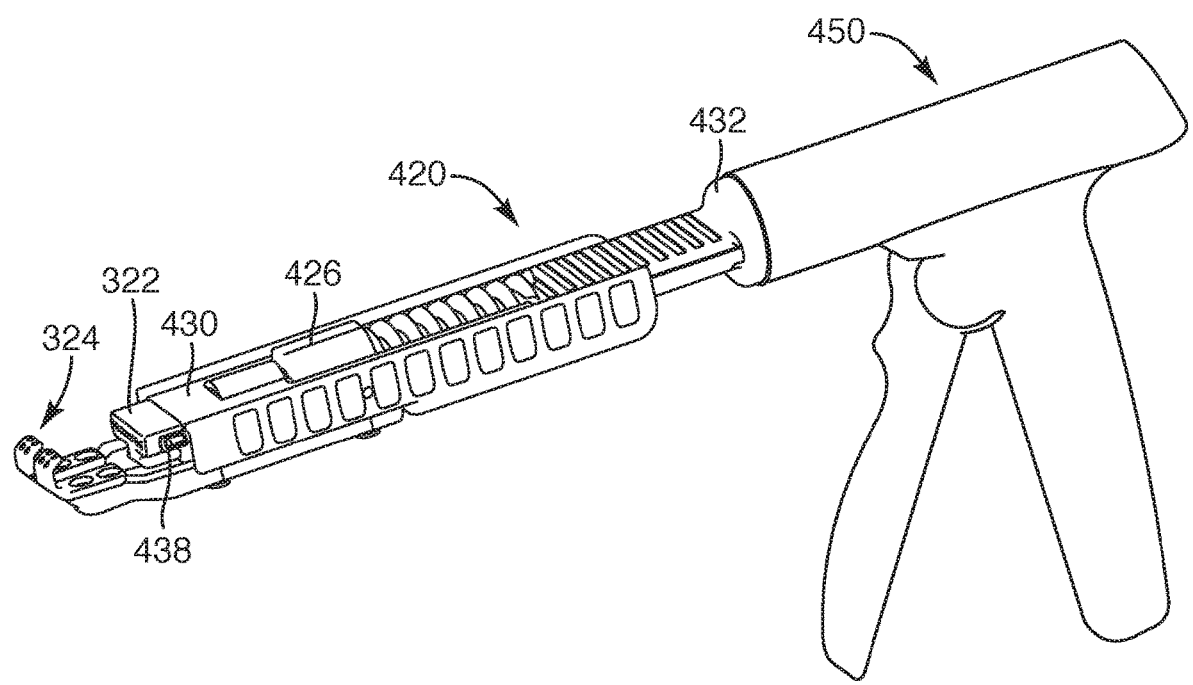
FIG. 33 is a perspective view of the elongated handle assembly with a trigger handle of the delivery device, according to another embodiment of the present invention.

Now with reference to FIGS. 32, 32A, and 32B, further description of the elongated handle assembly 420 with the cartridge 322 engaged thereto will now be provided. As previously set forth, the elongated handle assembly 420 may include the slide guide 422 fixed to the cradle portion 324. The cradle portion 324 may be fixed to the slide guide 422 via one or more connector plates 458 along an underside of the slide guide 422 and cradle portion 324. By rotating the turn knob 426, as shown with rotational arrow 460, the worm drive 428 is activated to move the slider 424 and pusher block housing 430 as well as the cartridge 322 toward the cradle portion 324. Opposite rotation of the turn knob 426 will move the pusher block housing 430 and cartridge 322 away from the cradle portion 324.

As depicted in the cross-sectional views of FIGS. 32A and 32B, the slider includes the elongated push rod 454, defining shaft axis 452, extending through the turn knob 426 and worm drive 428 with opposing ends extending between a push button 462 and a pusher block 456. At the proximal side, the push rod 454 may be coupled and fixed to the push button 462. Further, the push rod 454 may be spring biased toward a proximal position with a return spring 464 biased between a portion of the proximal connecting portion 432 or slider 424 and a non-exposed surface of the push button 462.

With respect to FIGS. 32A, 32B, and 33, at the distal end of the push rod 454, the push rod 454 may be coupled to the pusher block 456 and disposed within the pusher block housing 430. Upon coupling the trigger handle 450 to the proximal connecting portion 432 at a proximal side of the elongated handle assembly 420, the trigger handle 450 may be actuated to force the push button 462, and thus, the push rod 454 a predetermined distal distance, thereby, forcing the push rod 454 forward the pre-determined distance with a pre-determined amount of force so as to move the pusher block 456 into the cartridge 322. A detailed description of a suitable trigger handle, capable of providing the force necessary to actuate the push rod 454, is disclosed in U.S. Pat. No. 5,344,061, the disclosure of which is hereby incorporated herein by reference in its entirety.

Figure 34:
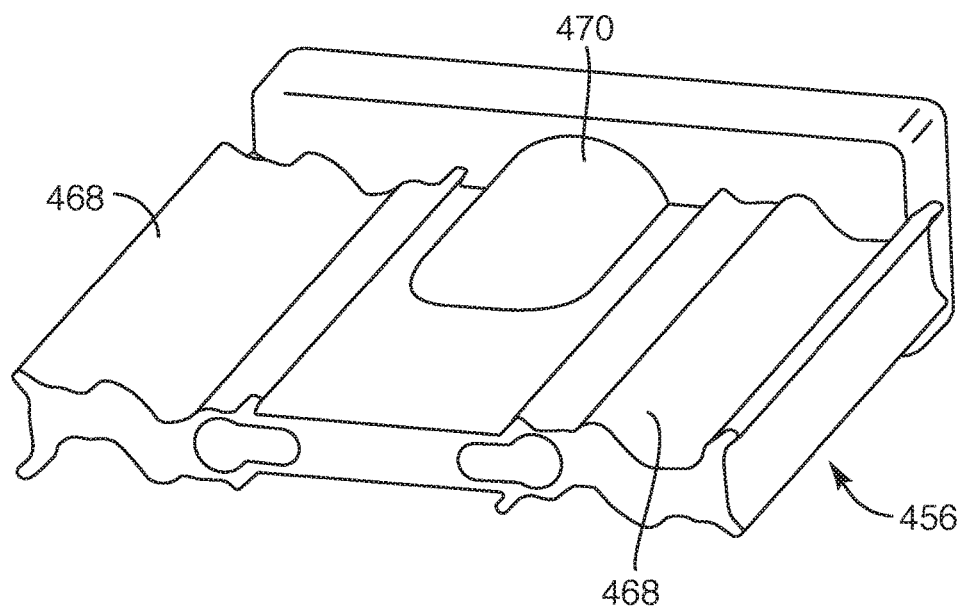
FIG. 34 is a perspective view of a pusher member, according to another embodiment of the present invention.

With respect to FIGS. 32B and 34, the pusher block 456 holds a contoured external surface 468. Such contoured external surface 468 may be shaped, sized, and configured to move through the contoured aperture 446 defined in the cartridge 322 (see FIG. 29). Further, the pusher block 456 may hold a cavity at its rear side (not shown) to couple to the push rod 454, the cavity defined within a central portion of the pusher block 456. The pusher block 456 may include an enlarged portion 470 to hold the push rod 454 therein.

Figure 37:
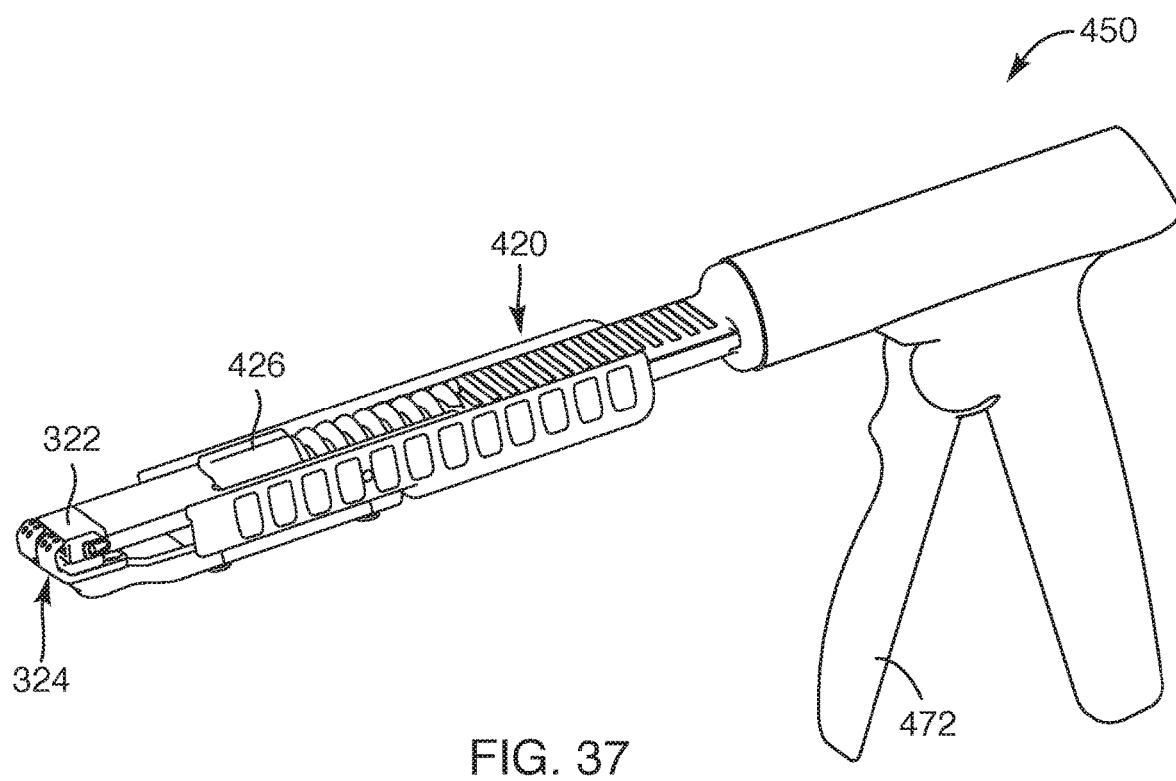
FIG. 37 is a perspective of the delivery device in a position for actuating the trigger handle, according to another embodiment of the present invention.

With respect to FIGS. 32 and 35, description of the steps of repairing severed or lacerated soft tissue will now be described. If not already pre-engaged, the physician may engage the cartridge 322 against the distal end of the pusher block housing 430 so as to be removably attached thereto via the opposing clips 438, as previously discussed. The physician may place two severed end portions within the cradle portion 324 and over the first and second plate members 306, 308 such that the severed ends are positioned over the plate coupling portion 312. The tines 372 of the first and second plate members 306, 308 may assist in holding the soft tissue end portions within the cradle portion 324. Upon the physician being satisfied with the position of the severed end portions within the cradle portion 324, the physician may rotate the turn knob 426 to move the cartridge 322 and the various pushing components distally toward the cradle portion 324. As depicted in FIG. 37, the cartridge 322 is moved to a distal position adjacent the cradle portion 324. With the cartridge in this distal position, the repair device 300 is ready to be engaged and deployed.

Figures 35, 36:
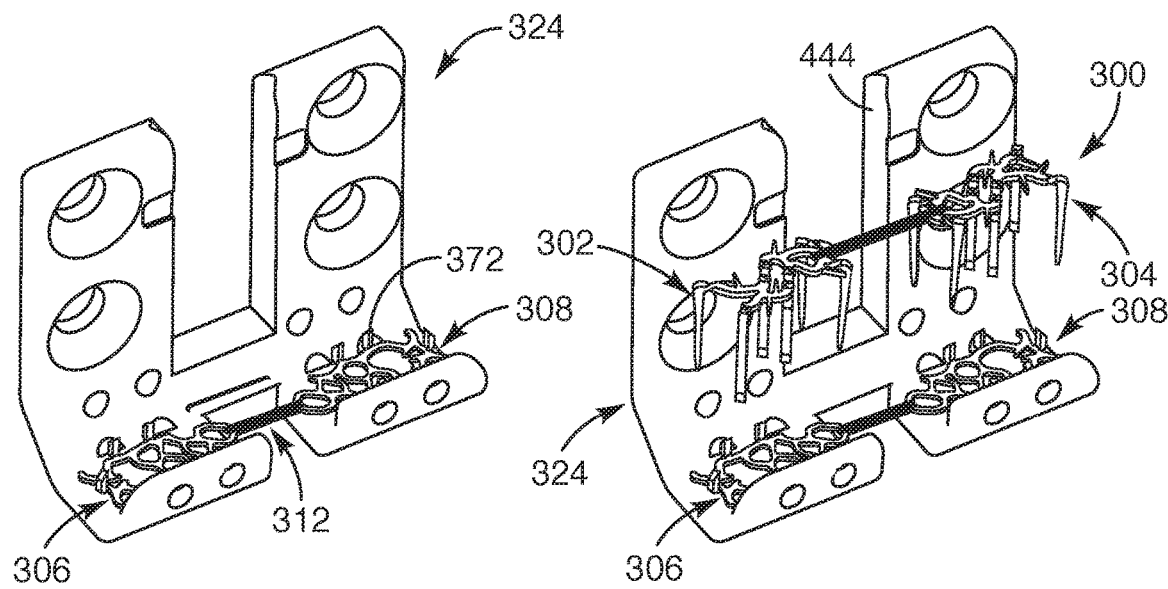
FIG. 35 is a perspective view of the first and second plate members positioned within a cradle portion, according to another embodiment of the present invention.
FIG. 36 is a perspective view of the repair device and cradle portion, depicting the first and second anchors in a pre-deployed state as positioned within the cartridge (not shown) and positioned above the first and second plate members in the cradle portion, according to another embodiment of the present invention.

With reference to FIGS. 36 and 37, the first and second anchors 302, 304 are positioned within the cartridge (cartridge not shown) in a pre-deployed state. The first and second anchors 302, 304 may be precisely aligned and positioned relative to the first and second plate members 306, 308 with the cartridge (not shown) being held within the channel 444 defined in the cradle portion via the base alignment portion 440 (FIG. 31), as previously discussed.

Figure 38:
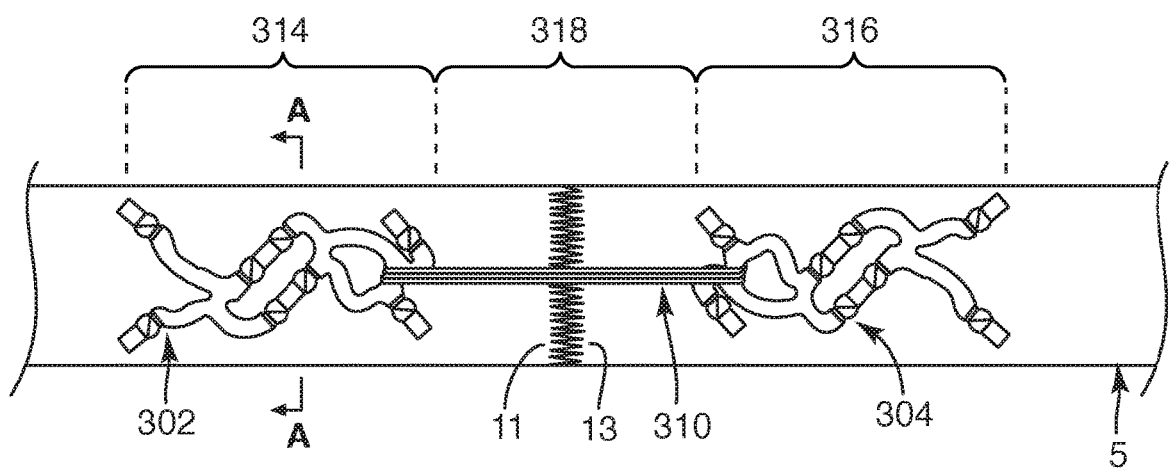
FIG. 38 is a top view of the repair device engaged with soft tissue, according to another embodiment of the present invention.
Figure 38A:
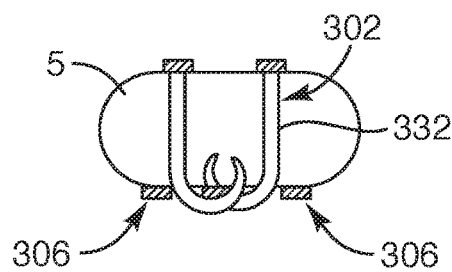
FIG. 38A is a cross-sectional view of repair device engaged with soft tissue taken along section line A-A of FIG. 38, according to another embodiment of the present invention.

At this juncture, the trigger handle 450 may be actuated via a trigger 472 of the trigger handle 450 to push the push button 462 at the proximal end of the push rod 454 (see FIG. 32A), to thereby, force the push rod 454 and pusher block 456 through the cartridge 322 to deploy the first and second anchors 302, 304 from the cartridge 322. The legs 332 of the first and second anchors 302, 304 will then be forced through the soft tissue, through notches 376 and openings 378 of the first and second plate members 306, 308 to then engage the anvil buckets 400 and be directed, via the orientation and structural characteristics of the anvil buckets 400, to curl around structure of the plate members and back through openings 378 defined within the plate members and back into the soft tissue, as depicted in FIGS. 38 and 38A. The physician may then rotate the turn knob 426 to retract the empty cartridge 322 from the cradle portion 324. The physician may then remove the elongated handle assembly 420 from the deployed repair device 300 in the soft tissue.

Figure 39:
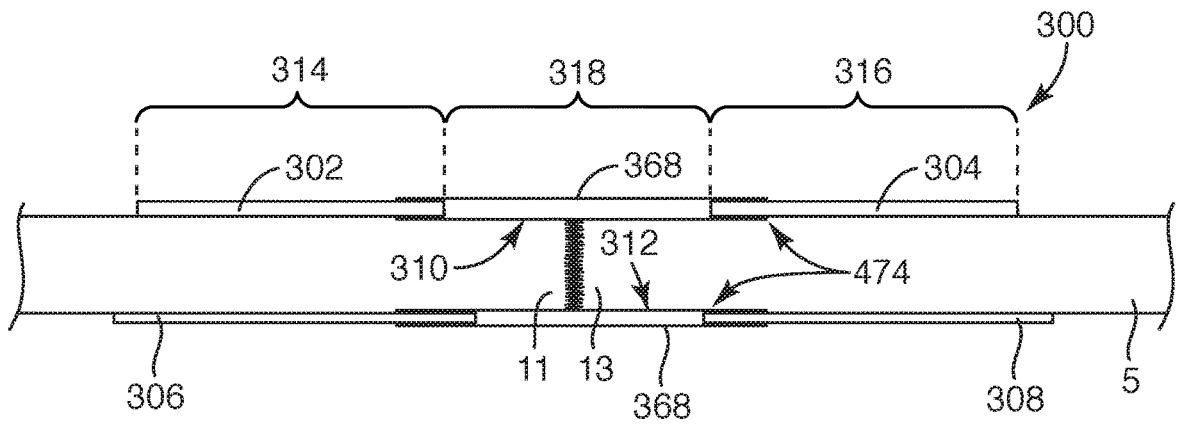
FIG. 39 is a side view of the repair device engaged with soft tissue, according to another embodiment of the present invention.

With respect to FIGS. 38, 38A, and 39, simplistic views of the repair device 300 sandwiching the soft tissue 5 is depicted. In one embodiment, the repair device 300 provides structural characteristics that facilitate healthy repair of the soft tissue 5. As previously set forth, the repair device 300 defines the first portion 314 that may elongate (so as to be moveable to a longer state), the first portion 314 including the first anchor 302 and first plate member 306. Similarly, the repair device 300 defines the second portion 316 that may elongate, the second portion 316 including the second anchor 304 coupled to the second plate member 306. Further, as previously set forth, the repair device 300 also defines an intermediate portion 318 that substantially resists elongation, the intermediate portion 318 including the anchor coupling portion 310 and the plate coupling portion 312. In this manner, the first and second portions 314, 316 of the repair device 300 facilitate healthy exercise of the soft tissue 5 (to prevent atrophy of the tendon) as the severed first and second ends 11, 13 of the soft tissue 5 maintain contact with each other with the intermediate portion 318 of the repair device 300 substantially resisting elongation.

In another embodiment, the anchor coupling portion 310 and the plate coupling portion 312 may be configured to break or fail under a high force, imposed by way of extreme activities or accident. For example, the repair device 300 may satisfactorily hold onto soft tissue under normal forces applied to the soft tissue 5. However, in the event a patient is in an accident or undergoes an activity in which a large force is applied to the treated soft tissue 5 with the repair device 300, the anchor coupling portion 310 and the plate coupling portion 312 may be designed to release or decouple should the force on the soft tissue 5 reach a pre-determined threshold force, the predetermined threshold force being less than a holding force of the repair device 300 to the soft tissue 5. As such, upon reaching a pre-determined threshold force, the anchor and plate coupling portions 310, 312 may include a mechanical link 474 designed to release or decouple the anchor and plate coupling portions 310, 312 between the respective first and second anchors 302, 304 and first and second plate members 306, 308 so as to prevent the anchors 332 from ripping through the end portions of the soft tissue 5. Should such decoupling occur, it is much easier for a physician to re-couple the first and second portions 314, 316 of the repair device 300, rather than lose valuable soft tissue length to re-attach the end portions of the soft tissue. In one embodiment, the mechanical link 474 may be the one or more filaments 368 of the anchor and plate coupling portions 310, 312. In another embodiment, the mechanical link 474 may be an additional structure, such as a ring, crimp, or latch to which the one or more filaments attach to, or some other suitable structure that is designed to de-couple upon reaching a pre-determined force. The mechanical link may be integral to and extend from one or both of the first and second anchors 302, 304 and/or the first and second plate members 306, 310.

Figure 40:
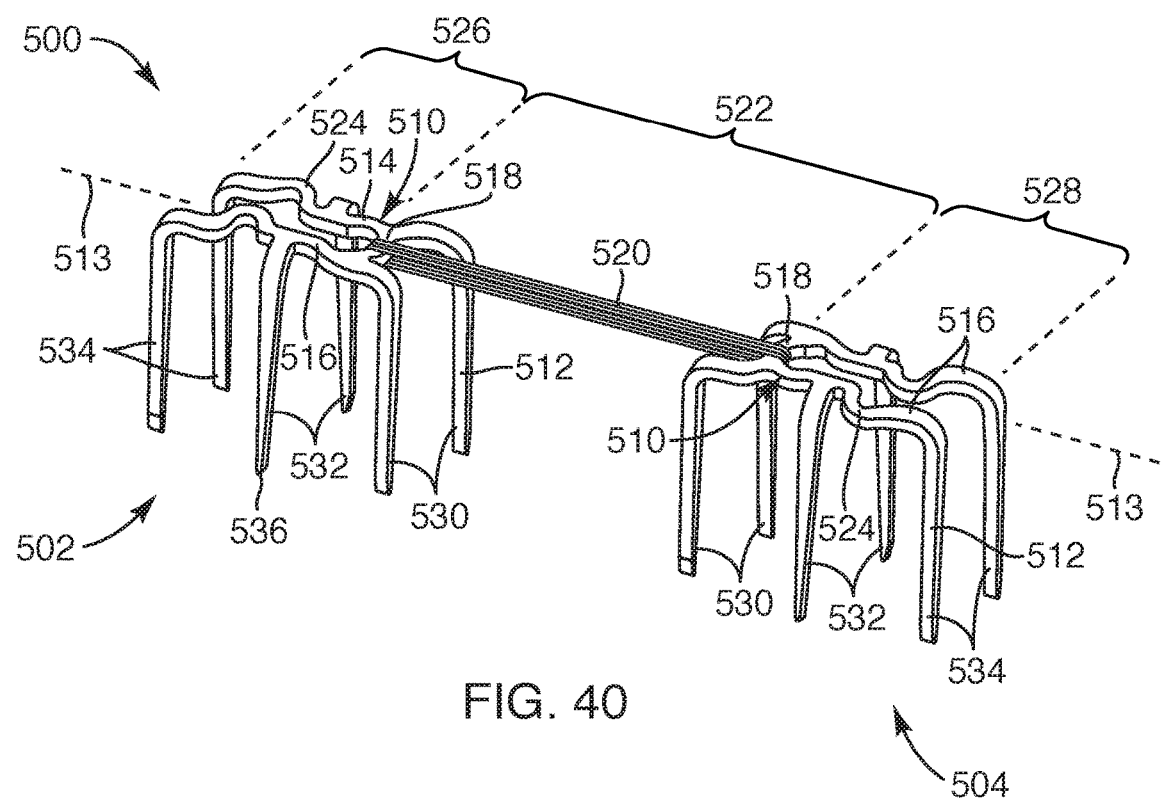
FIG. 40 is a perspective view of another embodiment of first and second anchors of a repair device, according to the present invention.
Figure 41:
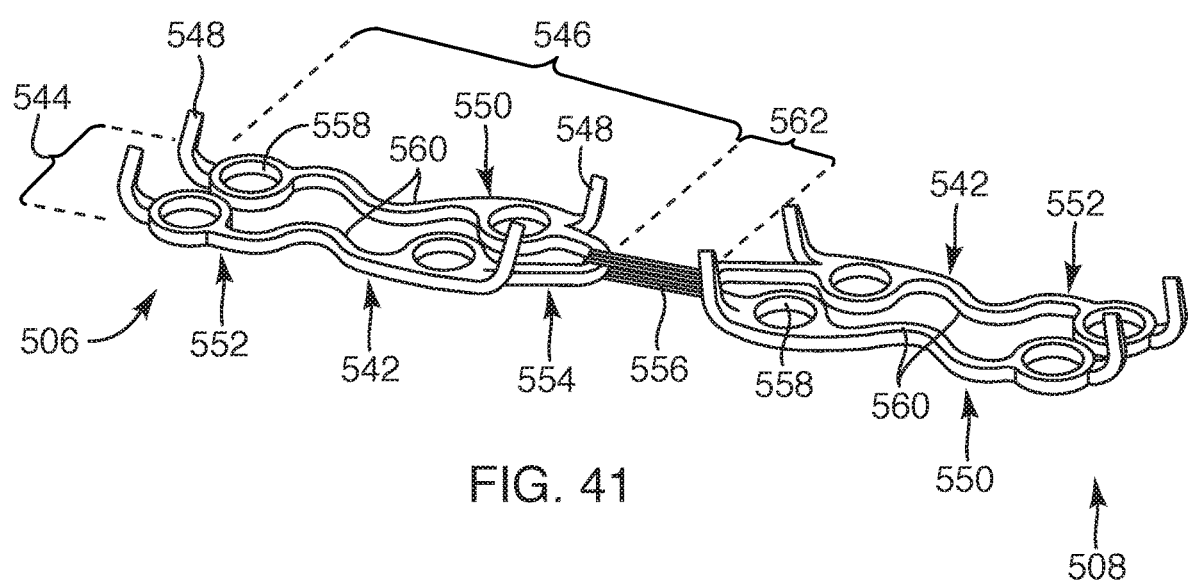
FIG. 41 is a perspective view of another embodiment of first and second plate members, according to the present invention.

Now with reference to FIGS. 40 and 41, another embodiment of first and second anchors 502, 504 and first and second plate members 506, 508 of a repair device 500 is provided. In concept, this embodiment may be similar to the embodiment depicted in FIGS. 22 and 23, except the anchors and plate members may exhibit other unique structural characteristics. With respect to FIG. 40, the first and second anchors 502, 504 may be formed from sheet material such that each of the first and second anchors 502, 504 may be unitary or a monolithically formed structure. The first and second anchors 502, 504 may each include a base portion 510 with multiple legs 512 extending from the base portion 510. The base portion 510 of each of the first and second anchors 502, 504 may extend generally within a plane. Further, the base portion 510 of the first and second anchors 502, 504 may define an axis 513 such that the first and second anchors 502, 504 may be aligned longitudinally relative to each other along the axis 513. Similar to that depicted in previous embodiments, subsequent to the first and second anchors 502, 504 being cut from sheet material, the legs 512 may be bent at their respective base to a bent position as depicted. The base portion 510 of each of the first and second anchors 502, 504 may include a first elongate portion 514 and a second elongate portion 516. The first and second elongate portions 514, 516 may be interconnected by a single lateral extending portion 518 therebetween. Each of the first and second elongate portions 514, 516 may include at least two legs extending therefrom such that each anchor may include at least four legs. In another embodiment, the first and second anchors may include six legs or more. As in previous embodiments, each of the legs 512 may extend generally or substantially perpendicular relative to a plane defined by the base portion 510 of each of the first and second anchors 502, 504.

The first and second anchors 502, 504 may be coupled together with one or more anchor filaments 520, for example, wrapped between the lateral extending portions 518 of each base portion 510 of the first and second anchors 502, 504. As in previous embodiments, the one or more anchor filaments 520 may take multiple wrappings or windings to ensure the first and second anchors 502, 504 are appropriately coupled together. The portion along the length of the repair device 500 described as the one or more anchor filaments may be referenced as a mid portion 522 of the repair device 500. Further, the first and second elongate portions 514, 516 of each of the first and second anchors 502, 504 may each include a curved portion 524 along a length thereof. The curved portion 524 may be sized and configured to facilitate the base portion 510 or the respective first and second elongate portions 514, 516 to stretch or elongate relative to the mid portion 522 so as to move toward a linear configuration upon a force being applied thereto. In this manner, similar to previous embodiments, this embodiment may provide for first and second end portions 526, 528 of the repair device 500 to elongate along a length of the repair device 500 with the mid portion 522 of the repair device 500 sized and configured to minimize elongation of the repair device 500.

Furthermore, each of the first and second anchors 502, 504 may define multiple pairs of legs 512, such as, inner legs 530, middle legs 532 and outer legs 534, the inner legs 530 being closer to the repair site and the outer legs 534 being furthest from the repair site and the middle legs 532 being between the inner legs 530 and the outer legs 534. Each of the inner legs 530, middle legs 532 and outer legs 534 having one leg extending from one of the first and second elongate portions 514, 516 of the first and second anchors 502, 504. The lateral extending portion 518 that connects the first and second elongate portions 514, 516 may extend between the inner legs 530 and the middle legs 532 such that the lateral extending portion 518 may be set back from the inner legs 530. Further, each of the legs 512 extending from the first elongate portion 514 may be described as first legs and each of the legs 512 extending from the second elongate portion may be described as second legs. In one embodiment, the first legs may be aligned and the second legs may be aligned such that the tips 536 or free ends of the first legs are substantially aligned and the tips 536 or free ends of the second legs are substantially aligned.

Figure 49:
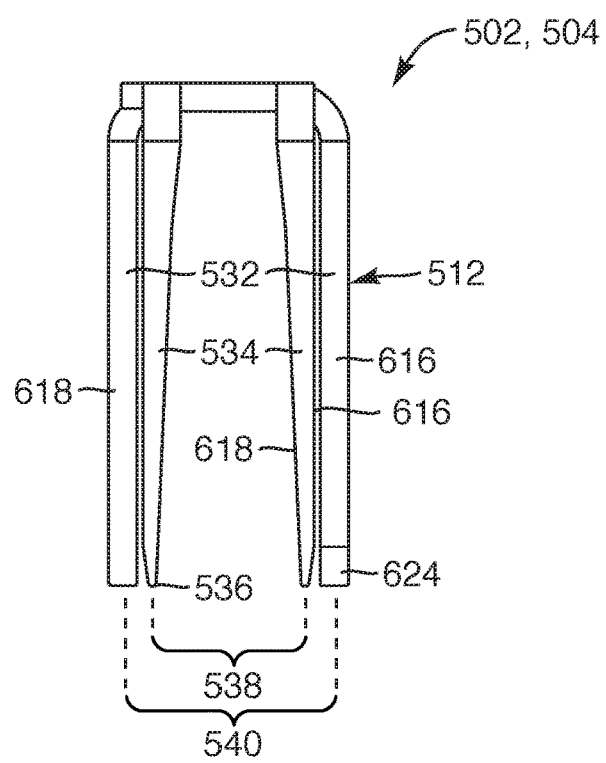
FIG. 49 is an end view of one of the anchors, according to another embodiment of the present invention.

In another embodiment, the tips 536 or free ends of the first legs may be laterally spaced relative to the axis 513 at different distances relative to each other. The tips or free ends of the second legs may also be laterally spaced relative to the axis 513 at different distances relative to each other. In another embodiment, spacing between each of the inner legs 530, middle legs 532, and outer legs 534 may be similar, but may be offset relative to each other. In still another embodiment, spacing between the inner legs 530 and outer legs 534 may be similar and the middle legs 532 may be narrower or wider than the inner legs 530 and outer legs 534. Such varying spacing or offset leg pairs may result in the tips of the first legs and the second legs to enter the soft tissue at varying lateral positions relative to an axis of the soft tissue (not shown) to gather varying longitudinal tissue bundles, upon deploying and fixating the repair device 500 to the soft tissue, such as a tendon or ligament. For example, FIG. 49 is an end view of one of the first and second anchor 502, 504, depicting the outer legs 534 having a first spacing 538 and the middle legs 532 having a second spacing 540. In one embodiment, the second spacing 540 may be wider than the first spacing 538.

With reference to FIG. 41, the first and second plate members 506, 508 of this embodiment may each include a main body 542 having a periphery or peripheral sides extending to define opposite face surfaces or sides of the main body 542. The opposing face surfaces of the main body 542 of the first and second plate members 506, 508 may be generally planar so as to exhibit flat members. The first and second plate members 506, 508 may be referenced as a substrate or backing member to the repair device 500. The periphery of the main body 542 may define inner and outer peripheral portions that may extend to exhibit a generally u-shaped configuration such that portions of the u-shaped configuration may exhibit radial portions or curved portions 560. The first and second plate members 506, 508 may each define a width 544 and a length 546. Further, the first and second plate members 506, 508 may include tines 548 extending transverse relative to the planar main body 542 and sized and configured to pierce and extend into tissue.

In one embodiment, the tines 548 of the first and second plate members 506, 508 may be canted toward the repair site. In another embodiment, the tines 548 may be canted away from the repair site. In still another embodiment, the tines 548 may extend substantially perpendicular relative to the plate members. But for the tines, the first and second plate members 506, 508 may extend in a plane or be substantially flat. As in previous embodiments, the first and second plate members 506, 508 may each be a monolithically formed structure with the tines 548 bent transverse relative to the main body 542. Further, the first and second plate members 506, 508 may be cut from a sheet material and, as such, the cut sheet material may be flat and plate like and further, the first and second plate members 506, 508 may exhibit a square or rectangular cross-section. The first and second plate members 506, 508 may be formed from, for example, a metallic material, such as stainless steel or any other suitable medical grade material, and be cut from sheet material by laser cutting or any other suitable cutting technique known by one of ordinary skill in the art.

Each of the first and second plate members 506, 508 may include first and second elongated portions 550, 552 extending from a base end 554. At each base end 554 of the first and second plate members 506, 508, one or more plate filaments 556 may be employed to couple the first plate member 506 to the second plate member 508. Further, the first and second elongated portions 550, 552 may each define one or more apertures 558 therein and/or one or more curved portions 560. The apertures 558 and/or the curved portions 560 may be sized and configured to receive and be captured by the legs 512 of the first and second anchors 502, 504, described in further detail herein and similar to that described in previous embodiments. Further, the curved portions 560 may be sized so as to facilitate the first and second plate members 506, 508 to elongate or move to a more linear position so that the length of the first and second plate members 506, 508 elongates so as to become longer. In this manner, similar to the first and second anchors 502, 504, upon a load being placed upon the repair device 500, the first and second plate members 506, 508 may elongate while a mid portion 562 defined by, for example, the one or more plate filaments, resists elongation to maintain a substantially fixed position.

Figure 42:
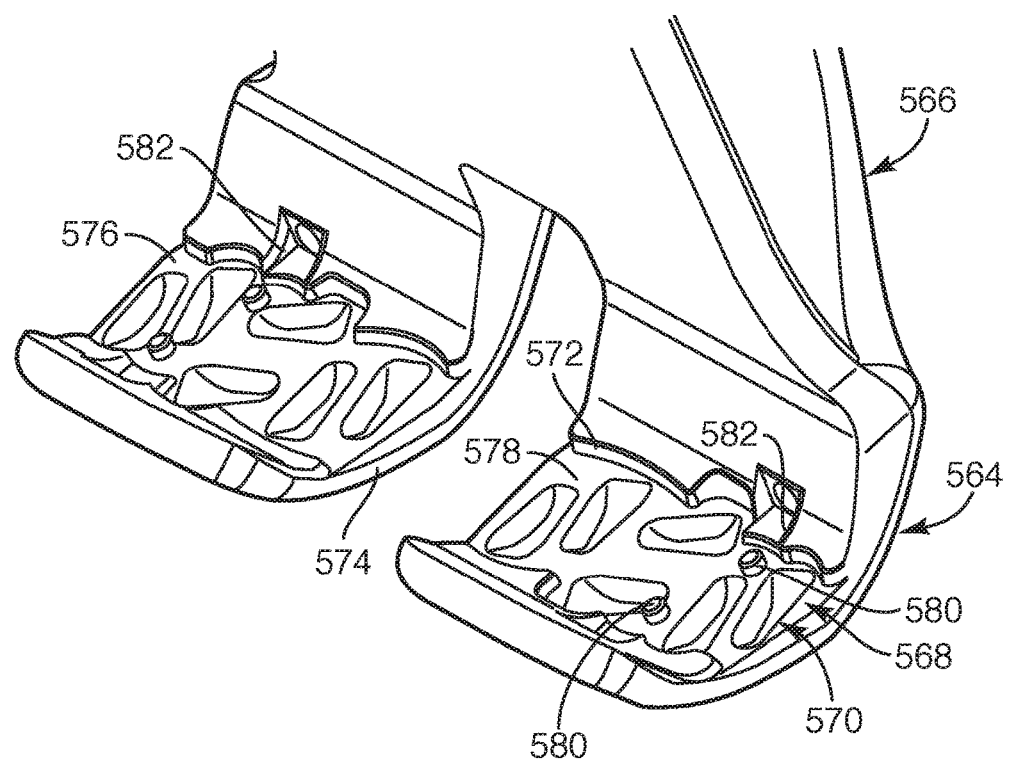
FIG. 42 is a perspective view of another embodiment of a cradle portion, according to the present invention.
Figure 43:
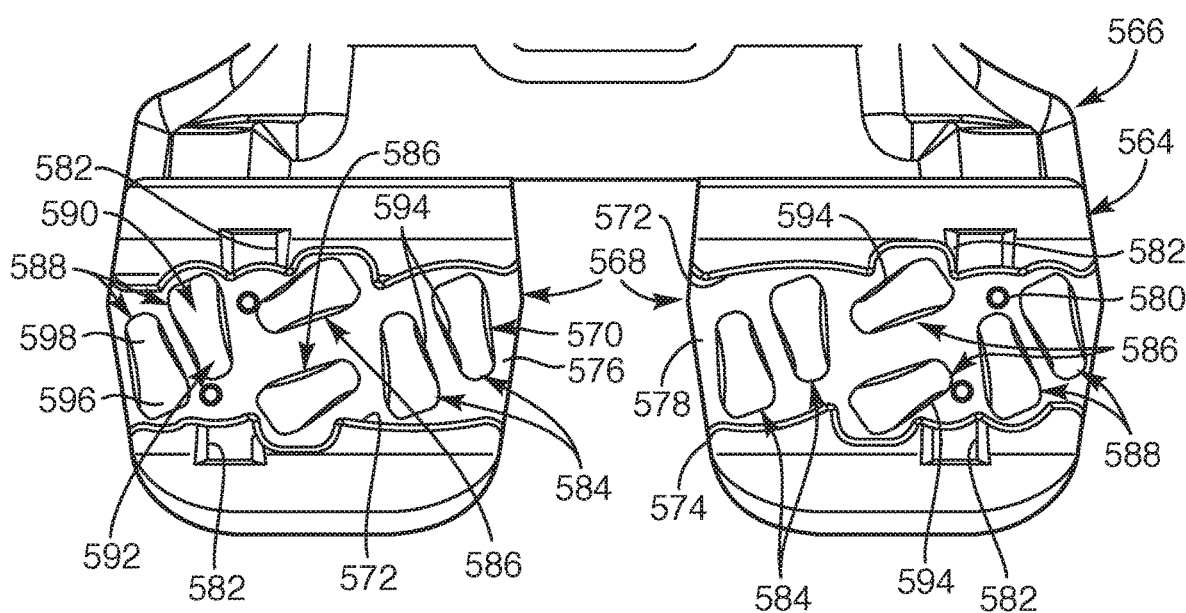
FIG. 43 is a top view of the cradle portion of FIG. 42, according to another embodiment of the present invention.

With respect to FIGS. 42 and 43, similar to embodiments described in FIG. 27, the before-described first and second plate members 506, 508 (FIG. 41) may be positioned in a cradle portion 564 of a cradle 566 of a delivery device (not shown). The cradle portion 564 of this embodiment may include a bed surface 568 with anvil buckets 570 defined in the bed surface 568. The bed surface 568 may be defined by a peripheral wall 572 sized and configured with contours shaped to receive the first and second plate members 506, 508. The bed surface 568 may be separated with a channel or window 574 defined in the cradle portion 564 so as to separate the bed surface 568 and cradle portion 564 into separate parts or two portions, for example, a first bed surface 576 and a second bed surface 578. The window 574 may provide two functions, such as, increasing the viewability of the repair site as well as providing a relief for the ends of the soft tissue being fixated so that any potential trumpeting of the tissue ends maintain a localized position.

Further, the bed surface 568 may include pins 580 separately formed and set within apertures defined in the bed surface 568. The apertures may be machined or pre-formed so that the pins 580 may be inserted through the underside of the cradle portion 564 and positioned within the apertures so as to extend from the bed surface 568 to about the height of the peripheral wall 572. The pins 580 may include a crimp or taper or bevel so that upon positioning within their corresponding aperture, the pins 580 are maintained with an interference fit. The cradle portion 564 may also define multiple holes 582 extending therethrough. Such holes 582 may be used to facilitate temporarily holding (via one or more filaments (not shown)) the first and second plate members 506, 508 against the bed surface 568 of the cradle portion 564.

The first and second bed surfaces 576, 578 may each include multiple anvil buckets 570. In one embodiment, the anvil buckets 570 may be separated so as to define pairs of anvil buckets 570. For example, each of the first and second bed surfaces 576, 578 may include pairs of anvil buckets 570 defined as inner anvil buckets 584, middle anvil buckets 586, and outer anvil buckets 588. Each pair of anvil buckets 570 relative to one of the first and second bed surfaces 576, 578 may be unique relative to any other anvil bucket pair. In another embodiment, the anvil bucket pairs may be similar or substantially the same as other anvil bucket pairs defined in the first and second bed surfaces. The similarity or differences may be dependent upon a configuration of the first and second anchors 502, 504 (FIG. 40) such that each anvil bucket 570 may be sized and configured to correspond with one of the legs 512 of the first and second anchors 502, 504.

Figure 44:
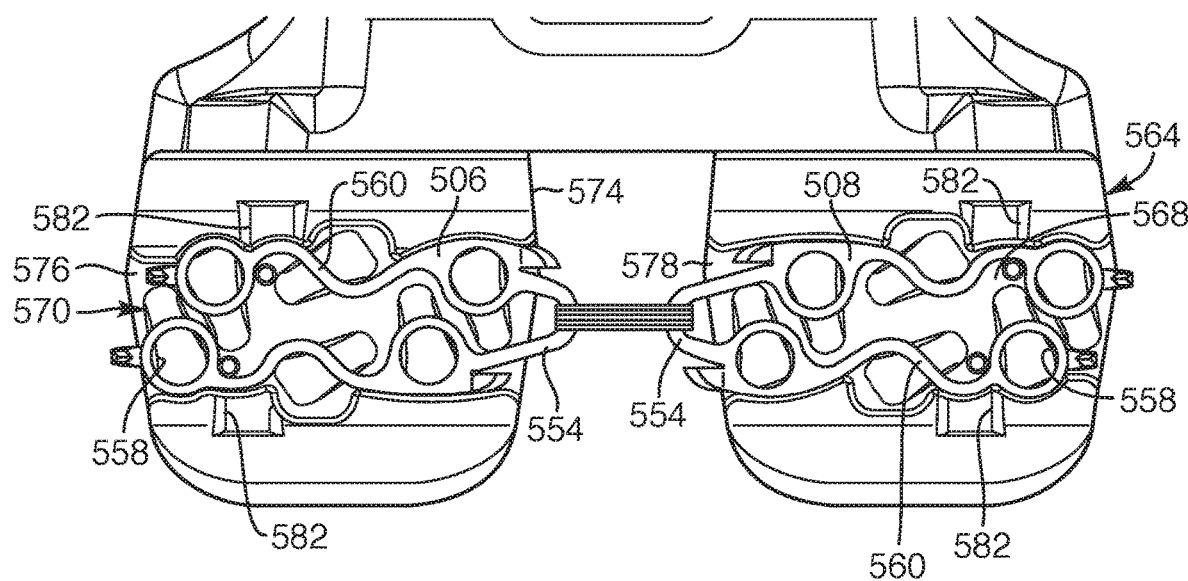
FIG. 44 is a top view of the first and second plate members positioned in the cradle portion, according to another embodiment of the present invention.

Now with reference to FIG. 44, the first and second plate members 506, 508 may be positioned on the cradle portion 564 and within the bed surface 568. The pins 580 and the contours of the peripheral wall 572 defining the bed surface 568 may assist in aligning and holding the first and second plate members 506, 508 at an appropriate position within the cradle portion 564. Further, the one or more apertures 558 and/or curved portions 560 of each of the first and second plate members 506, 508 may be positioned over a mid-portion of the anvil buckets 570 defined in the bed surface 568. The base end 554 of each of the first and second plate members 506, 508 may at least partially extend beyond the bed surface 568 so as to hang over the window 574 of the cradle portion 564. Once the first and second plate members 506, 508 are positioned within the respective first and second bed surfaces 576, 578, the one or more wires or filaments (not shown) may extend through the holes 582 and over the first and second plate members 506, 508 to ensure the plate members do not lift from the cradle portion 564.

Figure 45:
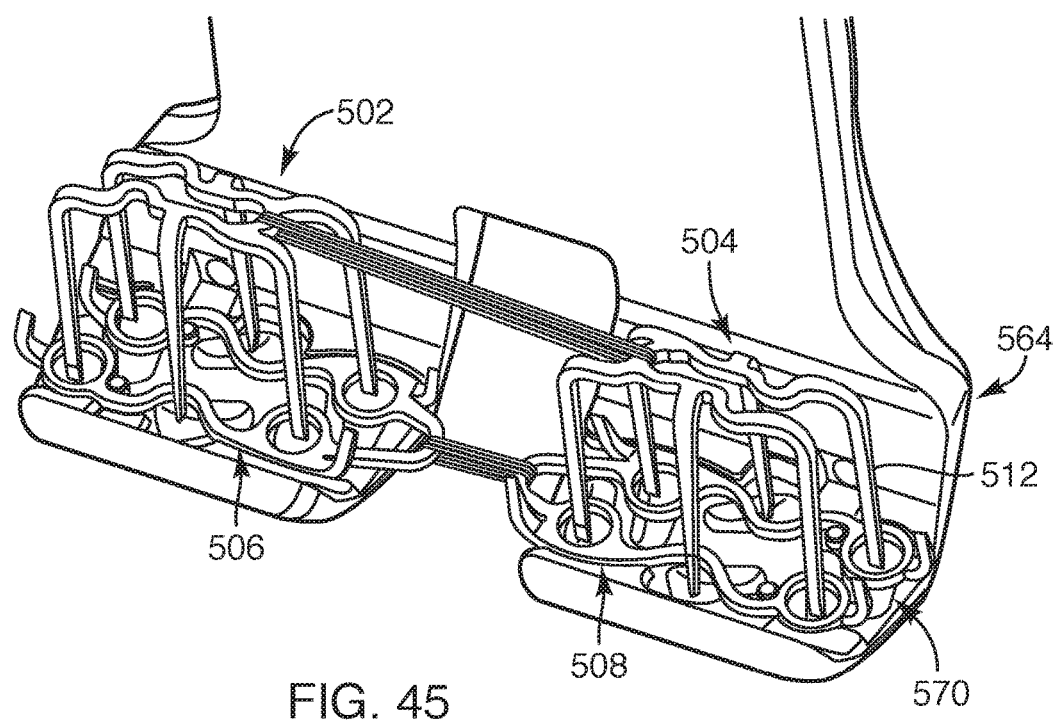
FIG. 45 is a perspective view of a repair device, depicting the first and second anchors positioned above the respective first and second plate members, according to another embodiment of the present invention.

With respect to FIGS. 43 and 45, the first and second anchors 502, 504 and the first and second plate members 506, 508 are depicted in a position just prior to the legs of the anchors engaging with the anvil buckets 570. As depicted, each anvil bucket 570 may be positioned in the cradle portion 564 to correspond with one of the legs 512 of the first and second anchors 502, 504. Upon positioning the first and second plate members 506, 508 in the cradle portion 564 as previously described, portions of the first and second plate members 506, 508 extend over the anvil buckets 570 so as to be positioned and to correspond with the legs 512 of the first and second anchors 502, 504. Similar to that described in earlier embodiments, the anvil buckets 570 may be sized and configured to receive the legs 512 of the first and second anchors 502, 504 to facilitate the legs 512 to bend and wrap around portions of the first and second plate members 506, 508 that extend over the anvil buckets 570.

Such anvil buckets 570 may include a receiving portion 590 and an exit portion 592 that manipulates the legs 512 in a pre-determined direction and orientation. Further, each of the anvil buckets 570 may include an engaging side wall 594 that extends between the receiving portion 590 and the exit portion 592 of the anvil buckets 570 so as to manipulate the legs 512 in such pre-determined direction and orientation. The engaging side wall 594 may extend transverse relative to the bed surface 568 at, for example, an angle extending at about 75-105 degrees or 80-100 degrees. In regard to the inner and outer anvil buckets 584, 588, the engaging side wall 594 may be the inner or adjacent side walls of the anvil bucket pairs. In regard to the middle anvil buckets 586, the engaging side wall 594 may be the outer side walls relative to the anvil bucket pairs. The receiving portion 590 of the anvil buckets 570 may include a descending, sloped floor 596 and the exit portion 592 of the anvil buckets 570 may include an ascending, sloped floor 598 so that the legs 512 may pierce back into tissue. Further, the receiving portion 590 may define a larger surface area than the exit portion 592. In this manner, the anvil buckets 570 may be sized and configured to manipulate the curling or wrapping of the legs 512 of the first and second anchors 502, 504 around portions of the respective first and second plate members 506, 508 in a substantially consistent fashion.

Figure 46:
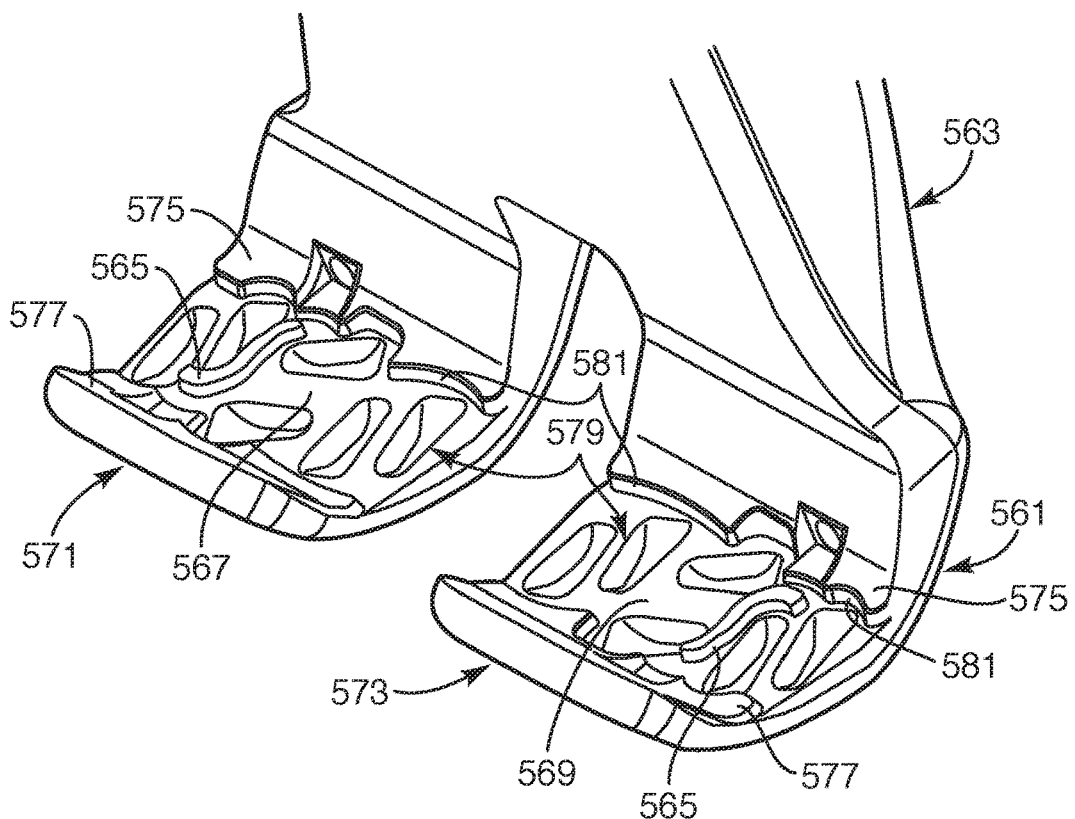
FIG. 46 is a perspective view of another embodiment of a cradle portion, according to the present invention.
Figure 47:
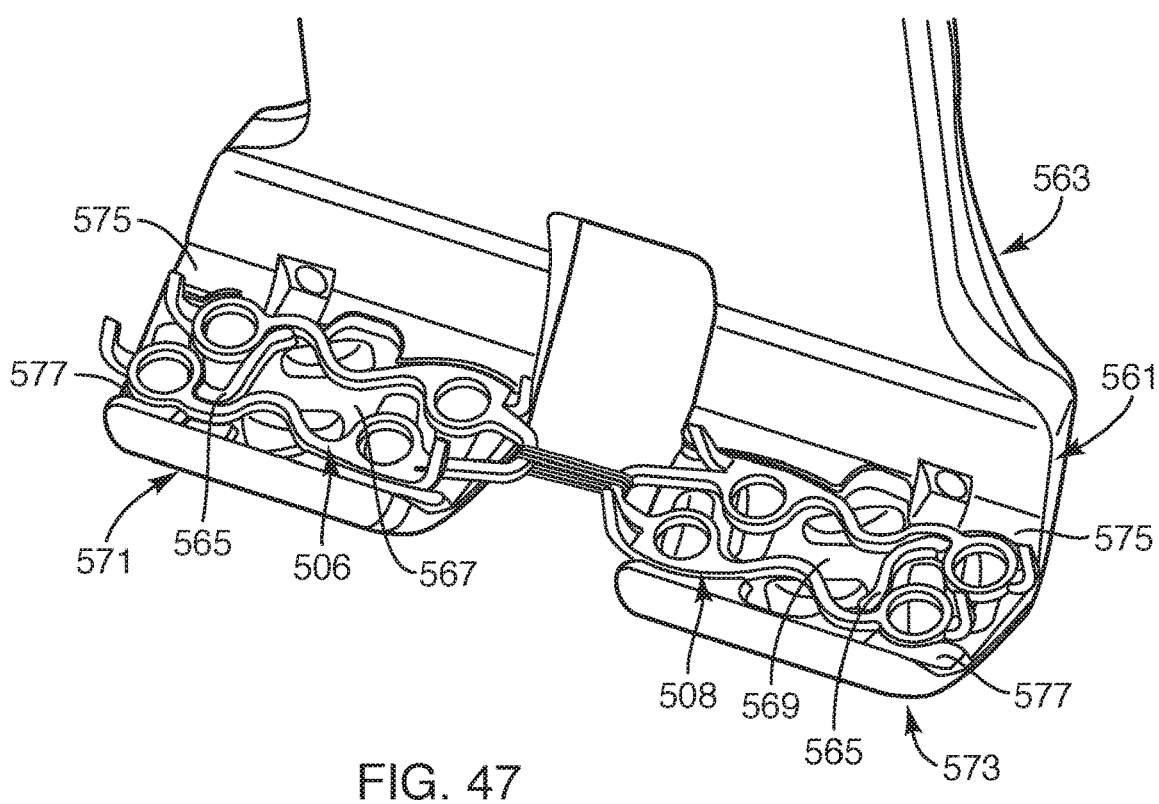
FIG. 47 is a perspective view of the cradle portion of FIG. 46, depicting first and second plate members positioned over the cradle portion, according to another embodiment of the present invention.

With respect to FIG. 46, another embodiment of a cradle portion 561 of a cradle 563 is depicted. In this embodiment, instead of the before described pins 580 (FIG. 42) extending from the bed surface, one or more islands 565 or one or more protrusions extending from a first bed surface 567 and a second bed surface 569 of the cradle portion 561 are provided, this embodiment of the cradle 563 being similar in all other aspects previously described for the cradle/cradle portion. As in previous embodiments, the cradle portion 561 may be separated between a first part 571 and a second part 573, each of the first and second parts 571, 573 having at least one of the islands 565 defined in the first bed surface 567 and the second bed surface 569. In one embodiment, a single island 565 may extend as a protrusion or raised structure from each of the first bed surface 567 and the second bed surface 569. In another embodiment, each island 565 may extend with an 5-configuration or similar configuration, such as a L-configuration or the like. Such islands 565 may be positioned and extend adjacent to a first lateral side 575 of the bed surface to adjacent a second lateral side 577 of the bed surface and extend alongside multiple ones of anvil buckets 579 defined in each of the first and second bed surfaces 567, 569, as previously described. The first and second lateral sides 575, 575 of the bed surface may be defined by a peripheral wall 581 raised above each of the first and second bed surfaces 567, 569. The islands 565 may extend with a height similar to the peripheral wall 581 or may extend higher than such peripheral wall 581. As depicted in FIGS. 46 and 47, similar to the before described pins, the islands 565, in combination with the peripheral wall 581, may stabilize and prevent movement, laterally and longitudinally, of the first plate member 506 and the second plate member 508 within the respective first and second bed surfaces 567, 569 of the cradle portion 561. In this manner, the islands 565 may be positioned within the first and second bed surfaces 567, 569 to directly contact inner sides of the first and second plate members 506, 508 positioned in the cradle portion 561. The islands may be formed integrally with the cradle portion 561 or may be formed as separate components and attached similarly as the pins such that the islands 565 may include extensions/pins extending from an underside of the islands to couple to holes bored therein. As such, the islands 565 may be formed with the cradle 563 employing machining or molding techniques as known to one of ordinary skill in the art.

Figure 48:
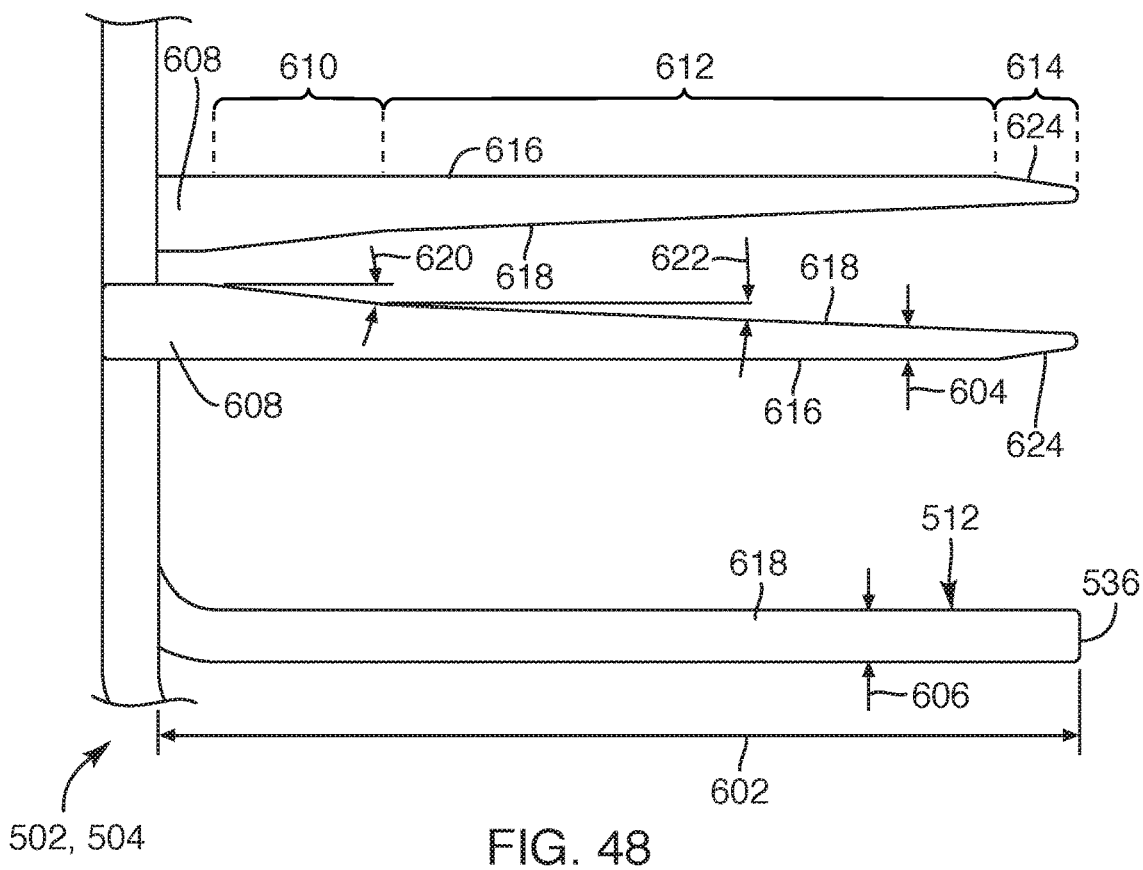
FIG. 48 is an enlarged side view of some of the legs of the first anchors, according to another embodiment of the present invention.

With respect to FIG. 48, an enlarged profile view of some of the legs 512 of one of the first and second anchors 502, 504 is provided. With reference to FIGS. 48 and 49, the legs 512 may each include a length 602, a width 604, and a thickness 606, the length 602 being longer than each of the width 604 and the thickness 606 and the thickness 606 being a substantially constant thickness. The width 604 may include a varying dimension along the length 602 of a given leg. Each leg may include a base portion 608, a first tapered portion 610, a second tapered portion 612, and a third tapered portion 614 such that the width 604 may vary along the length 602. The base portion 608 may include a substantially constant width 604. The first tapered portion 610 may include a first tapering width between the base portion 608 and the second tapered portion 612. The second tapered portion 612 may include a second tapering width between the first tapered portion 610 and the third tapered portion 614. The second tapered portion 612 may include a third tapering width extending between the second tapered portion 612 and a free end or the tip 536 of the leg 512. The second tapered portion 612 may be longer than the first and third tapered portions 610, 614. The first tapered portion 610 may be longer than the third tapered portion 614. The free end or tip 536 of a give leg 512 may include a radius or rounded surface end.

Further, the width 604 of each leg 512 may be defined by a first surface 616 and a second surface 618. In one embodiment, the first surface 616 may be substantially planar or continuous along the base portion 608, the first tapered portion 610, and the second tapered portion 612. The first surface 616 along the third tapered portion 614 may be angled so as to provide an engaging surface 624. This engaging surface 624, along with the tip 536 may be sized and configured to engage the anvil buckets 570 (FIG. 43). The second surface 618 may include one or more sloping angles to provide a varying width or taper along the length 602 of each leg 512. For example, in one embodiment, the second surface 618 of the first tapered portion 610 may include a slope at a first angle 620 and the second surface 618 of the second tapered portion 612 and the third tapered portion 614 may include a slope at a second angle 622. The second surface 618 along the second tapered portion 612 and the third tapered portion 614 may be sloped and extend continuously or planar. In this manner, the second surface 618 of the legs 512 may be sloped from the base portion 608 and along the first, second, and third tapered portions 610, 612, 614 so that the legs 512 taper from the base portion 608 to the tip 536. With this arrangement, upon the legs 512 of the first and second anchors 502, 504 being forced through the tissue and then against the anvil buckets (now shown), such varying width of the legs 512 may be sized so as to manipulate the legs to consistently extend back into the tissue in a curling manner without buckling or bending inappropriately. In another embodiment, the first surface 616 and the second surface 618 may include one or more slopes to provide one or more tapers along the length of the legs 512. In still another embodiment, each leg 512 may include substantially similar dimensions of its respective length 602, width 604, and thickness 606, but may be oriented about the longitudinal axis of a given leg so that the engaging surface 624 of each leg may be oriented 90 degrees to 180 degrees relative to the engaging surface 624 of adjacent legs or other legs of a given anchor. In this manner, such engaging surface 624 of the legs 512 may be oriented and positioned consistent with and relative to orientations of corresponding anvil buckets 570 defined in the bed surface of the cradle portion 564 (see FIG. 45).

In one embodiment, the second angle 622 defined by the slope of the second surface 618 along the second tapered portion 612 and the third tapered portion 614 may be in the range between about 1 degree and 10 degrees and preferably between about 1 degree and 5 degrees. For example, the second surface 618 may slope with the second angle 622 being about 2.6 degrees. In another embodiment, the first surface 616 and the second surface 618 may each slope so as to taper at an angle of about 1.3 degrees. Dependent upon the tissue to which the anchors are to be fixated, the length 602 of the legs 512 may vary. In the case of fixating the anchors to a flexor tendon or the like, the length 602 of the legs 512 may be about 0.2 inches or between about 0.15 and 0.25 inches. The length of the second tapered portion 612 may be about 0.13 inches or between about 0.10 to 0.2 inches. The width 604 of the second tapered portion 612 may taper from about 0.012 to 0.006 inches so as to have a 2:1 ratio in width change along the length of the second tapered portion 612. This width change ratio for the second tapered portion 612 may be in the range of about 1.5:1 ratio to a 5:1 ratio dependent upon the length of the legs 512, which also may be dependent upon the tissue thickness/diameter. Such dimensions of the second tapered portion 612 of the legs 512 facilitate the legs to curl appropriately and minimize the probability of buckling in the legs.

Figure 50:
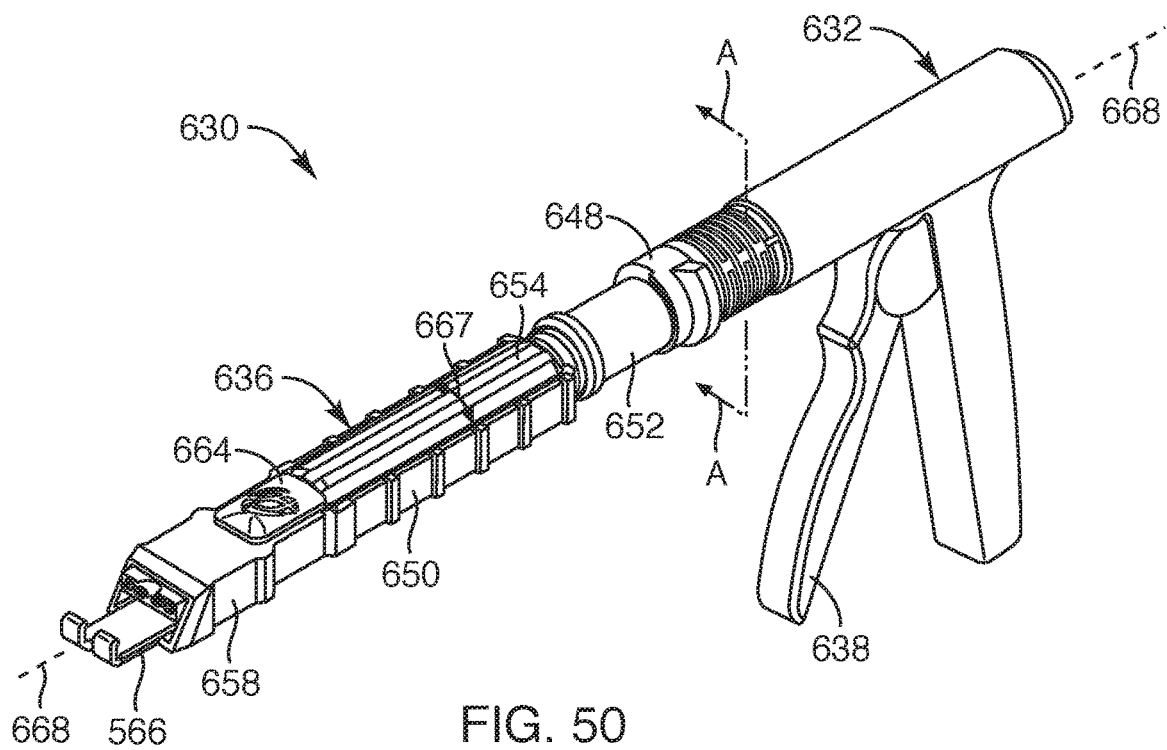
FIG. 50 is a perspective view of a delivery device, according to another embodiment of the present invention.
Figure 51:
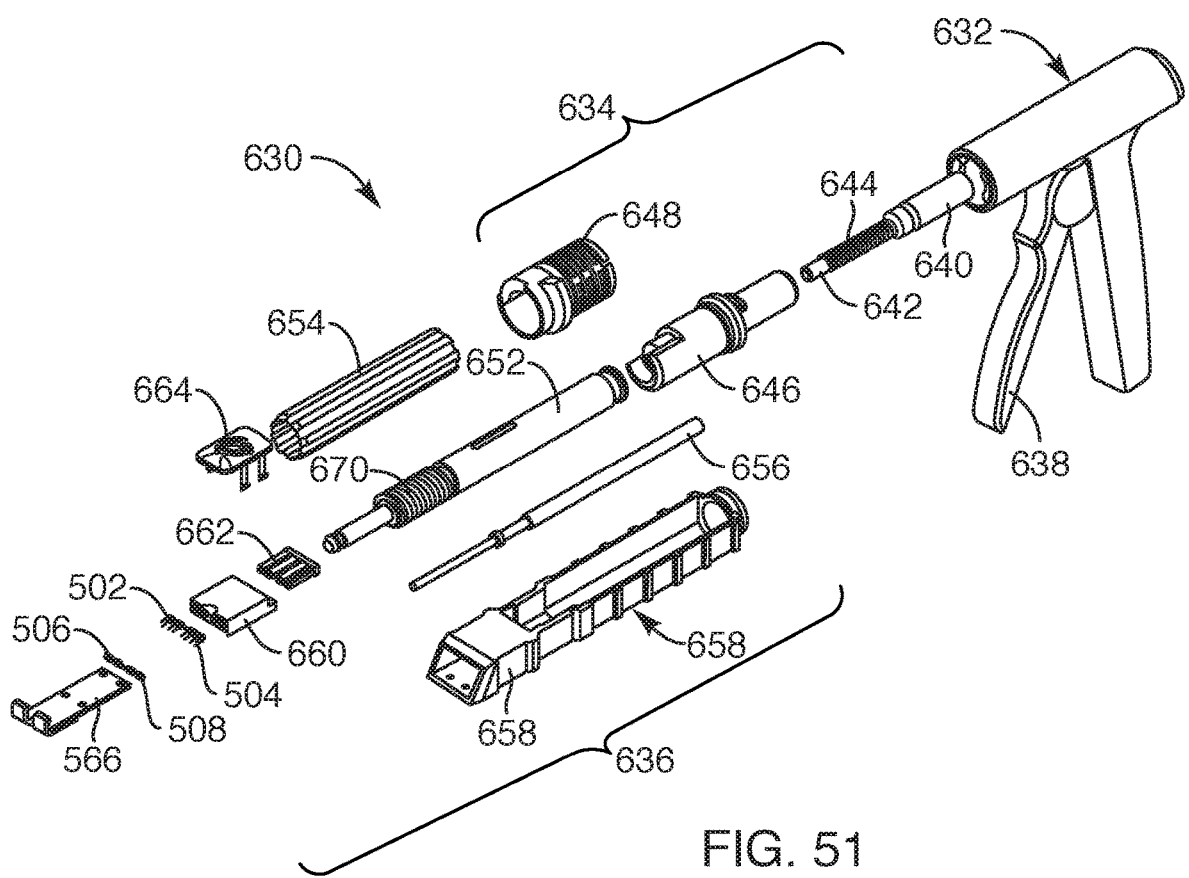
FIG. 51 is an exploded view of various components of the delivery device, according to another embodiment of the present invention.

Now with reference to FIGS. 50, 51, and 52, one embodiment of a delivery device 630 will now be described. The delivery device 630 of this embodiment is similar to earlier embodiments of the delivery device depicted in FIGS. 32 and 37. In this embodiment, the delivery device 630 may include a trigger gun 632, an adapter assembly 634, and an applicator assembly 636. The trigger gun 632 may include a trigger 638 such that the trigger gun 632 provides a force for delivering the first and second anchors 502, 504, as previously described. On example of a trigger gun 632 configured to deliver a force by compressing the trigger 638 is described in U.S. Pat. No. 5,344,061, the disclosure of which is hereby incorporated herein by reference in its entirety.

The adapter assembly 634 may be coupled between the trigger gun 632 and the applicator assembly 636. The components of the adapter assembly 634 may include a stroke regulator 640, a push rod 642, a return spring 644, an adapter tube 646, and a slide lock 648. The stroke regulator 640 may also be referenced as a force regulator or a trigger regulator. The stroke regulator 640 may be configured to ensure that the trigger 638 completes a full trigger stroke before returning to its original position and to ensure that the first and second anchors 502, 504 are fully deployed. The stroke regulator 640 may be, for example, an elastomer material sized to compress under a predetermined force to complete or allow for a full trigger stroke such that, upon making the full trigger stroke, such may be indicated with, for example, a click or another indicator, such as the trigger handle returning to its original position. The click or returned trigger position being an indicator for making the full trigger stroke and fully clamping the repair device to soft tissue. The push rod 642 may be coupled to the stroke regulator 640 and may be positioned within the adapter tube 646 with the return spring 644 extending around a portion of the push rod 642. The slide lock 648 may be positioned around a distal portion of the adapter tube 646 such that the distal end of the adapter tube 646 interlocks with a proximal end of the adapter assembly 634.

The applicator assembly 636 may include many of the same components of the applicator assembly or elongated assembly of previous embodiments. For example, the applicator assembly 636 may include an applicator handle 650 that houses a worm drive 652, a thumb wheel 654, and the applicator push rod 656. The applicator handle 650 may include a distal housing 658 that houses a cartridge 660 and a pusher member 662, the pusher member 662 abutting the end of the applicator push rod 656. Further, the applicator assembly 636 includes the cradle 566 with a proximal portion fixed to an internal surface of the distal housing 658. The cartridge 660 may include an internal surface shaped to correspond with a top periphery profile of the first and second anchors 502, 504 so that the first and second anchors may be positioned within a distal portion of the cartridge 660 with the pusher member 662 positioned within the cartridge 660 directly adjacent and proximal the first and second anchors 502, 504. Further, a worm drive cover 664 may be positioned proximal the distal housing 658 to cover a portion of the worm drive 652.

Upon rotating the thumb wheel 654, all components of the delivery device 630 are linearly moveable, except for the applicator handle 650 and the cradle 566. As indicated by rotation arrow 667, the thumb wheel 654 rotates, but also remains linearly stationary. The thumb wheel 654 may be tubular and may rotate about an axis 668 of the applicator assembly 636. The thumb wheel 654 may include threads 670 or a protrusion along an internal surface thereof which corresponds with the threads 670 along an external surface of the worm drive 652 to facilitate linear movement of the cartridge 660 (and other components previously set forth) along the axis 668 of the applicator assembly 636. Further, the thumb wheel 654 may include an internal surface sized to interact with a flexible wire (not shown) extending from, for example, the worm drive 652 sized and configured to limit the force of a distal end of the cartridge 660 pressed against the soft tissue. In other words, the applicator assembly 636 may include a force limiter (not shown) or torque limiter that, upon rotating the thumb wheel to linearly move the applicator assembly 636 toward the cradle portion and upon the cartridge 660 making contact with the soft tissue in the cradle portion, the force limiter may facilitate obtaining a consistent pressure or force applied to the soft tissue prior to deploying the anchors from the cartridge 660.

Figure 51A:
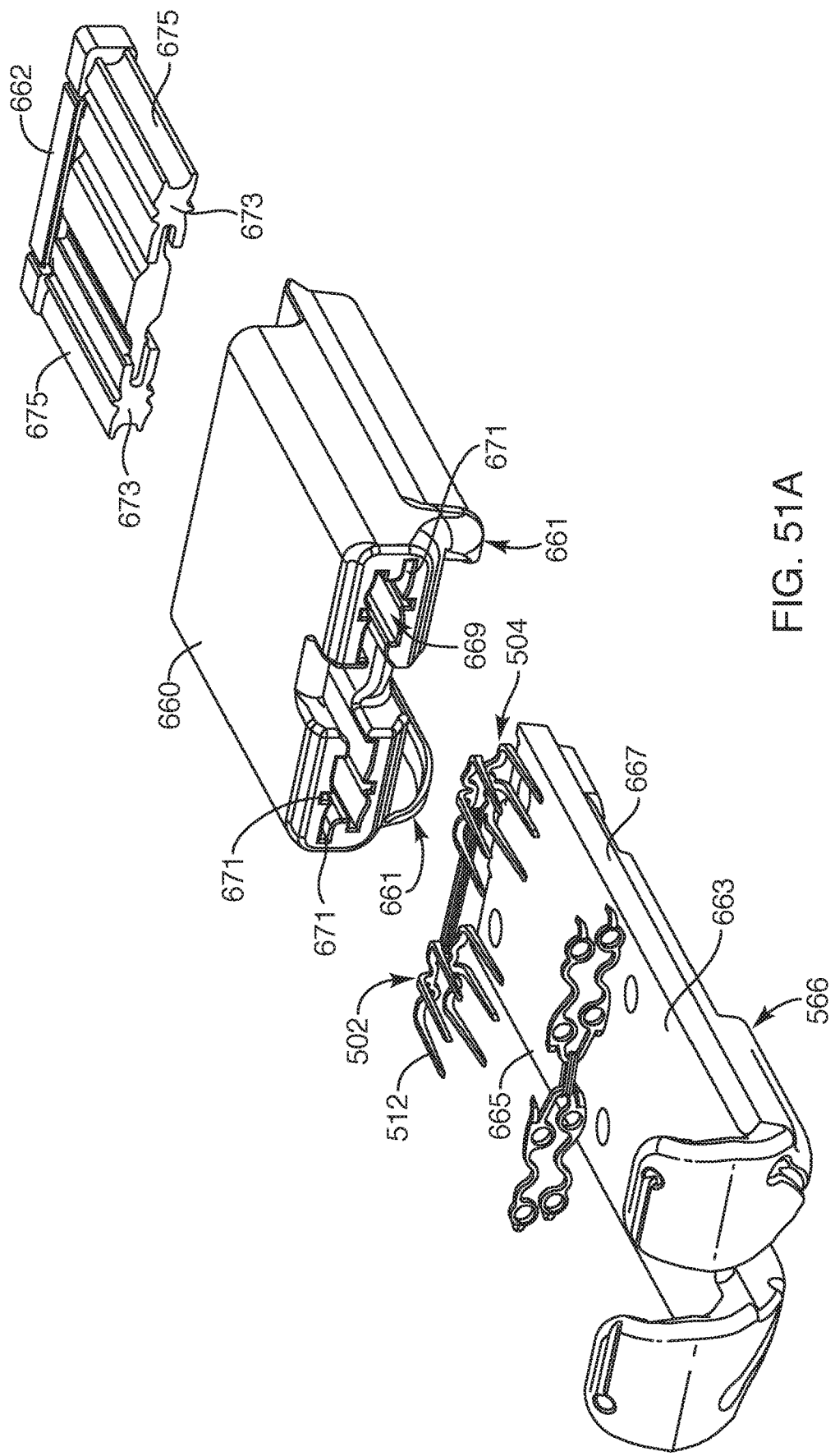
FIG. 51A is an enlarged exploded view of various components of a distal portion of the delivery device system, depicting various features of the components, according to another embodiment of the present invention.

With respect to FIG. 51A, additional detail will be described relative to the cradle 566, cartridge 660, and pusher member 662. In one embodiment, the cartridge 660 may include cartridge coupling portions 661 extending downward from opposing sides thereof. Such cartridge coupling portions 661 may be in the form of a C-arm or the like that may be sized and configured to wrap around and couple to opposing sides of a platform 663 of the cradle 566. The platform 663 may include first and second rails 665, 667 on opposing sides of the platform 663 sized and configured to receive the corresponding cartridge coupling portions 661. Such cartridge coupling portions 661 may be slidably coupled to the platform 663 so as to be linearly movable over and relative to the cradle 566.

Further, similar to previously described embodiments, the cartridge 660 may include a hollow portion 669 sized and configured to receive and hold the first and second anchors 502, 504. Such hollow portion 669 may include various grooves 671 and channels so as to correspond with a top profile of the first and second anchors 502, 504. The grooves 671 and channels may be defined by an inside wall surface of the cartridge 660. For example, the first and second anchors 502, 504 may be positioned within the hollow portion 669 such that the legs 512 of the first and second anchors 502, 504 may be slightly constrained against the wall surface defining the grooves 671 and channels within the hollow portion 669 of the cartridge 660 so that the first and second anchors 502, 504 may be effectively maintained within the cartridge 660.

The pusher member 662 may be sized and configured to be positioned within the hollow portion 669 of the cartridge 660. The pusher member 662 may include a distal end profile 673 and distal portion 675 sized and configured to be pushed through the hollow portion 669 of the cartridge 660, the distal end profile 673 and distal portion 675 having contours that correspond with the various grooves 671 and channels defined in the wall surface of the hollow portion 669 of the cartridge 660. Upon positioning the first and second anchors 502, 504 within the cartridge 660, the distal end profile 673 may be sized to push the first and second anchors 502, 504 from the cartridge 660, similar to that described in previous embodiments. With this arrangement, the first and second anchors 502, 504 can be temporarily housed within the cartridge 660 and effectively deployed from the cartridge 660 with the pusher member 662. As previously set forth, the cradle 566 may be formed of a metallic material and the cartridge 660 and pusher member 662 may be formed of a polymeric material, formed by employing molding and/or machining techniques as known to one of ordinary skill in the art.

Now with reference to FIGS. 52, 53A-53C, a method of deploying the first and second anchors 502, 504 with the delivery device 630 will now be described. With respect to FIGS. 52, 53A, and 53B, the cradle portion 564 of the applicator assembly 636 having the first and second plate members 506, 508 positioned in the cradle portion 564 may be positioned adjacent a tissue repair site 501. The physician may then position soft tissue 503 needing repair, such as a severed tendon or ligament, within the cradle portion 564 with abutting ends 505 of the soft tissue 503 positioned adjacently above and between the base ends 554 of the first and second plate members 506, 508. Upon the soft tissue 503 being appropriately positioned within the cradle portion 564 over the first and second plate members 506, 508, the physician may move the cartridge 660 with the first and second anchors 502, 504 linearly, as shown by arrows 672, from a first position to a second position by rotating the thumb wheel 654. Such positions may also be referenced as a cartridge first position and a cartridge second position or an anchor first position and an anchor second position.

Figure 52:
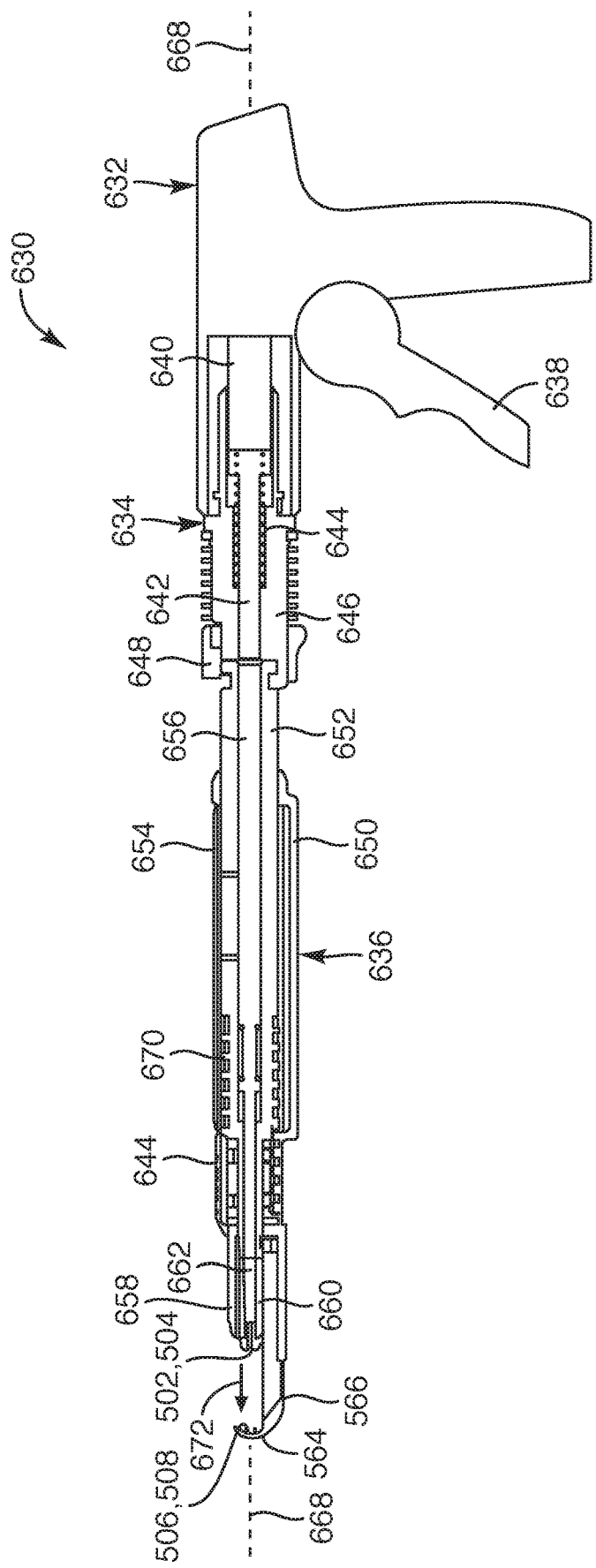
FIG. 52 is a cross-sectional view of the delivery device taken along section line A-A of FIG. 50, according to another embodiment of the present invention.

As shown in FIGS. 52 and 53C, the cartridge 660 is moved to the second position such that the exposed tips 536 (see FIG. 53A) of the first and second anchors 502, 504 are against end portions of the soft tissue 503. At this juncture, the physician may activate a deployment mechanism by pulling or compressing the trigger 638 of the trigger gun 632 to push the first and second anchors 502, 504 from the cartridge 660 and into the soft tissue 503. Upon compressing the trigger 638, a force may be placed along the axis 668 of the applicator assembly 634 from the push rod 642, to the applicator push rod 656 to the pusher member 662. The pusher member 662 forces the first and second anchors 502, 504 from the cartridge 660, through the soft tissue 503, and directly into the anvil buckets 570 (FIG. 43) with the engaging surface 624 of the legs 512 engaging the anvil buckets 570 to force and manipulate the legs 512 of the first and second anchor 502, 504 to move in a curling manner to wrap around portions of the first and second plate members 506, 508 and back into an underside of the soft tissue 503, as depicted in FIG. 54B.

Figure 54A:
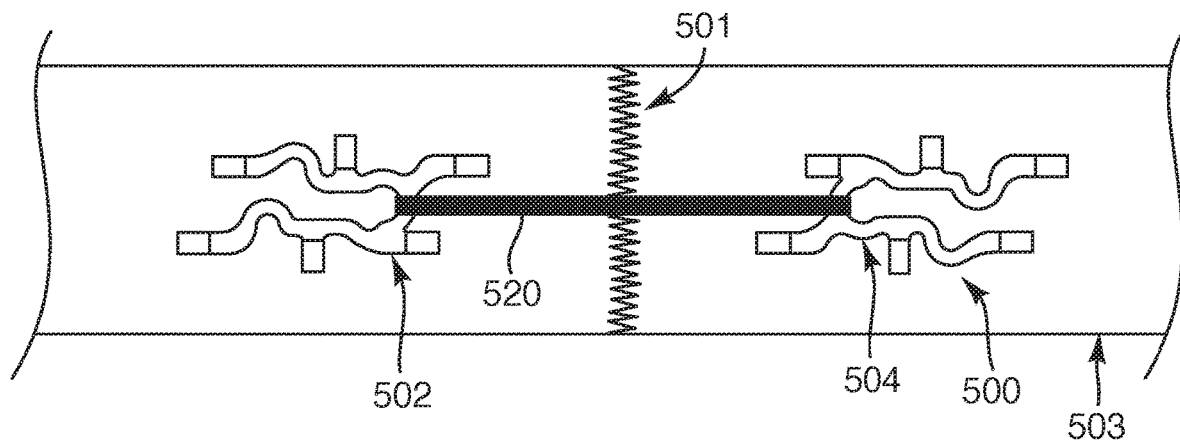
FIG. 54A is a top view of the repair device fixated to the severed soft tissue, according to another embodiment of the present invention.
Figure 54B:
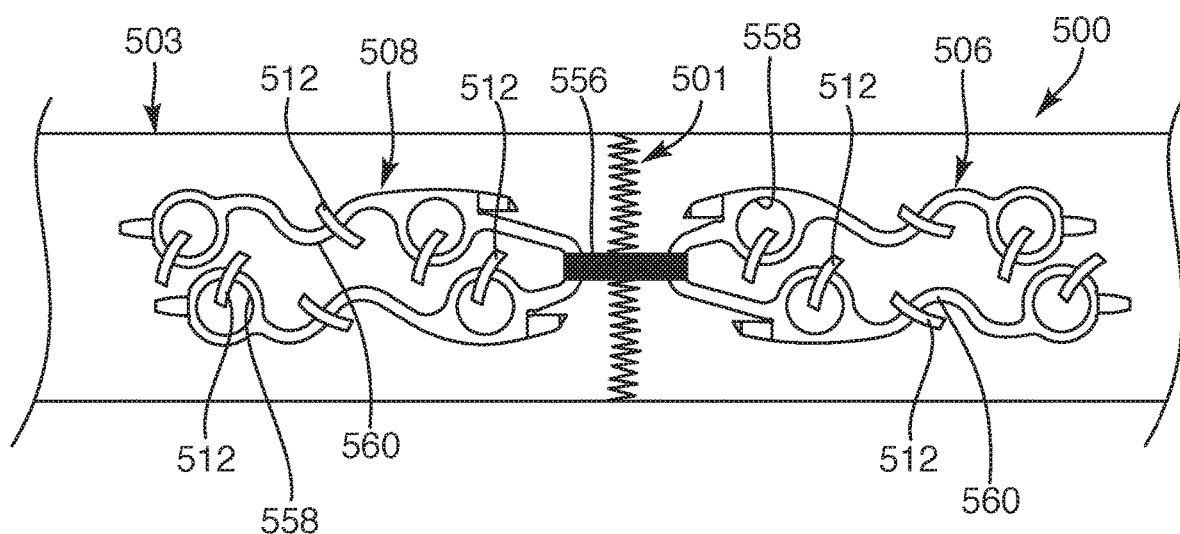
FIG. 54B is a bottom view of the repair device fixated to the severed soft tissue, according to another embodiment of the present invention.

With reference to FIGS. 54A and 54B, a top view and a bottom view of the deployed repair device 500 fixated to the soft tissue 503 of a soft tissue repair site is provided. Upon the first and second anchors 502, 504 being deployed from the cartridge 660 (FIG. 53C), the arms 512 extend through the apertures 558 of the first and second plate members 506, 508 to curl around portions of the first and second plate members 506, 508. Similarly, some of the legs 512 may extend and curl around the curved portions 560 of first and second plate members 506, 508. As depicted, the one or more anchor filaments 520 extend over the tissue repair site 501 and couple the first anchor 502 to the second anchor 504. Similarly, the one or more plate filaments 556 extend over the opposite side of the tissue repair site 501 and couple the first plate member 506 to the second plate member 508. As previously indicated, such filaments may resist elongation of the repair device 500 over a mid portion thereof. Further, depending upon the soft tissue 503 being repaired, such as a flexor tendon, such filaments facilitate the repair device 500 to move over a radius.

Figure 55A:
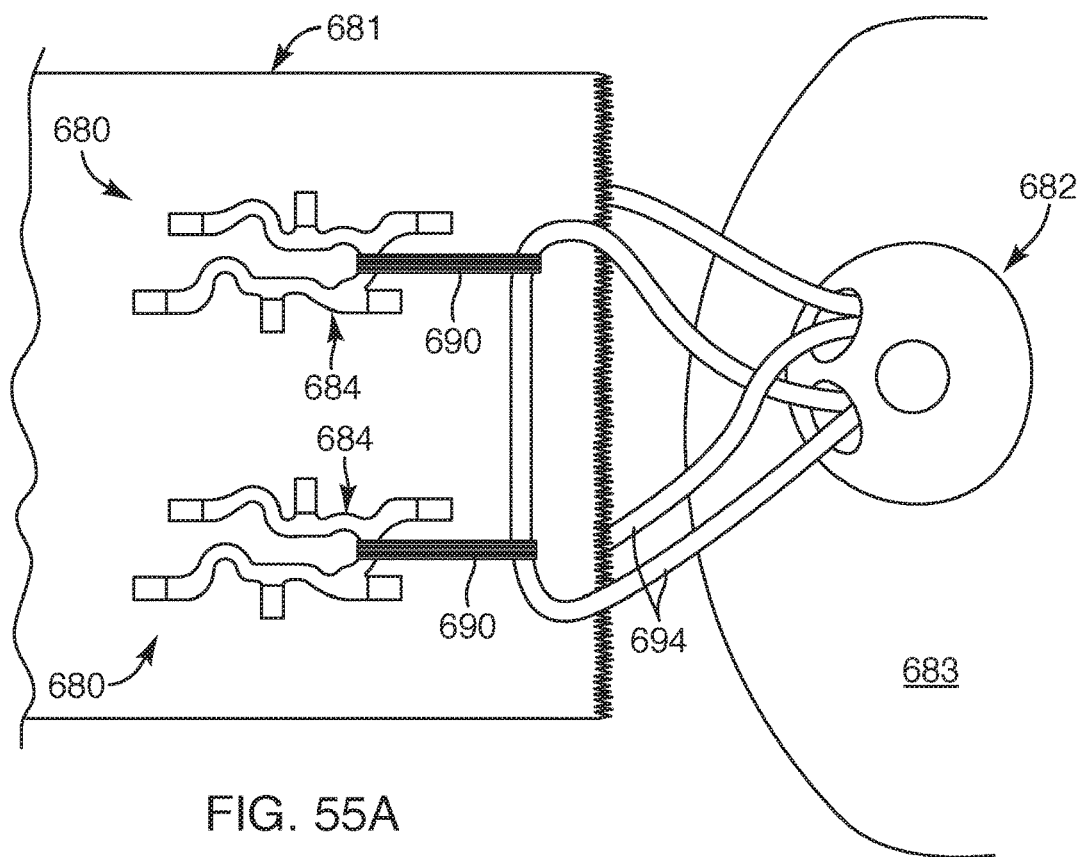
FIG. 55A is a top view of one or more repair devices, depicting first anchors of the one or more repair devices fixating soft tissue to bone with a bone anchor, according to another embodiment of the present invention.
Figure 55B:
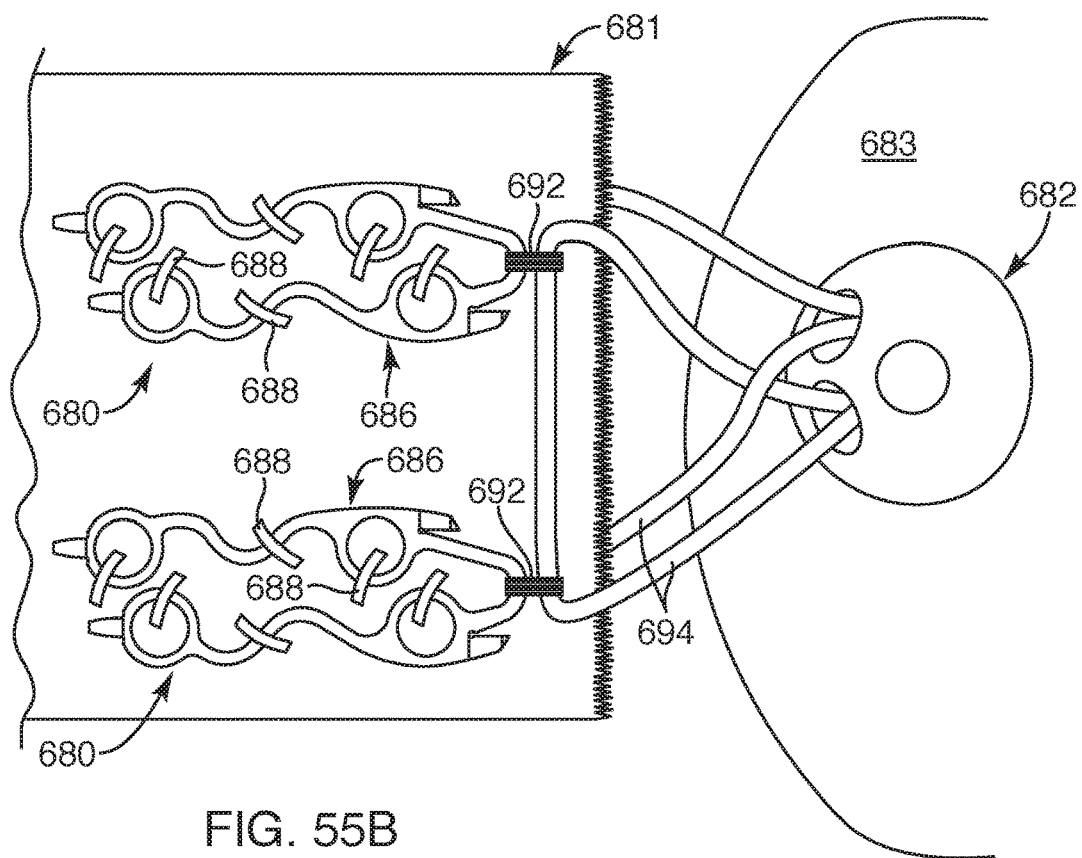
FIG. 55B is a bottom view of the one or more repair devices, depicting first plate members coupled to arms of the first anchors of the one or more repair devices fixating soft tissue to bone with the bone anchor, according to another embodiment of the present invention.

With reference to FIGS. 55A and 55B, a top view and a bottom view, respectively, of another embodiment of one or more repair devices 680 for fixating soft tissue 681, at a soft tissue repair site, to bone 683 with a bone anchor 684. The one or more repair devices 680 being similar to a portion of the previously described repair device. In this embodiment, such one or more repair devices 680 may employ, for example, a first anchor 684 coupled to a first plate member 686 such that legs 688 of the first anchor 684 extend through the soft tissue 681 and the legs 688 curl around portions of the first plate member 686, similar to previous described embodiments. Upon fixating the one or more repair devices 680 to the soft tissue 681, the one or more repair devices 680 may be coupled to the bone anchor 682. For example, an anchor filament 690 and a plate filament 692 extending from the respective first anchor 684 and the first plate member 686 may be coupled to the bone anchor 682. Such may be employed by extending a bone anchor filament 694 through the anchor filament 690 and the plate filament 692 and then inserting and fixating the bone anchor 682 to bone 683. In this manner, one or more first anchors 684 may be coupled to one or more first plate members 686 to fixate soft tissue 681 to bone 683. In another embodiment, the bone anchor filament 694 may be coupled directly to one or both of the first anchors 684 as well as the bone anchor filament 694 being coupled to one or both of the first plate members 686, instead of employing the anchor filament 690 and plate filament 692.

The components of the delivery device 630 may be formed and made with medical grade metallic materials, such as stainless steel, titanium, Nitinol, and/or alloys thereof or any other suitable metallic material or polymeric materials, such as liquid crystal polymers or acrylonitrile butadiene styrene ("ABS") or any other suitable polymeric materials known to one of ordinary skill in the art. Such device components may be formed by employing molding and/or machining techniques, or any other suitable techniques and processes known to one of ordinary skill in the art. Further, the first and second anchors 502, 504 and first and second plate members 506, 508, as set forth herein, may be laser cut from medical grade sheet material, such as stainless steel, titanium, Nitinol, and/or alloys thereof or made from a bioresorbable material such as zinc, polylactic-co-glycolic acid ("PLGA") or any other suitable bioresorbable material described herein or known by one of ordinary skill in the art.

Figure 56:
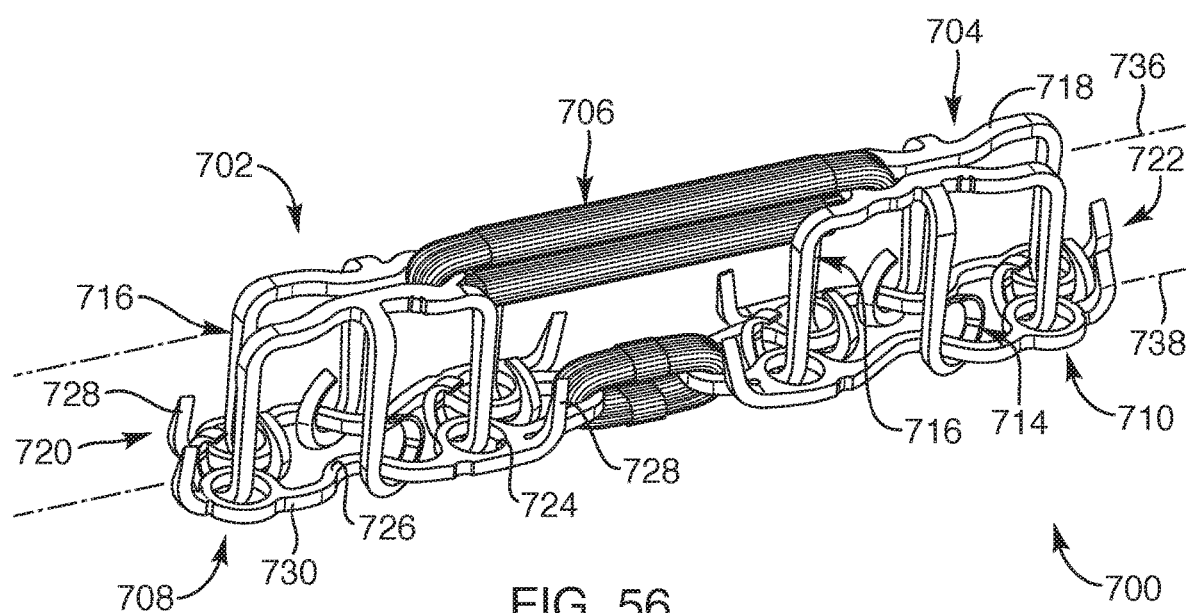
FIG. 56 is a perspective view of a repair device, depicting the repair device in a deployed state, according to another embodiment of the present invention.
Figure 57:
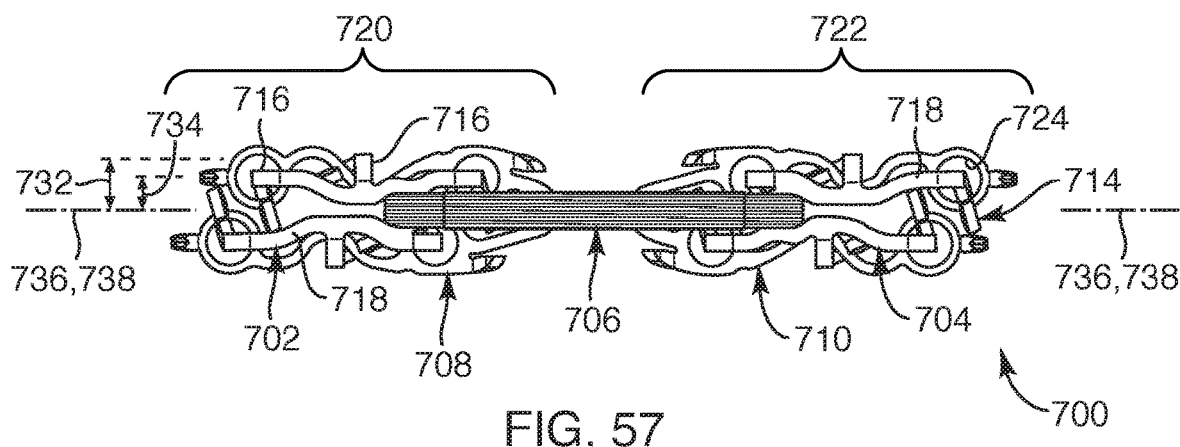
FIG. 57 is a top view of the repair device of FIG. 56, according to another embodiment of the present invention.

Now with reference to FIGS. 56-57, another embodiment of a repair device 700 that may be employed for fixating severed or ruptured soft tissue or for coupling soft tissue to bone, as depicted and described above, is provided. This embodiment of the repair device 700 is similar to the embodiment described and depicted relative to FIGS. 40 and 41, except this embodiment may include some minor modifications. For example, in this embodiment of the repair device, best depicted in FIG. 57, elongate portions 718 of first and second anchors 702, 704 may extend with less of a curve than that depicted in FIG. 40 and described as the curved portions 524. By straightening or forming the elongate portions 718 more linear than curved, the elongate portions 718 of this embodiment, upon being fixated to soft tissue, may be sized and configured to minimize quilting of the repair device 700 relative to the soft tissue so as to enhance gliding of the repair device within, for example, a tendon sheath. Further, in this embodiment, the elongate portions 718 may minimize any strain modulation in the first and second anchors 702, 704.

With respect to FIGS. 56-57, as set forth, the repair device 700 of this embodiment is similar to the previous embodiment (FIGS. 40-41) in most every structural respect and therefore that which is described relative to the previous embodiment is applicable to this embodiment. As depicted, the repair device 700 of this embodiment is shown in a deployed state or secured, coupled state. The repair device 700 may include the first anchor 702 and the second anchor 704 aligned longitudinally relative to each other and coupled together in a spaced manner with a first flexible member 706 or anchor filaments. Further, the repair device 700 may include a first plate 708 and a second plate 710 aligned longitudinally relative to each other and coupled together in a spaced manner with a second flexible member 712 or plate filaments. As depicted in FIG. 56, end portions 714 of legs 716 of the first and second anchors 702, 704 may be moved to bent, curled or wrapped positions upon being forced against the anvil buckets 570 of a cradle portion 564 (FIG. 45). With this arrangement, the end portions 714 of the legs 716 of each of the first and second anchors 702, 704 may be moved from a first position (similar to that depicted in FIG. 45) to a second position, as depicted in FIG. 57, such that end portions 714 of the legs 716 may be manipulated to bend or wrap around portions of the first and second plate members 708, 710 via the before discussed anvil buckets 570.

In one embodiment, the repair device 700 may include a first portion 720 and a second portion 722, the first portion 720 and the second portion 722 coupled with the first flexible member 706 and the second flexible member 712. The first portion 720 may include the first anchor 702 and the first plate 708, the first anchor 702 sized to couple to the first plate 708 via the legs 716 of the first anchor 702. The second portion 722 may include the second anchor 704 and the second plate 710, the second anchor 704 sized to couple to the second plate 710 via the legs 716 of the second anchor 704. In another embodiment, the first portion 720 or the second portion 722 of the repair device 700 may be employed to be fixated to soft tissue with a flexible member coupled to, for example, a bone anchor, similar to that depicted in FIGS. 55A and 55B. Such first portion 720 and/or second portion 722 may be appropriately sized relative to the soft tissue the repair device 700 is being employed with for fixating to soft tissue.

In another embodiment, the first and second anchors 702, 704 may each be formed from a flat structure, such as a sheet material, as a single monolithic structure. Once formed from the sheet material, such as by laser cutting or stamping, or any other suitable cutting method, portions of the first and second anchors 702, 704 may be bent toward a single side of the flat structure to form the legs 716. In one embodiment, each of the first and second anchors 702, 704 may include six legs or more. In another embodiment, each of the first and second anchors 702, 704 may include at least three legs, or at least four legs, or at least five legs. The number of legs 716 for a given anchor may correspond with portions of the first and second plates 708, 710, such as apertures 724 and/or undulations 726 defined in the structure of the first and second plates 708, 710. In another embodiment, the first and second anchors 702, 704 may include a flat structure or base portion that may extend in a generally U-shaped configuration with the legs 716 extending away from the U-shaped configuration in a generally common direction and away from a single side of the flat structure. In another embodiment, the first anchor 702 and the second anchor 704 may each include two legs on opposite ends thereof with two legs extending from a middle portion thereof to define six legs for each of the first and second anchors 702, 704. In another embodiment, the bottom end of the U-shaped configuration of the first and second anchors 702, 704 may face each other such that a bottom portion of the U-shaped configuration of the first and second anchors may be employed to wrap the first flexible member 706 to couple the first anchor 702 to the second anchor 704.

In another embodiment, the first and second plates 708, 710 may each define one or more apertures 724 or at least one aperture. In another embodiment, the first and second plates 708, 710 may define a multi-cellular structure. In another embodiment, the first and second plates 708, 710 may each include a single monolithic structure, formed from a sheet material. Once cut from the sheet material via, for example, laser cutting, stamping, or any other suitable method, the cut plate members may include tines 728 that may then be formed to extend in a generally common direction, such as, upward or from a single side of the plate member. Such tines 728 may include an orientation, such as upward and toward the side or end that the second flexible member 712 couples to the first and second plates 708, 710. In another embodiment, the first and second plates 708, 710 may extend with undulations 726 along a periphery 730 of the plate members. In another embodiment, apertures 724 defined in the structure may be formed internal the periphery 730 with the undulations 726. Such apertures 724 and/or undulations 726 defining the structure of the first and second plates 708, 710 may be sized and configured to receive the end portions 714 of the legs 716 of the first and second anchors 702, 704 to wrap or curl around portions of the first and second plates 708, 710.

As set forth in previous embodiments, the first and second flexible members 706, 712 may be formed of one or more filaments wrapped around inner portions of the first and second anchors 702, 704 and the first and second plates 708, 710, respectively. The one or more filaments may be any suitable filament, such as a biocompatible polymeric filament or the like, for example, ultra-high molecular weight polyethylene.

Figure 58:
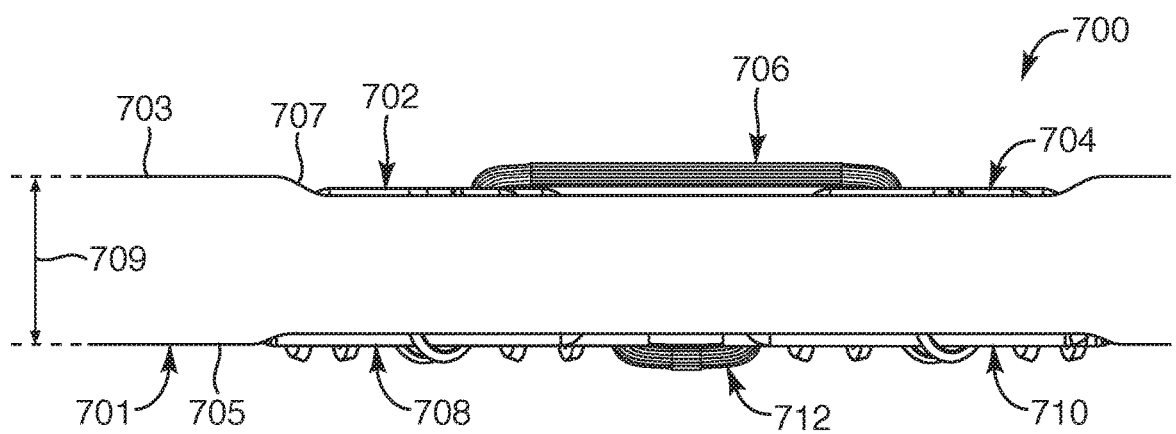
FIG. 58 is a side view of the repair device of FIG. 56 deployed within soft tissue, according to another embodiment of the present invention.

With respect to FIGS. 56 and 58, as set forth, the repair device 700 may be coupled together and fixated to soft tissue 701. Upon the repair device 700 being clamped or fixated to the soft tissue 701, exposed portions of the repair device 700 may be low profile relative to a first side 703 and second side 705 of the soft tissue 701. Further, the repair device 700 may create a recess 707 or depressed portion in the soft tissue 701 such that exposed portions of the repair device 700 provide minimal structure extending beyond a height 709 or diameter of the soft tissue 701. As depicted, the repair device 700 may be secured and maintained to the soft tissue 701 with the legs 716 and tines 728 at multiple locations. For example, at the first side 703 of the soft tissue 701, the legs 716 of the first and second anchors 702, 704 extend into the first side 703 and through the soft tissue 701 and back into the second side 705 of the soft tissue 701. At the second side 705 of the soft tissue, tines 728 extending from the first and second plates 708, 710 may extend into the soft tissue 701 as well as end portions 714 of the legs 716 extending into the soft tissue 701.

With respect to FIGS. 56, 57 and 58, in one embodiment, at the first side 703 of the soft tissue 701, the legs 716 of the first and second anchors 702, 704 extend into the soft tissue 701 such that adjacent positions of entrance into the soft tissue 701 by the legs 716 are not longitudinally aligned with each other. For example, middle legs may extend from the first and second anchors 702, 704 a first distance 732 from a longitudinal axis 736 of the first and second anchors 702, 704, and the legs 716 on opposite ends of the first and second anchors 702, 704 may extend relative to the longitudinal axis 736 of the first and second anchors 702, 704 a second distance 734, the first distance 732 being larger than the second distance 734. In another embodiment, the first distance may be smaller than the second distance. Similarly, in one embodiment, the adjacent positions of entrance into the soft tissue 701 at the second side 705 of the soft tissue 701 of the end portions 714 of the legs 716 relative to the tines 728 of the plates are not longitudinally aligned. In other words, the end portions 714 of the legs 716 may be positioned at different distances than the tines relative to a longitudinal axis of the plate members. In this manner, as a force is placed upon the soft tissue with the repair device 700 fixated thereto, the longitudinally extending tissue fibers may be less apt to longitudinally tear along a common longitudinal line where adjacent arms extend through the soft tissue 701.

Furthermore, by coupling the legs 716 of the first and second anchors 702, 704 to wrap around portions of the first and second plates 708, 710, a force that may be placed on the soft tissue may be maximized without the repair device 700 being pulled out of the soft tissue 701. In other words, the soft tissue 701 may fail before the low profile repair device 700 fails such that the repair device 700 may remain intact and coupled together.

Figure 59:
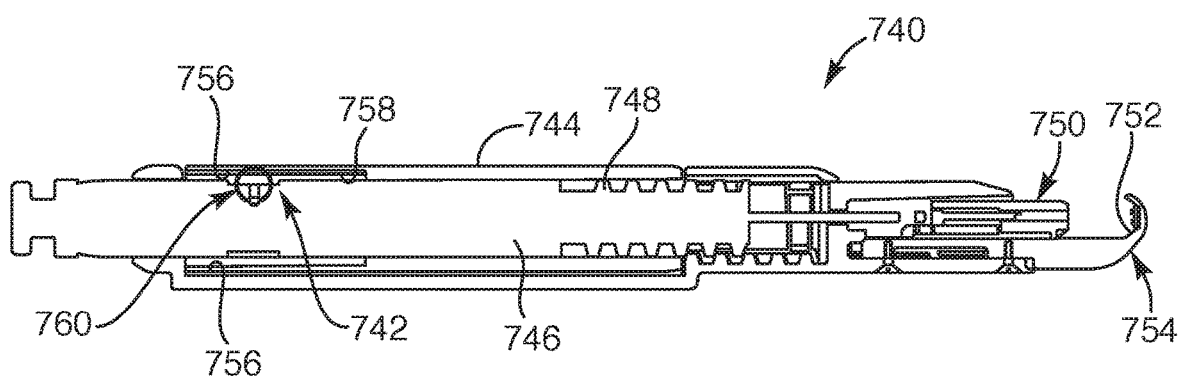
FIG. 59 is a cross-sectional view of an applicator assembly, depicting a slip clutch element integrated with the applicator assembly, according to another embodiment of the present invention.
Figure 59A:
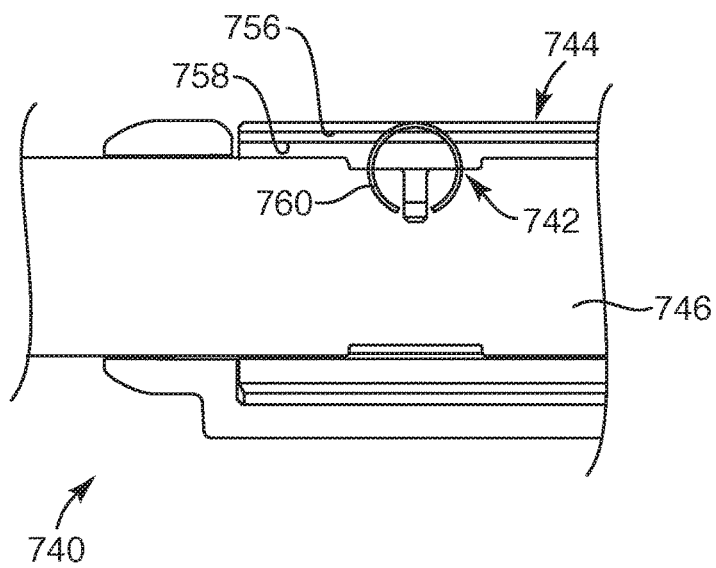
FIG. 59A is an enlarged view of the slip clutch element, according to another embodiment of the present invention.
Figure 59B:
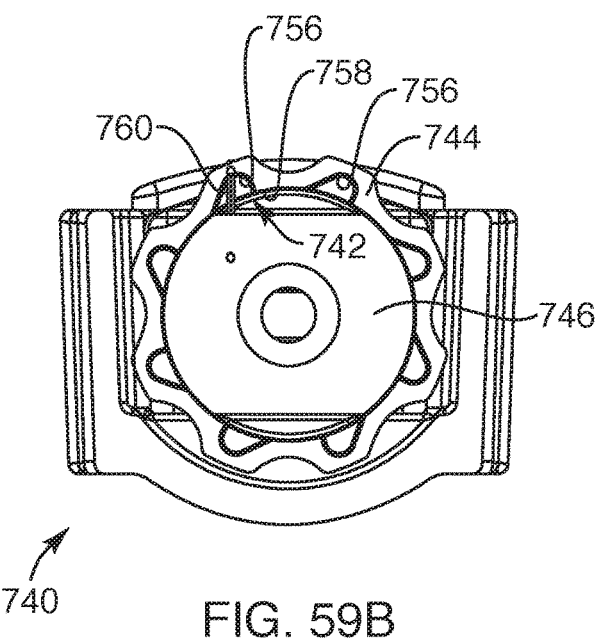
FIG. 59B is a cross-sectional view of the applicator assembly taken laterally relative to the longitudinal length of the applicator assembly along the slip clutch element, according to another embodiment of the present invention.

Now with reference to FIGS. 59, 59A, and 59B, another embodiment of an applicator assembly 740 with an integrated slip clutch element 742 or slip clutch arrangement is provided. The applicator assembly 740 of this embodiment may include similar components as the applicator assembly 636 described and depicted in FIGS. 50, 51, and 52. In this embodiment, the slip clutch element 742 integrated with the applicator assembly 740 may be integrated into a thumb wheel 744 and a worm drive 746 of the applicator assembly 740. As in previous embodiments, the worm drive 746 may include threads 748 such that, upon rotating the thumb wheel 744, the worm drive 746 moves linearly to move a cartridge 750 toward a bed surface 752 of a cradle portion 754. The thumb wheel 744, at least along a longitudinal portion thereof, may include slots 756 or the like extending longitudinally along the length and along an internal radial surface 758 of the thumb wheel 744. The worm drive 746 may include a finger 760 or clutch element (or finger element) in the form, for example, a wire or ring such that a portion of the finger 760 extends into one of the longitudinally extending slots 756 defined in the thumb wheel 744. The finger 760 may be fixed and embedded into the worm drive 746. As the thumb wheel 744 is rotated to move the worm drive 746 distally and, thus, move the cartridge 750 distally toward the cradle portion 754, the worm drive 746 also moves rotationally and linearly such that the finger 760 moves distally relative to the thumb wheel 744 along one of the slots 756 defined in the internal radial surface 758 of the thumb wheel 744. Upon the cartridge 750 being moved distally against the soft tissue positioned in the cradle portion 754 and pressing against the soft tissue with a predetermined force, the finger 760 extending in one slot may slip out of the one slot and move to an adjacent slot (and continue to move to adjacent slots) as the thumb wheel 744 is rotated, thereby, removing additional distal movement of the worm drive 746 and limiting any additional force of the cartridge 750 against the soft tissue. In this manner, the slip clutch element 742 (finger 760 cooperating with the internal geometry of the slot 756) may be sized and configured with a predetermined stiffness to be a torque limiter to facilitate consistent torque or clamping force of the cartridge 750 against the soft tissue. Further, the slip clutch element 742 integrated in the applicator assembly 740 (or any one of the delivery device systems set forth herein) may be sized and configured to facilitate consistent deployment and coupling of any one of the repair device embodiments, such as repair device 700, to the soft tissue so as to better control the outcome of fixating the repair device 700 to soft tissue.

In one embodiment, the finger 760 may be a wire, such as a linear wire or a wire with a radius, embedded in the worm drive 746. In another embodiment, the finger 760 may be a circular wire member or a ring structure fixed to and embedded into the worm drive 746. In still another embodiment, the finger 760 may be positioned off-center relative to an axis of the worm drive 746 (as depicted in FIG. 59B) so that the finger 760 may slip out of a given slot 756 when rotating the thumb wheel 744 in one direction, but withstand slipping out of a given slot 756 when rotating the thumb wheel 744 in the opposite direction. In another embodiment, the force applied to the soft tissue by a distal end of the cartridge 750 is a function of a bendability of the finger 760 and the geometry of the internal slot 756. In another embodiment, the finger 760 may be formed from a Nitinol material. In another embodiment, the finger 760 may be a flexible polymeric finger molded with the worm drive 746 or embedded in the worm drive 746.

Figure 60:
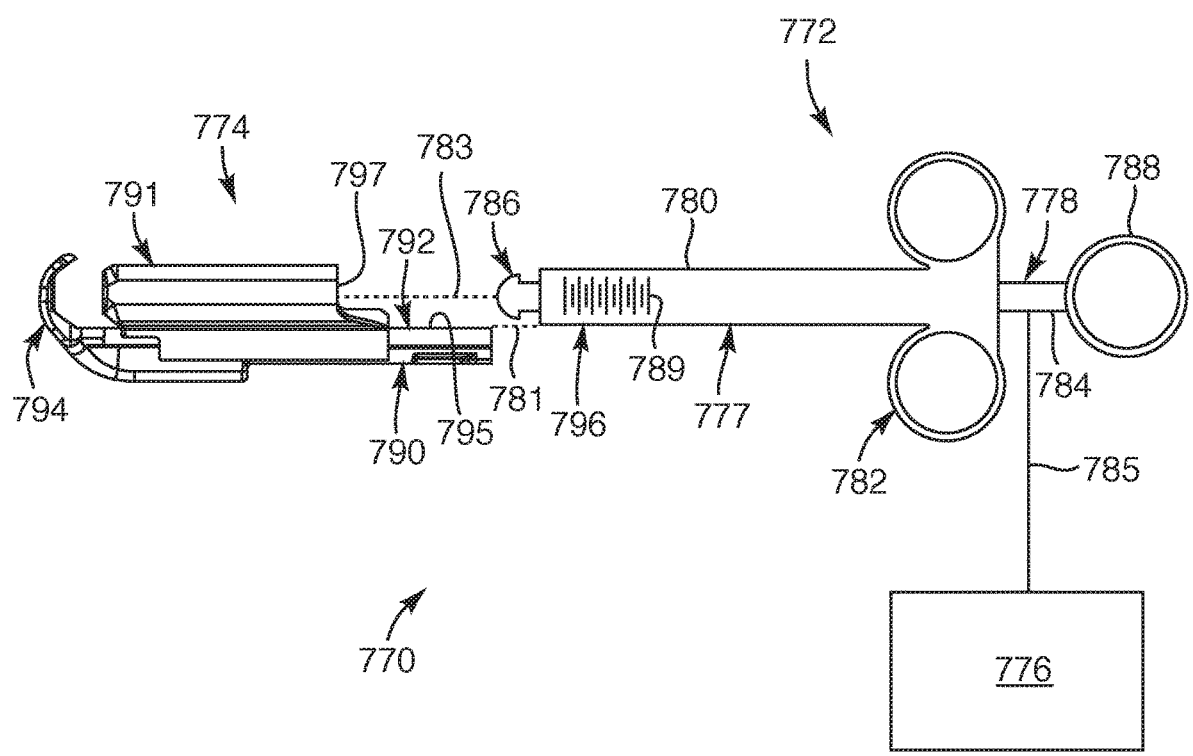
FIG. 60 is another embodiment of a delivery device for delivering a repair device, according to the present invention.

With reference to FIG. 60, another embodiment of a delivery device 770, in simplified form, is provided. The delivery device 770 may include an actuator member 772, a device delivery portion 774, and a firing member 776. The actuator member 772 may include a body 777 and an actuator portion 778, the body 777 sized to receive a portion of the actuator portion 778 in a syringe like manner. The body 777 may include, for example, a tube structure 780 with a finger holder 782 at a proximal end thereof. The finger holder 782 may include two ring-like structures for a physician to position two fingers therein. The actuator portion 778 may include an elongate portion 784 extending through the tube structure 780 with a coupling structure 786 at a distal end and a ring structure 788 at a proximal end of the elongate portion 784. The tube structure 780 may include indicia 789 on the tube structure 780 so as to indicate to a physician a thickness or size of the soft tissue being fixated to ensure an appropriately sized repair device is fixated to the soft tissue. The coupling structure 786 may be sized and configured to couple to the device delivery portion 774.

The device delivery portion 774 may include a cradle 790 and a cartridge 791, similar to the cradle and cartridge described in previous embodiments. The cradle 790 may include a proximal portion 792 and a cradle portion 794, the proximal portion 792 including an upper side 795 with a track (not shown) that may couple to a corresponding track along a distal side portion 796 of the tube structure 780, as indicated by dotted line 781. The coupling structure 786 of the actuator member 772, as previously indicated, may be coupled to a proximal side 797 of the cartridge 791, as indicated by dotted line 783. The cradle 790 is coupled to the tube structure 780 in a fixed manner. The cartridge 791 may also be coupled to the coupling structure 786 in a fixed manner, however, the cartridge 791 may linearly slide relative to the cradle 790, as discussed in previous embodiments. In this manner, linear movement of the actuator portion 778 may linearly move the cartridge 791 relative to the cradle 790 such that the cradle 790 and tube structure 780 may remain fixed and stationary.

As set forth, the firing member 776 may be operatively coupled to the actuator member 772 and the device delivery portion 774, as indicated by dotted line 785. In one embodiment, the firing member 776 may be activated with and include a manual trigger and handle such that the trigger acts like a lever to move a pusher member, similar to previous embodiments. In another embodiment, the firing member 776 may activate a pusher member hydraulically or pneumatically, or any other suitable structure or means such that the firing member may be activated manually with a lever and translate the required force to a pusher member to effectively eject anchors from the cartridge and deploy the repair device.

Once the actuator member 772 is coupled to the device delivery portion 774, a physician may then position the severed soft tissue within the cradle portion 794, similar to that described in previous embodiments. Upon positioning the severed soft tissue within the cradle portion 794, the physician may then grasp the actuator member 772 by placing ones thumb in the proximal ring structure 788 and two fingers in the finger holders 782. The physician may then readily move a distal end of the cartridge 791 toward a cradle portion 794 of the cradle 790 and snug over the soft tissue positioned in the cradle portion 794. If the physician is not satisfied with the soft tissue positioned in the cradle portion 794, the physician may readily pull back the cartridge 791 by actuating the actuator portion 778 proximally, view and re-arrange the soft tissue in the cradle portion 794, and then actuate the actuator portion 778 distally to move the cartridge 791 against the soft tissue, as previously set forth. Once the physician is satisfied with the positioning of the soft tissue with the cartridge 791 actuated against the soft tissue, the physician may activate the firing member 776. The firing member 776 may then be activated to force one or more anchors from the cartridge 791 and through the soft tissue such that legs of the one or more anchors may wrap around portions of one or more plates positioned under the soft tissue. In this manner, the delivery device 770 may be employed to fixate any one of the repair device embodiments described herein to soft tissue.

The various repair device embodiments or other embodiments disclosed herein may be applied to any one of various soft tissue to soft tissue repairs as well as soft tissue to bone repairs. For example, the various repair device embodiments may be employed for flexor tendon repairs, patellar tendon repairs, Achilles tendon repairs, quadriceps tendon repairs, and/or bicep tendon repairs, or any other tendon, ligament, and tendon/ligament to bone repairs. As such, the repair device may be appropriately sized for proper fixation to the different sized or types of soft tissue.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:

1. A delivery device system for fixating a repair device to soft tissue at a soft tissue repair site, comprising:
    an applicator assembly including:
        a housing with a cradle fixed to the housing;
        a worm drive positioned within the housing with threads extending over a portion of the worm drive;
        a cartridge coupled to a distal end of the worm drive, the cartridge configured to hold anchors of the repair device, the cartridge configured to be linearly moved relative to a bed surface of the cradle;
        a thumb wheel disposed around the worm drive, the thumb wheel configured to be manually rotated to linearly move the cartridge; and
        a flexible finger element coupled to and extending from the worm drive and configured to cooperate with a slot defined in an internal radial surface of the thumb wheel;
        wherein, upon manually rotating the thumb wheel, the worm drive rotates upon the flexible finger element being maintained within the slot defined in the internal radial surface of the thumb wheel.

2. The delivery device system of claim 1, wherein the flexible finger element is sized to linearly translate along the slot.

3. The delivery device system of claim 2, wherein, upon the cartridge being linearly moved against soft tissue positioned in the cradle, the flexible finger element is configured to slip-out of the slot to an adjacently extending slot to prevent further linear movement of the cartridge toward the bed surface of the cradle.

4. The delivery device system of claim 1, wherein the flexible finger element comprises a circular member.

5. The delivery device system of claim 1, wherein the flexible finger element comprises a ring structure.

6. The delivery device system of claim 1, wherein the flexible finger element is fixed to the worm drive.

7. The delivery device system of claim 1, wherein the flexible finger element is positioned off-center relative to an axis of the worm drive.

8. The delivery device system of claim 1, wherein the flexible finger element is configured to flex and move out of the slot so that the flexible finger element moves along the internal radial surface of the thumb wheel to limit a force applied to the soft tissue upon the cartridge being linearly moved against the soft tissue.

9. The delivery device system of claim 8, wherein the force applied to the soft tissue by a distal end of the cartridge is a function of bendability of the flexible finger element.

10. The delivery device system of claim 1, wherein, upon the cartridge being linearly moved against the soft tissue, the flexible finger element is configured to flex and move out of the slot to prevent further linear movement of the cartridge against the soft tissue.

\* \* \* \* \*